(12) United States Patent
Khairkhahan

(10) Patent No.: US 9,592,121 B1
(45) Date of Patent: Mar. 14, 2017

(54) DEVICE, SYSTEM, AND METHOD FOR TRANSCATHETER TREATMENT OF VALVULAR REGURGITATION

(71) Applicant: Middle Peak Medical, Inc., Palo Alto, CA (US)

(72) Inventor: Alexander K. Khairkhahan, Palo Alto, CA (US)

(73) Assignee: Middle Peak Medical, Inc., Palo Alto, CA (US)

( * ) Notice: Subject to any disclaimer, the term of this patent is extended or adjusted under 35 U.S.C. 154(b) by 0 days.

(21) Appl. No.: 15/153,480

(22) Filed: May 12, 2016

Related U.S. Application Data

(60) Provisional application No. 62/252,336, filed on Nov. 6, 2015.

(51) Int. Cl.
*A61F 2/24* (2006.01)
*A61B 17/064* (2006.01)

(52) U.S. Cl.
CPC .......... *A61F 2/2454* (2013.01); *A61B 17/064* (2013.01); *A61F 2/2427* (2013.01); *A61B 2017/0649* (2013.01); *A61F 2210/0014* (2013.01); *A61F 2220/0016* (2013.01); *A61F 2250/0098* (2013.01)

(58) Field of Classification Search
CPC ...... A61F 2210/0014; A61F 2250/0098; A61F 2220/0016; A61F 2/2427; A61F 2/2454; A61B 2017/0649; A61B 17/0644
USPC ....................................................... 623/2.11
See application file for complete search history.

(56) References Cited

U.S. PATENT DOCUMENTS

| | | |
|---|---|---|
| 3,491,376 A | 1/1970 | Shiley |
| 3,503,079 A | 3/1970 | Smith |
| 3,656,185 A | 4/1972 | Carpentier |
| 3,671,979 A | 6/1972 | Moulopoulos |
| 3,874,388 A | 4/1975 | King et al. |
| 3,898,701 A | 8/1975 | La Russa |
| 3,938,197 A | 2/1976 | Milo |
| 4,007,743 A | 2/1977 | Blake |
| 4,011,601 A | 3/1977 | Clune et al. |
| 4,042,979 A | 8/1977 | Angell |

(Continued)

FOREIGN PATENT DOCUMENTS

| | | |
|---|---|---|
| CN | 101056596 | 10/2007 |
| CN | 101068508 | 11/2007 |

(Continued)

OTHER PUBLICATIONS

Biocina et al., *Mitral Valve Repair With the New Mitrofast® Repair System*, Dubrava University Hospital, Zagreb, Crotia, Mitrofast Abstract European Soc CVS 55th Congress—May 11-14, 2006 Suppl 1 to vol. 5.

(Continued)

*Primary Examiner* — Eric Rosen
*Assistant Examiner* — George J Ulsh
(74) *Attorney, Agent, or Firm* — Knobbe, Martens, Olson & Bear, LLP

(57) ABSTRACT

The invention relates to a device for use in the transcatheter treatment of mitral valve regurgitation, specifically a coaptation assistance element for implantation across the valve; a system including the coaptation assistance element and anchors for implantation; a system including the coaptation assistance element and delivery catheter; and a method for transcatheter implantation of a coaptation element across a heart valve.

21 Claims, 28 Drawing Sheets

FULL IMPLANT OPENING - SECTIONED

(56) References Cited

U.S. PATENT DOCUMENTS

| | | |
|---|---|---|
| 4,078,268 A | 3/1978 | Possis |
| 4,204,283 A | 5/1980 | Bellhouse et al. |
| 4,218,783 A | 8/1980 | Reul et al. |
| 4,261,342 A | 4/1981 | Aranguren Duo |
| 4,263,680 A | 4/1981 | Reul et al. |
| 4,275,469 A | 6/1981 | Gabbay |
| RE31,040 E | 9/1982 | Possis |
| 4,352,211 A | 10/1982 | Parravicini |
| 4,488,318 A | 12/1984 | Kaster |
| 4,490,859 A | 1/1985 | Black et al. |
| 4,491,986 A | 1/1985 | Gabbay |
| 4,561,129 A | 12/1985 | Arpesella |
| 4,687,483 A | 8/1987 | Fisher et al. |
| 4,705,516 A | 11/1987 | Barone et al. |
| 4,759,758 A | 7/1988 | Gabbay |
| 4,790,843 A | 12/1988 | Carpentier et al. |
| 4,960,424 A | 10/1990 | Grooters |
| 4,994,077 A | 2/1991 | Dobben |
| 5,002,567 A | 3/1991 | Bona et al. |
| 5,078,737 A | 1/1992 | Bona et al. |
| 5,131,905 A | 7/1992 | Grooters |
| 5,197,980 A | 3/1993 | Gorshkov et al. |
| 5,258,023 A | 11/1993 | Reger |
| 5,332,402 A | 7/1994 | Teitelbaum |
| 5,344,442 A | 9/1994 | Deac |
| 5,397,347 A | 3/1995 | Cuilleron et al. |
| 5,397,348 A | 3/1995 | Campbell et al. |
| 5,413,599 A | 5/1995 | Imachi et al. |
| 5,487,760 A | 1/1996 | Villafana |
| 5,500,015 A | 3/1996 | Deac |
| 5,522,886 A | 6/1996 | Milo |
| 5,554,186 A | 9/1996 | Guo et al. |
| 5,593,435 A | 1/1997 | Carpentier et al. |
| 5,658,313 A | 8/1997 | Thal |
| 5,662,704 A | 9/1997 | Gross |
| 5,716,370 A | 2/1998 | Williamson, IV et al. |
| 5,733,331 A | 3/1998 | Peredo |
| 5,824,065 A | 10/1998 | Gross |
| 5,824,066 A | 10/1998 | Gross |
| 5,824,067 A | 10/1998 | Gross |
| 5,855,601 A | 1/1999 | Bessler et al. |
| 5,888,240 A | 3/1999 | Carpentier et al. |
| 5,957,949 A | 9/1999 | Leonhardt et al. |
| 6,007,577 A | 12/1999 | Vanney et al. |
| 6,024,096 A | 2/2000 | Buckberg |
| 6,042,607 A | 3/2000 | Williamson, IV et al. |
| 6,045,497 A | 4/2000 | Schweich et al. |
| 6,066,160 A | 5/2000 | Colvin et al. |
| 6,086,612 A | 7/2000 | Jansen |
| 6,113,631 A | 9/2000 | Jansen |
| 6,162,233 A | 12/2000 | Williamson, IV et al. |
| 6,217,610 B1 | 4/2001 | Carpentier et al. |
| 6,221,104 B1 | 4/2001 | Buckberg et al. |
| 6,250,308 B1 | 6/2001 | Cox |
| 6,264,602 B1 | 7/2001 | Mortier et al. |
| 6,287,339 B1 | 9/2001 | Vazquez et al. |
| 6,296,662 B1 | 10/2001 | Caffey |
| 6,299,637 B1 | 10/2001 | Shaolian et al. |
| 6,312,447 B1 | 11/2001 | Grimes |
| 6,312,464 B1 | 11/2001 | Navia |
| 6,332,893 B1 | 12/2001 | Mortier et al. |
| 6,358,277 B1 | 3/2002 | Duran |
| 6,383,147 B1 | 5/2002 | Stobie |
| 6,391,053 B1 | 5/2002 | Brendzel et al. |
| 6,391,054 B2 | 5/2002 | Carpentier et al. |
| 6,402,679 B1 | 6/2002 | Mortier et al. |
| 6,402,780 B2 | 6/2002 | Williamson, IV et al. |
| 6,409,758 B2 | 6/2002 | Stobie et al. |
| 6,419,695 B1 | 7/2002 | Gabbay |
| 6,439,237 B1 | 8/2002 | Buckberg et al. |
| 6,450,171 B1 | 9/2002 | Buckberg et al. |
| 6,454,799 B1 | 9/2002 | Schreck |
| 6,458,153 B1 | 10/2002 | Bailey et al. |
| 6,482,228 B1 | 11/2002 | Norred |
| 6,540,782 B1 | 4/2003 | Snyders |
| 6,544,167 B2 | 4/2003 | Buckberg et al. |
| 6,565,603 B2 | 5/2003 | Cox |
| 6,569,198 B1 | 5/2003 | Wilson et al. |
| 6,602,288 B1 | 8/2003 | Cosgrove et al. |
| 6,602,289 B1 | 8/2003 | Colvin et al. |
| 6,626,930 B1 | 9/2003 | Allen et al. |
| 6,629,534 B1 | 10/2003 | St. Goar et al. |
| 6,652,578 B2 | 11/2003 | Bailey et al. |
| 6,676,698 B2 | 1/2004 | McGuckin, Jr. et al. |
| 6,682,559 B2 | 1/2004 | Myers et al. |
| 6,702,852 B2 | 3/2004 | Stobie et al. |
| 6,719,790 B2 | 4/2004 | Brendzel et al. |
| 6,752,813 B2 | 6/2004 | Goldfarb et al. |
| 6,764,510 B2 | 7/2004 | Vidlund et al. |
| 6,780,200 B2 | 8/2004 | Jansen |
| 6,790,237 B2 | 9/2004 | Stinson |
| 6,797,002 B2 | 9/2004 | Spence et al. |
| 6,800,090 B2 | 10/2004 | Alferness et al. |
| 6,805,710 B2 | 10/2004 | Bolling et al. |
| 6,821,297 B2 | 11/2004 | Snyders |
| 6,837,247 B2 | 1/2005 | Buckberg et al. |
| 6,840,246 B2 | 1/2005 | Downing |
| 6,846,324 B2 | 1/2005 | Stobie |
| 6,869,444 B2 | 3/2005 | Gabbay |
| 6,908,478 B2 | 6/2005 | Alferness et al. |
| 6,911,043 B2 | 6/2005 | Myers et al. |
| 6,926,730 B1 | 8/2005 | Nguyen et al. |
| 6,966,925 B2 | 11/2005 | Stobie |
| 6,991,649 B2 | 1/2006 | Sievers |
| 6,997,950 B2 | 2/2006 | Chawla |
| 7,018,408 B2 | 3/2006 | Bailey et al. |
| 7,037,333 B2 | 5/2006 | Myers et al. |
| 7,048,754 B2 | 5/2006 | Martin et al. |
| 7,056,280 B2 | 6/2006 | Buckberg et al. |
| 7,070,618 B2 | 7/2006 | Streeter |
| 7,077,861 B2 | 7/2006 | Spence |
| 7,077,862 B2 | 7/2006 | Vidlund et al. |
| 7,083,628 B2 | 8/2006 | Bachman |
| 7,112,207 B2 | 9/2006 | Allen et al. |
| 7,122,043 B2 | 10/2006 | Greenhalgh et al. |
| 7,160,322 B2 | 1/2007 | Gabbay |
| 7,166,126 B2 | 1/2007 | Spence et al. |
| 7,175,656 B2 | 2/2007 | Khairkhahan |
| 7,195,641 B2 | 3/2007 | Palmaz et al. |
| 7,217,284 B2 | 5/2007 | Houser et al. |
| 7,226,467 B2 | 6/2007 | Lucatero et al. |
| 7,275,546 B2 | 10/2007 | Buckberg et al. |
| 7,291,168 B2 | 11/2007 | Macoviak et al. |
| 7,294,148 B2 | 11/2007 | McCarthy |
| 7,296,577 B2 | 11/2007 | Taylor et al. |
| 7,316,706 B2 | 1/2008 | Bloom et al. |
| 7,320,704 B2 | 1/2008 | Lashinski et al. |
| 7,335,213 B1 | 2/2008 | Hyde et al. |
| 7,338,520 B2 | 3/2008 | Bailey et al. |
| 7,341,584 B1 | 3/2008 | Starkey |
| 7,357,814 B2 | 4/2008 | Gabbay |
| 7,374,572 B2 | 5/2008 | Gabbay |
| RE40,377 E | 6/2008 | Williamson, IV et al. |
| 7,381,220 B2 | 6/2008 | Macoviak et al. |
| 7,396,364 B2 | 7/2008 | Moaddeb et al. |
| 7,435,257 B2 | 10/2008 | Lashinski et al. |
| 7,445,630 B2 | 11/2008 | Lashinski et al. |
| 7,455,689 B2 | 11/2008 | Johnson |
| 7,485,143 B2 | 2/2009 | Webler et al. |
| 7,510,573 B2 | 3/2009 | Gabbay |
| 7,510,576 B2 | 3/2009 | Langberg et al. |
| 7,527,646 B2 | 5/2009 | Rahdert et al. |
| 7,527,647 B2 | 5/2009 | Spence |
| 7,530,998 B1 | 5/2009 | Starkey |
| 7,534,259 B2 | 5/2009 | Lashinski et al. |
| 7,556,645 B2 | 7/2009 | Lashinski et al. |
| 7,559,936 B2 | 7/2009 | Levine |
| 7,563,267 B2 | 7/2009 | Goldfarb et al. |
| 7,563,273 B2 | 7/2009 | Goldfarb et al. |
| 7,591,847 B2 | 9/2009 | Navia et al. |
| 7,608,091 B2 | 10/2009 | Goldfarb et al. |
| 7,611,534 B2 | 11/2009 | Kapadia et al. |
| 7,621,948 B2 | 11/2009 | Herrmann et al. |
| 7,648,532 B2 | 1/2010 | Greenhalgh et al. |

(56) References Cited

U.S. PATENT DOCUMENTS

| | | |
|---|---|---|
| 7,655,015 B2 | 2/2010 | Goldfarb et al. |
| 7,658,762 B2 | 2/2010 | Lashinski et al. |
| 7,658,763 B2 | 2/2010 | Stobie |
| 7,666,224 B2 | 2/2010 | Vidlund et al. |
| 7,674,286 B2 | 3/2010 | Alfieri et al. |
| 7,678,145 B2 | 3/2010 | Vidlund et al. |
| 7,682,391 B2 | 3/2010 | Johnson |
| 7,691,144 B2 | 4/2010 | Chang et al. |
| 7,704,269 B2 | 4/2010 | St. Goar et al. |
| 7,704,277 B2 | 4/2010 | Zakay et al. |
| 7,736,388 B2 | 6/2010 | Goldfarb et al. |
| 7,740,638 B2 | 6/2010 | Hyde |
| 7,744,609 B2 | 6/2010 | Allen et al. |
| 7,753,923 B2 | 7/2010 | St. Goar et al. |
| 7,758,491 B2 | 7/2010 | Buckner et al. |
| 7,758,595 B2 | 7/2010 | Allen et al. |
| 7,776,084 B2 | 8/2010 | Johnson |
| 7,785,366 B2 | 8/2010 | Maurer et al. |
| 7,799,038 B2 | 9/2010 | Sogard et al. |
| 7,803,187 B2 | 9/2010 | Hauser |
| 7,819,915 B2 | 10/2010 | Stobie et al. |
| 7,846,203 B2 | 12/2010 | Cribier |
| 7,887,552 B2 | 2/2011 | Bachman |
| 7,901,454 B2 | 3/2011 | Kapadia et al. |
| 7,909,866 B2 | 3/2011 | Stobie |
| 7,914,576 B2 | 3/2011 | Navia et al. |
| 7,927,370 B2 | 4/2011 | Webler et al. |
| 7,935,144 B2 | 5/2011 | Robin et al. |
| 7,935,145 B2 | 5/2011 | Alfieri et al. |
| 7,938,827 B2 | 5/2011 | Hauck et al. |
| 7,942,928 B2 | 5/2011 | Webler et al. |
| 7,951,195 B2 | 5/2011 | Antonsson et al. |
| 7,951,196 B2 | 5/2011 | McCarthy |
| 7,955,385 B2 | 6/2011 | Crittenden |
| 7,959,673 B2 | 6/2011 | Carpentier et al. |
| 7,981,139 B2 | 7/2011 | Martin et al. |
| 7,988,725 B2 | 8/2011 | Gross et al. |
| 7,993,396 B2 | 8/2011 | McCarthy |
| 7,998,151 B2 | 8/2011 | St. Goar et al. |
| 8,012,201 B2 | 9/2011 | Lashinski et al. |
| 8,012,202 B2 | 9/2011 | Alameddine |
| 8,016,882 B2 | 9/2011 | Macoviak et al. |
| 8,029,518 B2 | 10/2011 | Goldfarb et al. |
| 8,052,751 B2 | 11/2011 | Aklog et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,092,525 B2 | 1/2012 | Eliasen et al. |
| 8,118,866 B2 | 2/2012 | Herrmann et al. |
| 8,128,691 B2 | 3/2012 | Keranen |
| 8,133,272 B2 | 3/2012 | Hyde |
| 8,142,494 B2 | 3/2012 | Rahdert et al. |
| 8,142,495 B2 | 3/2012 | Hasenkam et al. |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,207 B2 | 5/2012 | Machold et al. |
| 8,187,299 B2 | 5/2012 | Goldfarb et al. |
| 8,187,323 B2 | 5/2012 | Mortier et al. |
| 8,204,605 B2 | 6/2012 | Hastings et al. |
| 8,206,439 B2 | 6/2012 | Gomez Duran |
| 8,216,230 B2 | 7/2012 | Hauck et al. |
| 8,216,256 B2 | 7/2012 | Raschdorf, Jr. et al. |
| 8,216,302 B2 | 7/2012 | Wilson et al. |
| 8,216,303 B2 | 7/2012 | Navia |
| 8,221,493 B2 | 7/2012 | Boyle et al. |
| 8,226,711 B2 | 7/2012 | Mortier et al. |
| 8,241,304 B2 | 8/2012 | Bachman |
| 8,241,351 B2 | 8/2012 | Cabiri |
| 8,252,050 B2 | 8/2012 | Maisano et al. |
| 8,252,051 B2 | 8/2012 | Chau et al. |
| 8,262,725 B2 | 9/2012 | Subramanian |
| 8,277,502 B2 | 10/2012 | Miller et al. |
| 8,287,591 B2 | 10/2012 | Keidar et al. |
| 8,292,884 B2 | 10/2012 | Levine et al. |
| 8,308,796 B2 | 11/2012 | Lashinski et al. |
| 8,323,336 B2 | 12/2012 | Hill et al. |
| 8,337,390 B2 | 12/2012 | Ferrazzi |
| 8,361,086 B2 | 1/2013 | Allen et al. |
| 8,377,118 B2 | 2/2013 | Lashinski et al. |
| 8,382,828 B2 | 2/2013 | Roberts |
| 8,382,829 B1 | 2/2013 | Call et al. |
| RE44,075 E | 3/2013 | Williamson et al. |
| 8,398,708 B2 | 3/2013 | Meiri et al. |
| 8,408,214 B2 | 4/2013 | Spenser |
| 8,413,573 B2 | 4/2013 | Rebecchi |
| 8,414,644 B2 | 4/2013 | Quadri et al. |
| 8,449,606 B2 | 5/2013 | Eliasen et al. |
| 8,657,872 B2 | 2/2014 | Seguin |
| 8,845,717 B2 | 9/2014 | Khairkhahan et al. |
| 8,888,843 B2 | 11/2014 | Khairkhahan et al. |
| 2001/0007956 A1 | 7/2001 | Letac et al. |
| 2001/0021872 A1 | 9/2001 | Bailey et al. |
| 2002/0029080 A1 | 3/2002 | Mortier et al. |
| 2002/0058995 A1 | 5/2002 | Stevens |
| 2002/0116024 A1 | 8/2002 | Goldberg et al. |
| 2002/0138135 A1 | 9/2002 | Duerig |
| 2003/0135263 A1 | 7/2003 | Rourke et al. |
| 2003/0199975 A1 | 10/2003 | Gabbay |
| 2004/0088047 A1 | 5/2004 | Spence et al. |
| 2004/0143323 A1 | 7/2004 | Chawla |
| 2005/0004665 A1 | 1/2005 | Aklog |
| 2005/0004668 A1 | 1/2005 | Aklog et al. |
| 2005/0096740 A1 | 5/2005 | Langberg et al. |
| 2005/0107871 A1 | 5/2005 | Realyvasquez et al. |
| 2005/0159810 A1 | 7/2005 | Filsoufi |
| 2005/0228495 A1 | 10/2005 | Macoviak |
| 2005/0283232 A1 | 12/2005 | Gabbay |
| 2006/0252984 A1 | 11/2006 | Rahdert et al. |
| 2007/0112425 A1 | 5/2007 | Schaller et al. |
| 2007/0129758 A1 | 6/2007 | Saadat |
| 2007/0233239 A1 | 10/2007 | Navia et al. |
| 2007/0239272 A1 | 10/2007 | Navia et al. |
| 2007/0255399 A1 | 11/2007 | Eliasen et al. |
| 2007/0265700 A1 | 11/2007 | Eliasen et al. |
| 2007/0265702 A1 | 11/2007 | Lattouf |
| 2008/0109075 A1 | 5/2008 | Keranen |
| 2008/0319541 A1 | 12/2008 | Filsoufi |
| 2009/0012354 A1 | 1/2009 | Wood |
| 2009/0088836 A1 | 4/2009 | Bishop et al. |
| 2009/0177277 A1 | 7/2009 | Milo |
| 2009/0234404 A1 | 9/2009 | Fitzgerald et al. |
| 2009/0259304 A1 | 10/2009 | O'Beirne et al. |
| 2009/0326648 A1 | 12/2009 | Machold et al. |
| 2010/0121435 A1 | 5/2010 | Subramanian et al. |
| 2010/0249947 A1 | 9/2010 | Lesh et al. |
| 2010/0262233 A1 | 10/2010 | He |
| 2010/0280606 A1 | 11/2010 | Naor |
| 2010/0298929 A1 | 11/2010 | Thornton et al. |
| 2010/0312333 A1 | 12/2010 | Navia et al. |
| 2011/0004299 A1 | 1/2011 | Navia et al. |
| 2011/0106247 A1 | 5/2011 | Miller et al. |
| 2011/0137397 A1 | 6/2011 | Chau et al. |
| 2012/0078360 A1 | 3/2012 | Rafiee |
| 2012/0197388 A1 | 8/2012 | Khairkhahan et al. |
| 2012/0323316 A1 | 12/2012 | Chau et al. |
| 2013/0023985 A1 | 1/2013 | Khairkhahan et al. |
| 2013/0282028 A1 | 10/2013 | Conklin et al. |
| 2013/0338763 A1 | 12/2013 | Rowe et al. |
| 2014/0128965 A1 | 5/2014 | Rafiee |
| 2015/0100116 A1 | 4/2015 | Mohl et al. |
| 2015/0112429 A1 | 4/2015 | Khairkhahan et al. |
| 2015/0119981 A1 | 4/2015 | Khairkhahan et al. |
| 2015/0164637 A1 | 6/2015 | Khairkhahan et al. |
| 2015/0366556 A1 | 12/2015 | Khairkhahan et al. |
| 2015/0366666 A1 | 12/2015 | Khairkhahan et al. |

FOREIGN PATENT DOCUMENTS

| | | |
|---|---|---|
| CN | 101947146 | 1/2011 |
| EP | 1 796 597 | 1/2013 |
| JP | 2005-535384 | 11/2005 |
| WO | WO 2004/014258 | 2/2004 |

(56) References Cited

FOREIGN PATENT DOCUMENTS

| WO | WO 2005/069875 | 8/2005 |
|---|---|---|
| WO | WO 2006/032051 | 3/2006 |
| WO | WO 2006/041877 | 4/2006 |
| WO | WO 2007/135101 | 11/2007 |
| WO | WO 2007/140470 | 12/2007 |
| WO | WO 2008/141322 | 11/2008 |
| WO | WO 2011/037891 | 3/2011 |
| WO | WO 2011/047168 | 4/2011 |
| WO | WO 2012/061809 | 5/2012 |
| WO | WO 2012/102928 | 8/2012 |
| WO | WO 2013/131069 | 9/2013 |
| WO | WO 2013/192107 | 12/2013 |
| WO | WO 2015/020971 | 2/2015 |
| WO | WO 2015/052570 | 4/2015 |
| WO | WO 2015/061533 | 4/2015 |
| WO | WO 2015/195823 | 12/2015 |
| WO | WO 2015/200497 | 12/2015 |

OTHER PUBLICATIONS

Biocina, *The arteficial coaptation surface concept in mitral valve repair*, University of Zagreb School of Medicine, Department of Cardiac Surgery, Savudrija Mitrofast 2010.
Chiam et al., *Percutaneous Transcatheter Mitral Valve Repair*, The American College of Cardiology Foundation, JACC: Cardiovascular Interventions, vol. 4 No. 1, Jan. 2011:1-13.
Jassar et al., *Posterior Leaflet Augmentation in Ischemic Mitral Regurgitation Increases Leaflet Coaptation and Mobility*, The Society of Thoracic Surgeons, Ann Thorac Surg 2012; 94:1438-45.
Langer et al., *Posterior mitral leaflet extension: An adjunctive repair option for ischemic mitral regurgitation?*, Surgery for Acquired Cardiovascular Disease, The Journal of Thoracic and Cardiovascular Surgery, Apr. 2006, downloaded Jun. 18, 2011.
Mohl et al., *An Innovative Concept for Transcatheter Treatment of Annular Dilatation and Restrictive Leaflet Motion in Mitral Insufficiency*, Medical University of Vienna, 1 page.
Mohl et al., *The Angel Valve Concept*, Vienna University of Technology, Medical University of Vienna, Technology Offer, 1 page.
Piemonte et al., *Cardiovascular™: The Mitral Valve Spacer*, Presented at Transcatheter Cardiovascular Therapeutics Conference—TCT Conference, Oct. 2008.
Rumel et al, *The Correction of Mitral Insufficiency with a Trans-Valvular Polyvinyl Formalinized Plastic (Ivalon) Sponge Prosthesis: A Preliminary Report*, American College of Chest Physicians, 1958;33;401-413, Dec. 2, 2010.
Extended European Search Report, EP 12738989.8, dated May 24, 2016.
Extended European Search Report, EP 13806272.4, dated Nov. 11, 2015.
International Preliminary Report on Patentability for PCT/US2012/021744 mailed Aug. 8, 2013 in 15 pages.
International Search Report for Application No. PCT/US2013/046173 dated Oct. 4, 2013 in 15 pages.
International Search Report for Application No. PCT/US2014/061901 dated Jan. 26, 2015 in 14 pages.
International Search Report for Application No. PCT/US2015/036260 dated Oct. 1, 2015 in 20 pages.
International Search Report for Application No. PCT/US2015/037451 dated Oct. 6, 2015 in 12 pages.
Office Action for CN 201280006673.7 dated Dec. 10, 2014.
Office Action for CN 201280006673.7 dated Sep. 22, 2015.
Office Action for CN 201380044122.4 dated Nov. 4, 2015.
Office Action for JP 2013-552015 dated Dec. 7, 2015.

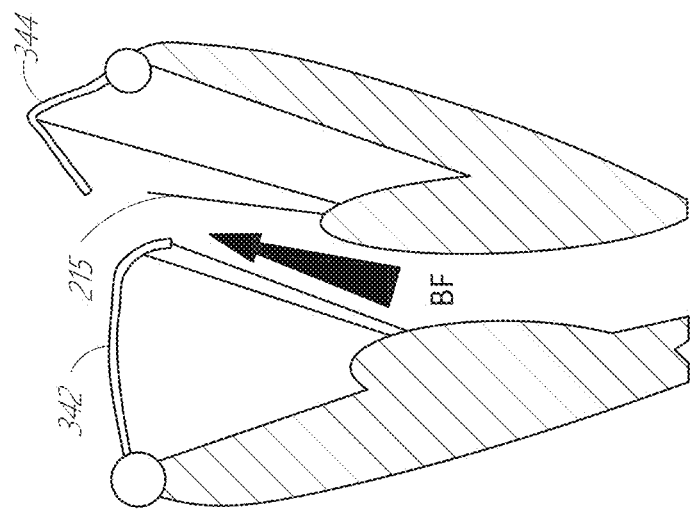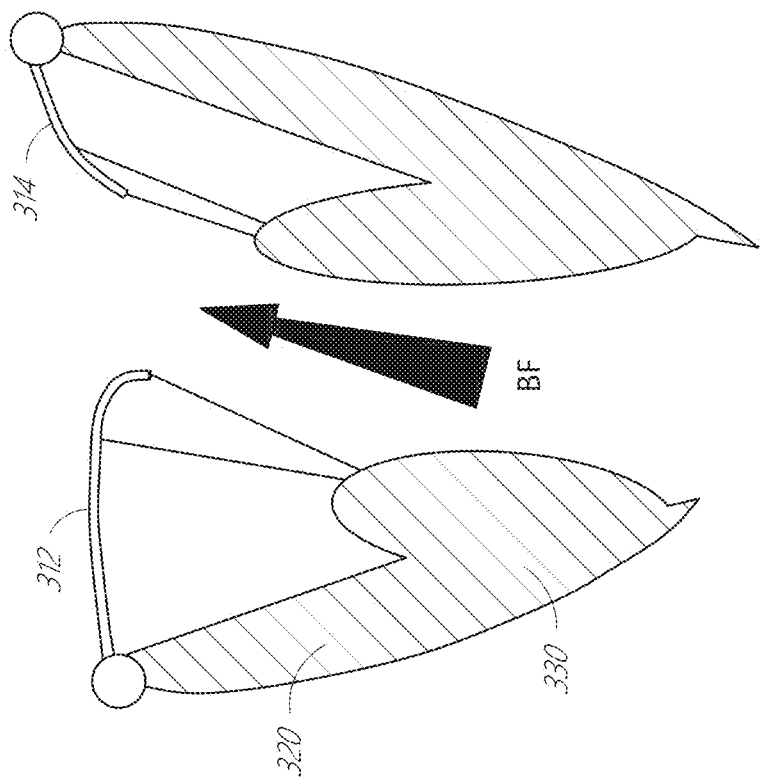
FIG. 4A
FIG. 4B

INITIAL IMPLANT ADVANCEMENT

PARTIAL IMPLANT OPENING & ADJUSTMENT

IMPLANT RECAPTURE

FULL IMPLANT OPENING - SECTIONED

SECONDARY ANCHOR PLACEMENT

DEVICE, SYSTEM, AND METHOD FOR TRANSCATHETER TREATMENT OF VALVULAR REGURGITATION

CROSS-REFERENCE TO RELATED APPLICATIONS

The present application claims priority under 35 U.S.C. §119(e) to U.S. Provisional Application No. 62/252,336, filed on Nov. 6, 2015, the disclosures of which is incorporated by reference herein in its entirety and made a part of the present specification.

BACKGROUND

Field

The present disclosure generally provides improved medical devices, systems, and methods, typically for treatment of heart valve disease and/or for altering characteristics of one or more valves of the body. Embodiments include implants for treatment of mitral valve regurgitation.

The human heart receives blood from the organs and tissues via the veins, pumps that blood through the lungs where the blood becomes enriched with oxygen, and propels the oxygenated blood out of the heart to the arteries so that the organ systems of the body can extract the oxygen for proper function. Deoxygenated blood flows back to the heart where it is once again pumped to the lungs.

The heart includes four chambers: the right atrium (RA), the right ventricle (RV), the left atrium (LA) and the left ventricle (LV). The pumping action of the left and right sides of the heart occurs generally in synchrony during the overall cardiac cycle.

The heart has four valves generally configured to selectively transmit blood flow in the correct direction during the cardiac cycle. The valves that separate the atria from the ventricles are referred to as the atrioventricular (or AV) valves. The AV valve between the left atrium and the left ventricle is the mitral valve. The AV valve between the right atrium and the right ventricle is the tricuspid valve. The pulmonary valve directs blood flow to the pulmonary artery and thence to the lungs; blood returns to the left atrium via the pulmonary veins. The aortic valve directs flow through the aorta and thence to the periphery. There are normally no direct connections between the ventricles or between the atria.

The mechanical heartbeat is triggered by an electrical impulse, which spreads throughout the cardiac tissue. Opening and closing of heart valves may occur primarily as a result of pressure differences between chambers, those pressures resulting from either passive filling or chamber contraction. For example, the opening and closing of the mitral valve may occur as a result of the pressure differences between the left atrium and the left ventricle.

At the beginning of ventricular filling (diastole) the aortic and pulmonary valves are closed to prevent back flow from the arteries into the ventricles. Shortly thereafter, the AV valves open to allow unimpeded flow from the atria into the corresponding ventricles. Shortly after ventricular systole (i.e., ventricular emptying) begins, the tricuspid and mitral valves normally shut, forming a seal, which prevents flow from the ventricles back into the corresponding atria.

Unfortunately, the AV valves may become damaged or may otherwise fail to function properly, resulting in improper closing. The AV valves are complex structures that generally include an annulus, leaflets, chordae and a support structure. Each atrium interfaces with its valve via an atrial vestibule. The mitral valve has two leaflets; the analogous structure of the tricuspid valve has three leaflets, and apposition or engagement of corresponding surfaces of leaflets against each other helps provide closure or sealing of the valve to prevent blood flowing in the wrong direction. Failure of the leaflets to seal during ventricular systole is known as malcoaptation, and may allow blood to flow backward through the valve (regurgitation). Heart valve regurgitation can have serious consequences to a patient, often resulting in cardiac failure, decreased blood flow, lower blood pressure, and/or a diminished flow of oxygen to the tissues of the body. Mitral regurgitation can also cause blood to flow back from the left atrium to the pulmonary veins, causing congestion. Severe valvular regurgitation, if untreated, can result in permanent disability or death.

Description of the Related Art

A variety of therapies have been applied for treatment of mitral valve regurgitation, and still other therapies may have been proposed but not yet actually used to treat patients. While several of the known therapies have been found to provide benefits for at least some patients, still further options would be desirable. For example, pharmacologic agents (such as diuretics and vasodilators) can be used with patients having mild mitral valve regurgitation to help reduce the amount of blood flowing back into the left atrium. However, medications can suffer from lack of patient compliance. A significant number of patients may occasionally (or even regularly) fail to take medications, despite the potential seriousness of chronic and/or progressively deteriorating mitral valve regurgitation. Pharmacological therapies of mitral valve regurgitation may also be inconvenient, are often ineffective (especially as the condition worsens), and can be associated with significant side effects (such as low blood pressure).

A variety of surgical options have also been proposed and/or employed for treatment of mitral valve regurgitation. For example, open-heart surgery can replace or repair a dysfunctional mitral valve. In annuloplasty ring repair, the posterior mitral annulus can be reduced in size along its circumference, optionally using sutures passed through a mechanical surgical annuloplasty sewing ring to provide coaptation. Open surgery might also seek to reshape the leaflets and/or otherwise modify the support structure. Regardless, open mitral valve surgery is generally a very invasive treatment carried out with the patient under general anesthesia while on a heart-lung machine and with the chest cut open. Complications can be common, and in light of the morbidity (and potentially mortality) of open-heart surgery, the timing becomes a challenge—sicker patients may be in greater need of the surgery, but less able to withstand the surgery. Successful open mitral valve surgical outcomes can also be quite dependent on surgical skill and experience.

Given the morbidity and mortality of open-heart surgery, innovators have sought less invasive surgical therapies. Procedures that are done with robots or through endoscopes are often still quite invasive, and can also be time consuming, expensive, and in at least some cases, quite dependent on the operator's skill. Imposing even less trauma on these sometimes frail patients would be desirable, as would be providing therapies that could be successfully implemented by a significant number of physicians using widely distributed skills. Toward that end, a number of purportedly less invasive technologies and approaches have been proposed. These include devices which seek to re-shape the mitral annulus from within the coronary sinus; devices that attempt to reshape the annulus by cinching either above to below the native annulus; devices to fuse the leaflets (imitating the Alfieri stitch); devices to re-shape the left ventricle, and the like.

Perhaps most widely known, a variety of mitral valve replacement implants have been developed, with these implants generally replacing (or displacing) the native leaflets and relying on surgically implanted structures to control the blood flow paths between the chambers of the heart. While these various approaches and tools have met with differing levels of acceptance, none has yet gained widespread recognition as an ideal therapy for most or all patients suffering from mitral valve regurgitation.

Because of the challenges and disadvantages of known minimally invasive mitral valve regurgitation therapies and implants, still further alternative treatments have been proposed. Some of the alternative proposals have called for an implanted structure to remain within the valve annulus throughout the heart beat cycle. One group of these proposals includes a cylindrical balloon or the like to remain implanted on a tether or rigid rod extending between the atrium and the ventricle through the valve opening. Another group relies on an arcuate ring structure or the like, often in combination with a buttress or structural cross-member extending across the valve so as to anchor the implant. Unfortunately, sealing between the native leaflets and the full perimeter of a balloon or other coaxial body may prove challenging, while the significant contraction around the native valve annulus during each heart beat may result in significant fatigue failure issues during long-term implantation if a buttress or anchor interconnecting cross member is allowed to flex. Moreover, the significant movement of the tissues of the valve may make accurate positioning of the implant challenging regardless of whether the implant is rigid or flexible.

In light of the above, it would be desirable to provide improved medical devices, systems, and methods. It would be particularly desirable to provide new techniques for treatment of mitral valve regurgitation and other heart valve diseases, and/or for altering characteristics of one or more of the other valves of the body. The need remains for a device which can directly enhance leaflet coaptation (rather than indirectly via annular or ventricular re-shaping) and which does not disrupt leaflet anatomy via fusion or otherwise, but which can be deployed simply and reliably, and without excessive cost or surgical time. It would be particularly beneficial if these new techniques could be implemented using a less-invasive approach, without stopping the heart or relying on a heart-lung machine for deployment, and without relying on exceptional skills of the operator to provide improved valve and/or heart function.

SUMMARY

The disclosure generally provides improved medical devices, systems, and methods. New coaptation assistance elements, systems, and methods for treatment of mitral valve regurgitation and other valve diseases are disclosed. The coaptation assistance element may remain within the blood flow path as the valve moves back and forth between an open-valve configuration and a closed valve configuration. The coaptation assistance elements may be relatively thin, elongate (along the blood flow path), and/or conformable structures which extend laterally across some, most, or all of the width of the valve opening, allowing coaptation between at least one of the native leaflets and the coaptation assistance element. The devices described herein can be used with any valve of the human body, including valves with two leaflets or three leaflets.

In some embodiments, an advantage is the ability to retrieve the coaptation assistance element. In some embodiments, the coaptation assistance element has a single anchor, which can engage or disengage tissue. In some embodiments, the anchor is captive within an annular hub of the coaptation assistance element. In some embodiments, the captive anchor is removed simultaneously with the removal of the coaptation assistance element. In some embodiments, the coaptation assistance element can include secondary anchors. In some embodiments, the coaptation assistance element can include passive anchors. In some embodiments, engagement of the anchor with the tissue positions one or more passive anchors into engagement with tissue. In some embodiments, an advantage is to retrieve the coaptation assistance element during a procedure. In some embodiments, the coaptation assistance element can be repositioned during a surgical procedure. In some embodiments, the coaptation assistance element can be removed from the patient during a subsequent surgical procedure. In some embodiments, the coaptation assistance element can be replaced by another device during a subsequent surgical procedure. In some embodiments, a single annular anchor facilitates the ability to retrieve the coaptation assistance element. In some embodiments, the location of the annular anchor facilitates the ability to retrieve the coaptation assistance element. In some embodiments, the ability to collapse the coaptation assistance element with the purse-string suture as described herein facilitates the ability to retrieve the coaptation assistance element.

In some embodiments, an advantage is the connection between the coaptation assistance element and the delivery catheter. In some embodiments, the coaptation assistance element includes an annular hub with features to engage the delivery catheter. In some embodiments, the coaptation assistance element and the delivery catheter are removably coupled such that the coaptation assistance element can be released from the delivery catheter during a procedure. In some embodiments, one or more secondary structures couples the coaptation assistance element and the delivery catheter after the coaptation assistance element is released from the delivery catheter. In some embodiments, the one or more secondary structures include the purse-string suture as descried herein. In some embodiments, the one or more secondary structures facilitate the collapse and/or expansion of the coaptation assistance element. In some embodiments, the coaptation assistance element and the delivery catheter are rotationally fixed relative to each other when coupled. In some embodiments, relative motion of the delivery catheter causes motion of the coaptation assistance element.

In some embodiments, an advantage is the coaptation assistance element can be delivered with a hub-leading orientation. In some methods of use, the annular hub can be moved into position relative to the anatomical structures. In some methods of use, the ventricular end of the coaptation assistance element can be retained within the delivery catheter until the annular hub is positioned. In some methods of use, once the annular hub and/or the annular anchor are engaged with the tissue, the coaptation assistance element can be expanded. In some methods of use, once the annular hub and/or the annular anchor are engaged with the tissue, the ventricular end of the coaptation assistance element can be positioned.

In some embodiments, an advantage is the coaptation assistance element can be delivered with a strut-leading orientation. In this method of use, one or more of the struts of the coaptation assistance element can be moved into position relative to the anatomical structures prior to the positioning of the annular hub. In some methods of use, the coaptation assistance element can be expanded or partially expanded prior to the engagement of the annular anchor. In some methods of use, the annular hub can be retained within the delivery catheter until one or more of the struts are positioned. In some methods of use, once the struts are positioned, the annular anchor can be engaged with the tissue.

In some embodiments, an advantage is the annular anchor can be rotated independently of the coaptation assistance element. As described herein, the coaptation assistance element is coupled to one portion of the delivery catheter. As described herein, the annular anchor is independently coupled to another portion of the delivery catheter, such as a driver disposed with the delivery catheter. The annular anchor can be rotated independently of the annular hub. The annular hub can remain stationary as the annular anchor is rotated to engage tissue. The annular anchor can be driven into the tissue while the delivery catheter retains the position of the annular hub.

In some embodiments, an advantage is the ability to collapse the coaptation assistance element. In some embodiments, the coaptation assistance element is fully collapsed. The fully collapsed configuration can be the insertion configuration or a low profile configuration. In some embodiments, the coaptation assistance element is partially collapsed. The partially collapsed configuration can be a partially deployed configuration. The partially collapsed configuration can allow the coaptation assistance element to be selectively deployed within the heart. The partially collapsed configuration can allow the coaptation assistance element to be moved into position within the heart. The configurations of the coaptation assistance element can be monitored such as by imaging to ensure proper deployment. In some embodiments, one or more purse-string sutures, or portions thereof, are tensioned to collapse or partially collapse the coaptation assistance element. In some embodiments, the partially collapsed configuration can allow rotation of the coaptation assistance element. In some embodiments, the fully collapsed configuration can allow rotation of the coaptation assistance element. In some embodiments, the coaptation assistance element can be rotated with a delivery catheter or portion thereof. In some embodiments, the coaptation assistance element can be rotated about a central location such as the annular hub.

In some embodiments, an advantage is the ability to expand the coaptation assistance element. In some embodiments, one or more purse-string sutures, or portions thereof, are released to expand the coaptation assistance element. In some embodiments, release of the purse-string suture allows one or more struts to assume a neutral configuration. In some embodiments, the release of the purse-string suture allows one or more struts to assume a pre-shaped curve. In some embodiments, the one or more struts comprise NiTi. In some embodiments, the purse-string suture can be repeatedly tensioned and/or released. In some embodiments, the purse-string suture is captive within the coaptation assistance element. In some embodiments, the purse-string suture is tensioned to remove the coaptation assistance element from a patient. In some embodiments, the purse-string suture is released to deploy the coaptation assistance element within the heart of a patient. In some embodiments, the purse-string suture can be selective deployed to expand a portion of coaptation assistance element while another portion of the coaptation assistance element remains collapsed or partially collapsed.

In some embodiments, an advantage is the ability to adjust the coaptation assistance element. In some embodiments, the coaptation assistance element can be held by a central location. In some embodiments, the central location is the anchor. In some embodiments, the central location is the hub. In some embodiments, the hub and/or the anchor are located generally near a mid-point of the diameter of the coaptation assistance element. In some embodiments, the hub and/or the anchor are generally located near a mid-point and/or central location of the annular portion of the coaptation assistance element. In some embodiments, the coaptation assistance element can be held at a neutral position. In some embodiments, the coaptation assistance element can be rotated by rotating a delivery catheter connected to the annular hub. In some embodiments, the coaptation assistance element can be moved longitudinally by corresponding longitudinal motion of a delivery catheter connected to the annular hub.

In some embodiments, an advantage is the coaptation assistance element can be retained by a delivery catheter after the coaptation assistance element is positioned. In some embodiments, the coaptation assistance element can be fully deployed within the mitral valve but still tethered to a delivery catheter. In some embodiments, the coaptation assistance element can be adjusted after the coaptation assistance element is fully deployed within the mitral valve. In some embodiments, the coaptation assistance element can be rotated about the hub after the coaptation assistance element is fully deployed. In some embodiments, the anchor can be disengaged and/or reengaged with the tissue after the coaptation assistance element is fully deployed. In some embodiments, the purse-string sutures can collapse and/or expand the coaptation assistance element or a portion thereof after the coaptation assistance element is fully deployed. In some embodiments, the coaptation assistance element can be recaptured after the coaptation assistance element is fully deployed. In some embodiments, the coaptation assistance element can be removed after the coaptation assistance element is fully deployed.

In some embodiments, an advantage is the coaptation assistance element does not require ventricular attachment. In some embodiments, the coaptation assistance element only requires annular attachment. In some embodiments, the coaptation assistance element only requires attachment of an annular anchor through an annular hub. In some embodiments, the coaptation assistance element only requires attachment of an annular anchor through an annular hub and annular barbs. In some embodiments, the coaptation assistance element only requires attachment of an annular anchor through an annular hub, annular barbs, and/or commissural barbs.

In some embodiments, an advantage is the radially extending frame. In some embodiments, the frame comprises an annular hub and one or more struts. In some embodiments, the struts extend radially from the annular hub. In some embodiments, the frame is constructed from a single, planar sheet of material. In some embodiments, the frame is precisely cut using water jet, laser etching or similar technology. In some embodiments, the frame is constructed by forming the annular hub with an edge of the frame. In some embodiments, the planar sheet of material is formed into a loop which becomes the annular hub. In some embodiments, the struts are bent to the desired configuration. In some embodiments, the struts are equally spaced about the circumference of the annular hub. In some embodiments, the struts are unequally spaced about the circumference of the annular hub. In some embodiments, the struts extending along a portion of the circumference of the annular hub are different than struts extending along another portion of the circumference of the annular hub. In some embodiments, one or more designated portions of the struts are designed to be placed near the annular region of the heart. In some embodiments, one or more designated portions of the struts are designed to be placed near the commissure region of the heart. In some embodiments, one or more designated portions of the struts are designed to be placed near the ventricular region of the heart. In some embodiments, the struts of the radially outward frame do not intersect. In some embodiments, the struts of the radially outward frame do not form a mesh. In some embodiments, the struts of the radially outward frame extend in a line from the hub to an edge of the coaptation assistance element. In some embodiments, the struts of the radially outward frame have a sharpened edge. In some embodiments, the sharpened edge extends in a straight line from the edge of the coaptation assistance element. In some embodiments, the sharpened edge is integrally formed in the strut. In some embodiments, a strut of the radially outward frame has one, two, or more radii of curvature. In some embodiments, a strut of the radially outward frame can be concave or convex or both concave and convex along the length of the strut. In some embodiments, a strut of the radially outward frame has one or more inflection points.

In some embodiments, an advantage is the curvature of the frame. In some embodiments, the annular hub is radially extending. In some embodiments, the annular hub extends from the coaptation assistance element away from the annulus. In some embodiments, the annular hub extends from a surface of the coaptation assistance element above a planar surface of the struts. In some embodiments, an edge of the coaptation assistance element is curved. In some embodiments, one or more struts may curve laterally from the annular hub toward the superior edge. In some embodiments, the superior edge of the coaptation assistance element can curve upward from the annulus. In some embodiments, the superior edge of the coaptation assistance element can curve upward from the posterior leaflet. In some embodiments, the superior edge of the coaptation assistance element can curve downward toward the annulus. In some embodiments, the superior edge of the coaptation assistance element can curve downward toward the posterior leaflet. In some embodiments, one or more struts may curve laterally from the annular hub toward the inferior edge. In some embodiments, the inferior edge of the coaptation assistance element can curve away from the posterior leaflet. In some embodiments, the inferior edge of the coaptation assistance element can curve toward the posterior leaflet.

In some embodiments, a coaptation assistance element for treating mal-coaptation of a heart valve in provided. The heart valve has an annulus. The coaptation assistance element can include a body that includes an annular section and a coaptation section. In some embodiments, the annular section is configured to be implanted within a heart superior to a valve annulus. In some embodiments, the coaptation zone configured to be implanted within a heart and traversing a plane of the valve annulus. The coaptation assistance element can include a first coaptation surface, and an opposed second surface. In some embodiments, each surface is bounded by a first lateral edge, a second lateral edge, an inferior edge, and a superior edge. In some embodiments, the superior edge forms a lip and cupped downward toward the inferior edge or upward from the annular section. The coaptation assistance element can include a hub and an anchor coupled to the hub and carried by the annular section. In some embodiments, the anchor is selectively deployable at a first target location. The coaptation assistance element can include a plurality of struts extending radially outward from the hub. In some embodiments, the plurality of struts comprise at least a first strut residing within the annular section and a second strut extending from the annular section to the coaptation section, wherein the second strut has a total length that is longer than that of the first strut, such as, for example, a total length that is about, or at least about 110%, 120%, 130%, 140%, 150%, 160%, 170%, 180%, 190%, 200%, 225%, 250% or more of the total length of the first strut. In some embodiments, the total length of the second strut is between about 125% and about 300%, or between about 125% and 200% of the total length of the first strut.

In some embodiments, at least one strut of the plurality of struts has a sharpened tip configured to engage tissue. In some embodiments, the plurality of struts comprises Nitinol. In some embodiments, the anchor is helical-shaped. The coaptation assistance element can include one or more additional anchors. In some embodiments, the one or more additional anchors are active anchors. In some embodiments, the hub comprises a cross-pin configured to extend through a helix of the anchor. In some embodiments, the hub is configured to mate with a delivery catheter, wherein the delivery catheter is configured to position the hub near the first target location. In some embodiments, the delivery catheter is configured to rotate the anchor independently of the hub. The coaptation assistance element can include a radiopaque marker. The coaptation assistance element can include a plurality of radiopaque markers near the superior edge. In some embodiments, the superior edge forming a lip is cupped downward toward the inferior edge. In some embodiments, the superior edge forming a lip is cupped upward from the annular section. In some embodiments, the hub extends upward from the annular section. In some embodiments, the inferior edge curves backwards toward the hub.

In some embodiments, a method for treating mal-coaptation of a heart valve in a patient is provided. The heart valve has an annulus. The annulus further defines a valve plane, the valve plane separating an atrium proximally and a ventricle distally. The method can include the step of coupling a delivery catheter to a hub of a coaptation assistance element. The method can include the step of positioning the hub near the annulus. The method can include the step of rotating an anchor through the hub and into heart tissue distal to the annulus. The method can include the step of expanding the coaptation assistance element by allowing a plurality of struts to expand radially outward from the hub.

In some embodiments, the coaptation assist body is suspended such that the coaptation surface coapts with a first leaflet and a leaflet surface of the coaptation assist body overlays a second leaflet such that mal-coaptation is mitigated. The method can include the step of engaging a sharpened end of a strut of the plurality of struts with heart tissue distal to the annulus. The method can include the step of monitoring the position of the coaptation assistance element with one or more markers. The method can include the step of monitoring the position of the coaptation assistance element with a plurality of markers near a superior edge of the coaptation assistance element. In some embodiments, a tip of the anchor is recessed in the hub during positioning the hub near the annulus.

BRIEF DESCRIPTION OF THE DRAWINGS

FIG. 4A illustrates a stylized cross section of a heart, showing mitral valve mal-coaptation in the setting of functional mitral valve regurgitation.

FIG. 4B illustrates a stylized cross section of a heart, showing mitral valve mal-coaptation in the setting of degenerative mitral valve regurgitation.

DETAILED DESCRIPTION

Figure 1A:
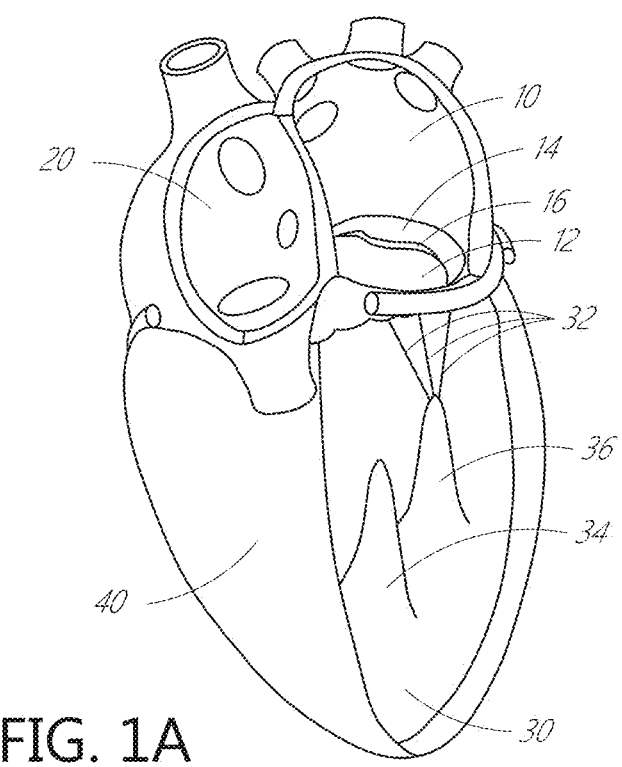
FIG. 1A-1F schematically illustrate some of the tissues of the heart and mitral valve, as described in the Background section and below, and which may interact with the implants and systems described herein.
Figure 1B:
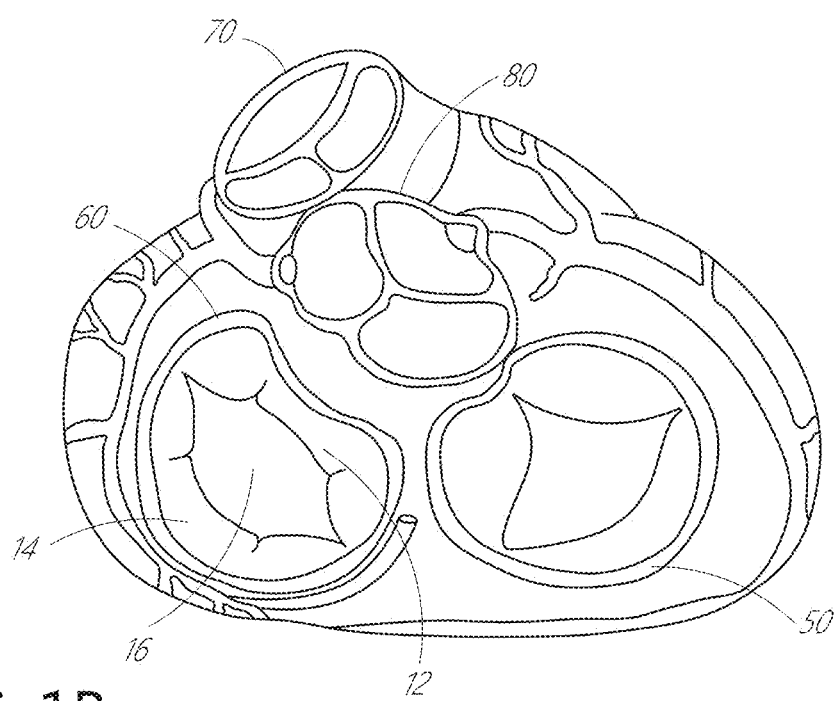
Figure 1C:
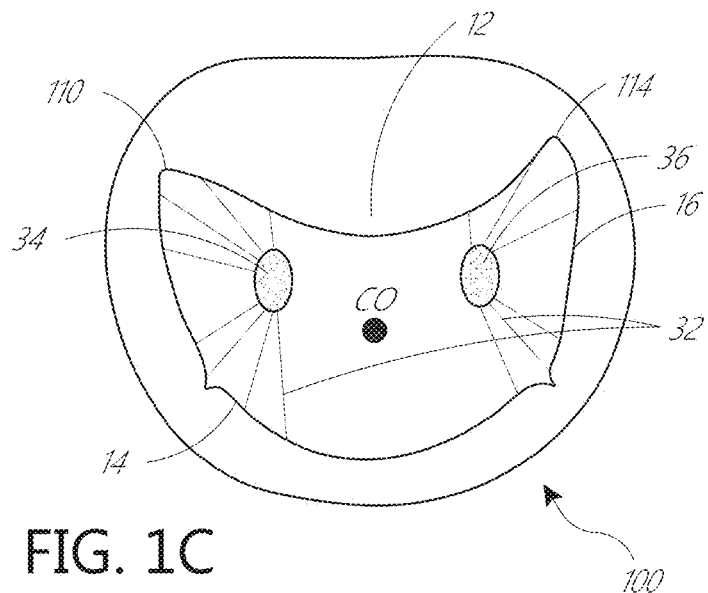
Figure 1D:
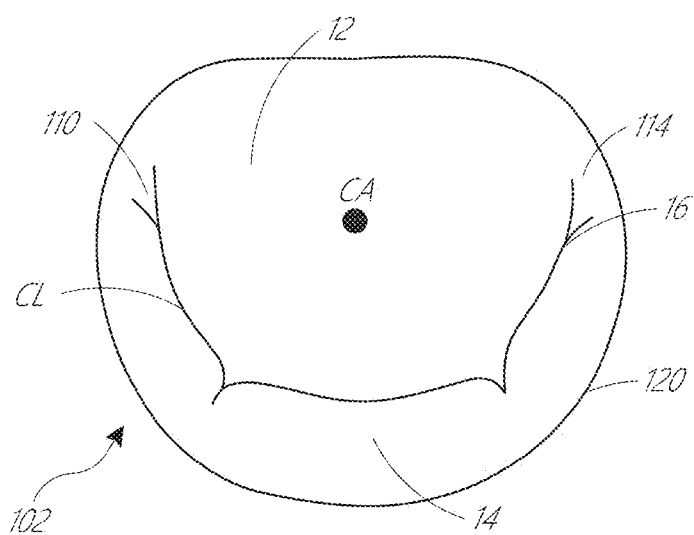

The present invention, in some embodiments, generally provides improved medical devices, systems, and methods, often for treatment of mitral valve regurgitation and other valve diseases including tricuspid regurgitation. While the description that follows includes reference to the anterior leaflet in a valve with two leaflets such as the mitral valve, it is understood that "anterior leaflet" could refer to one or more leaflets in valve with multiple leaflets. For example, the tricuspid valve has 3 leaflets so the "anterior" could refer to one or two of the medial, lateral, and posterior leaflets. The coaptation assistance elements described herein will generally include a coaptation assist body (sometimes referred to herein as a valve body) which is generally along the blood flow path as the leaflets of the valve move back and forth between an open-valve configuration (with the anterior leaflet separated from valve body) and a closed-valve configuration (with the anterior leaflet engaging opposed surfaces of the valve body). The valve body will be disposed between the native leaflets to close the gap caused by mal-coaptation of the native leaflets by providing a surface for at least one of the native leaflets to coapt against, while effectively replacing a second native leaflet in the area of the valve which, were it functioning normally, it would occlude during systole. The gaps may be lateral (such as may be caused by a dilated left ventricle and/or mitral valve annulus) and/or axial (such as where one leaflet prolapses or is pushed by fluid pressure beyond the annulus when the valve should close). In some embodiments, the coaptation assist elements may completely assist one, two, or more valve leaflets, or in some embodiments partially assist a valve leaflet, for example, covering only one or more of the A1, A2, and/or A3 scallops of the anterior leaflet, and/or one or more of the P1, P2, and/or P3 scallops of the posterior leaflet.

Among other uses, the coaptation assistance elements, and methods described herein may be configured for treating functional and/or degenerative mitral valve regurgitation (MR) by creating an artificial or new coaptation zone within which at least one of the native mitral valve leaflets can seal. The structures and methods herein will largely be tailored to this application, though alternative embodiments might be configured for use in other valves of the heart and/or body, including the tricuspid valve, valves of the peripheral vasculature, the inferior vena cava, or the like.

Referring to FIGS. 1A-1D, the four chambers of the heart are shown, the left atrium 10, right atrium 20, left ventricle 30, and right ventricle 40. The mitral valve 60 is disposed between the left atrium 10 and left ventricle 30. Also shown are the tricuspid valve 50 which separates the right atrium 20 and right ventricle 40, the aortic valve 80, and the pulmonary valve 70. The mitral valve 60 is composed of two leaflets, the anterior leaflet 12 and posterior leaflet 14. In a healthy heart, the two leaflets appose during systole at the coaptation zone 16.

Figure 1E:
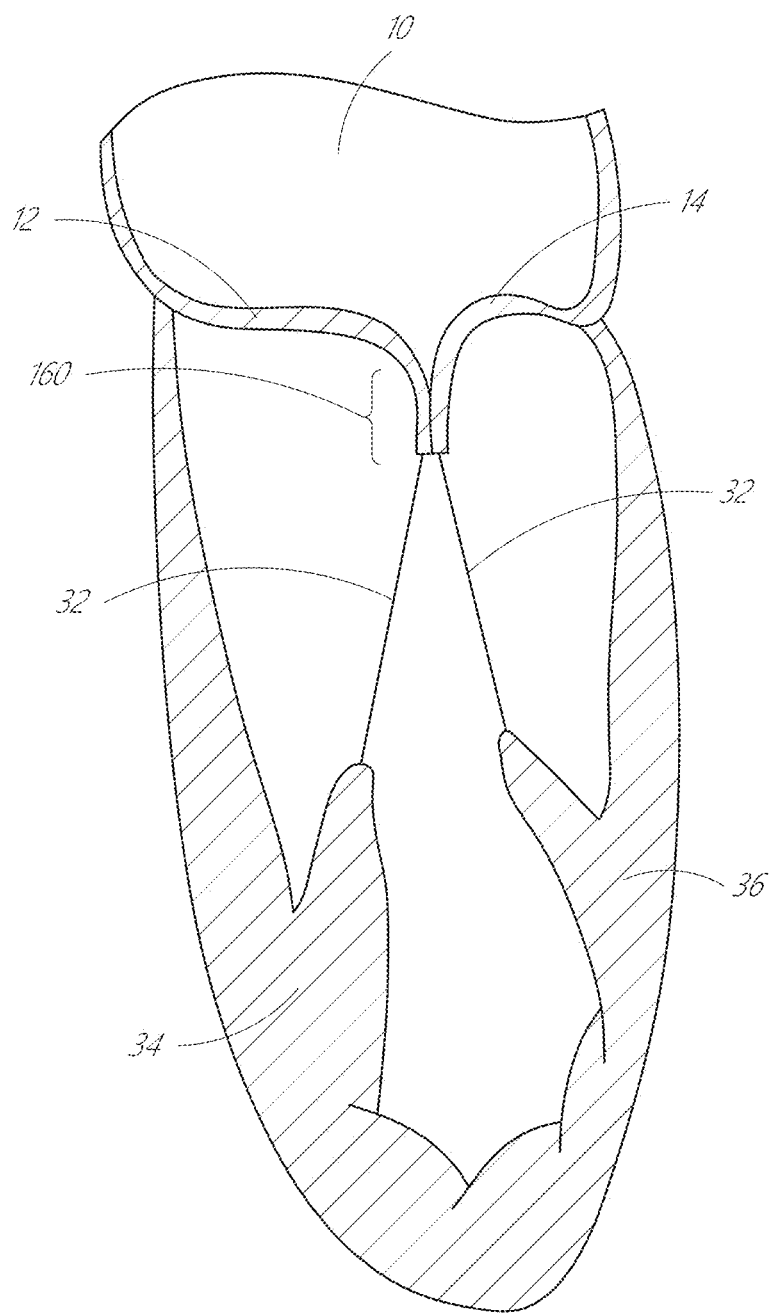

The fibrous annulus 120, part of the cardiac skeleton, provides attachment for the two leaflets of the mitral valve, referred to as the anterior leaflet 12 and the posterior leaflet 14. The leaflets are axially supported by attachment to the chordae tendinae 32. The chordae, in turn, attach to one or both of the papillary muscles 34, 36 of the left ventricle. In a healthy heart, the chordae support structures tether the mitral valve leaflets, allowing the leaflets to open easily during diastole but to resist the high pressure developed during ventricular systole. In addition to the tethering effect of the support structure, the shape and tissue consistency of the leaflets helps promote an effective seal or coaptation. The leading edges of the anterior and posterior leaflet come together along a funnel-shaped zone of coaptation 16, with a lateral cross-section 160 of the three-dimensional coaptation zone (CZ) being shown schematically in FIG. 1E.

Figure 1F:
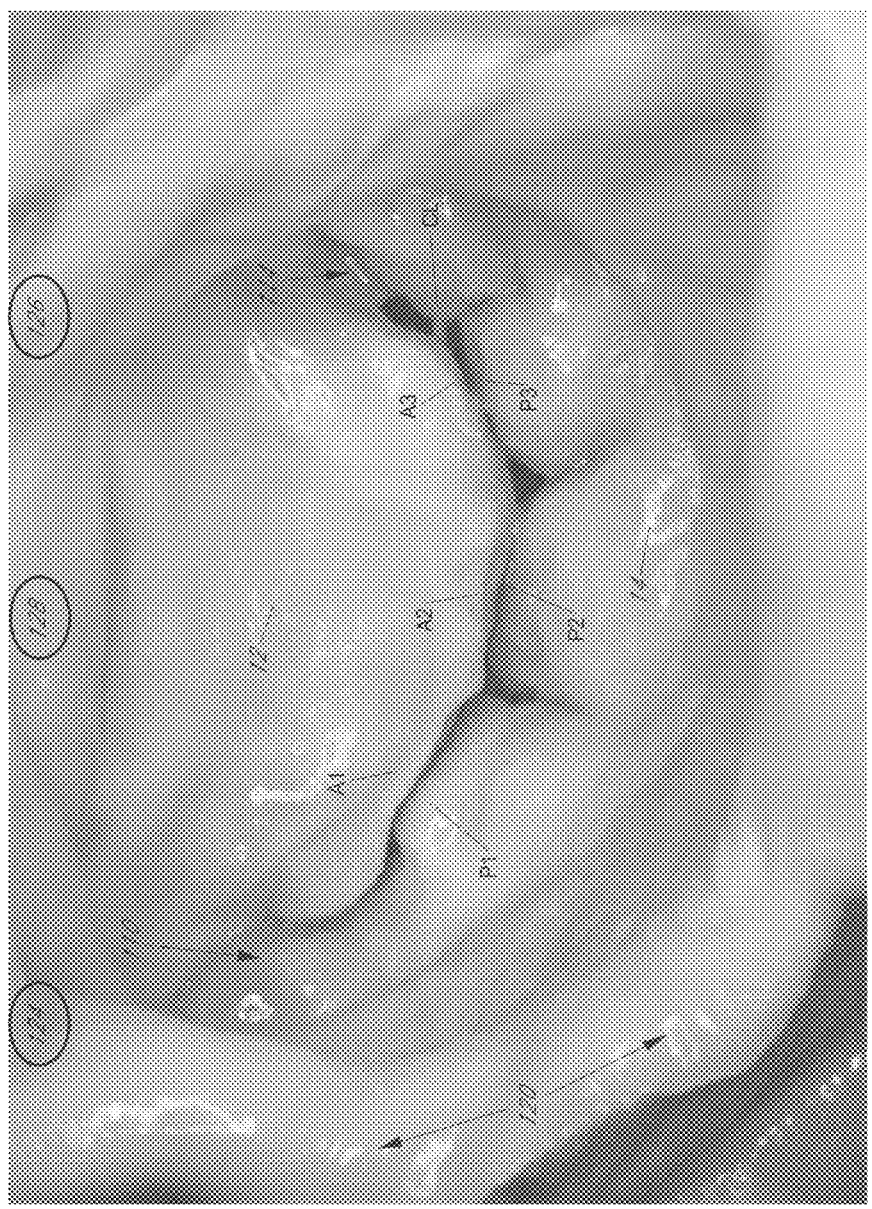

The anterior and posterior mitral leaflets are dissimilarly shaped. The anterior leaflet is more firmly attached to the annulus overlying the central fibrous body (cardiac skeleton), and is somewhat stiffer than the posterior leaflet, which is attached to the more mobile posterior mitral annulus. Approximately 80 percent of the closing area is the anterior leaflet. Adjacent to the commissures 110, 114, on or anterior to the annulus 120, lie the left (lateral) 124 and right (septal) 126 fibrous trigones which are formed where the mitral annulus is fused with the base of the non-coronary cusp of the aorta (FIG. 1F). The fibrous trigones 124, 126 form the septal and lateral extents of the central fibrous body 128. The fibrous trigones 124, 126 may have an advantage, in some embodiments, as providing a firm zone for stable engagement with one or more annular or atrial anchors. The coaptation zone CL between the leaflets 12, 14 is not a simple line, but rather a curved funnel-shaped surface interface. The first 110 (lateral or left) and second 114 (septal or right) commissures are where the anterior leaflet 12 meets the posterior leaflet 14 at the annulus 120. As seen most clearly in the axial views from the atrium of FIGS. 1C, 1D, and 1F, an axial cross-section of the coaptation zone generally shows the curved line CL that is separated from a centroid of the annulus CA as well as from the opening through the valve during diastole CO. In addition, the leaflet edges are scalloped, more so for the posterior versus the anterior leaflet. Mal-coaptation can occur between one or more of these A-P (anterior-posterior) segment pairs A1/P1, A2/P2, and A3/P3, so that mal-coaptation characteristics may vary along the curve of the coaptation zone CL.

Figure 2B:
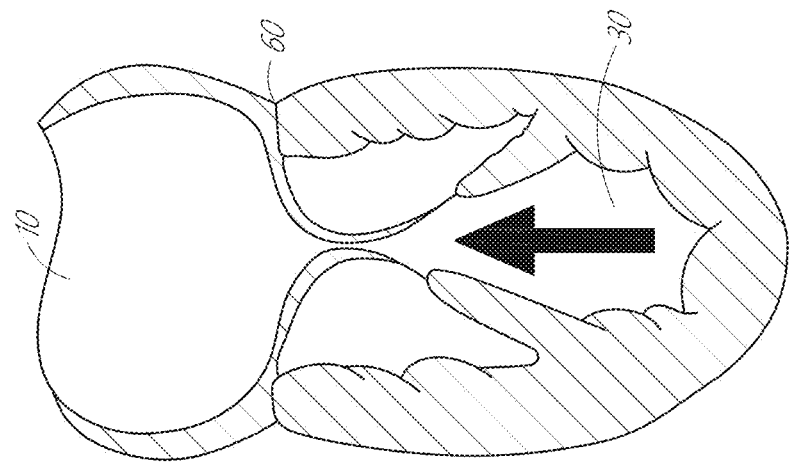
FIG. 2B illustrates a simplified cross-section of a heart, schematically showing mitral valve function during systole.
Figure 2A:
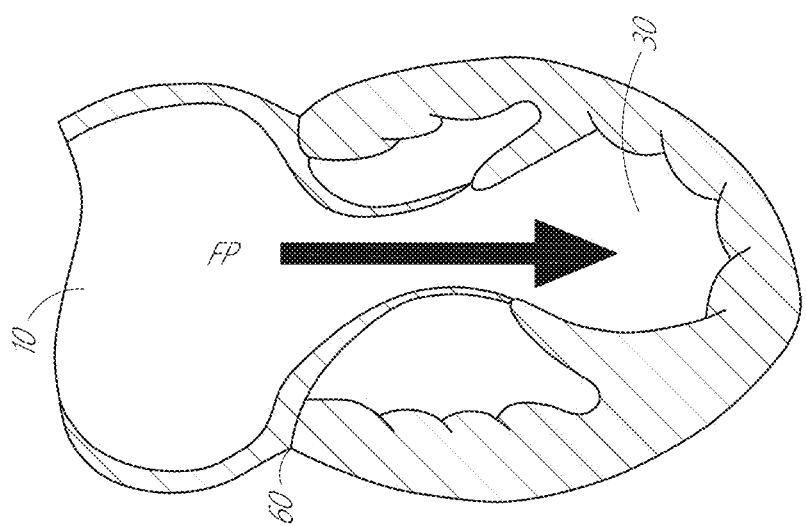
FIG. 2A illustrates a simplified cross-section of a heart, schematically showing mitral valve function during diastole.

Referring now to FIG. 2A, a properly functioning mitral valve 60 of a heart is open during diastole to allow blood to flow along a flow path FP from the left atrium toward the left ventricle 30 and thereby fill the left ventricle. As shown in FIG. 2B, the functioning mitral valve 60 closes and effectively seals the left ventricle 30 from the left atrium 10 during systole, first passively then actively by increase in ventricular pressure, thereby allowing contraction of the heart tissue surrounding the left ventricle to advance blood throughout the vasculature.

Referring to FIGS. 3A-3B and 4A-4B, there are several conditions or disease states in which the leaflet edges of the mitral valve fail to appose sufficiently and thereby allow blood to regurgitate in systole from the ventricle into the atrium. Regardless of the specific etiology of a particular patient, failure of the leaflets to seal during ventricular systole is known as mal-coaptation and gives rise to mitral regurgitation.

Figure 3A:
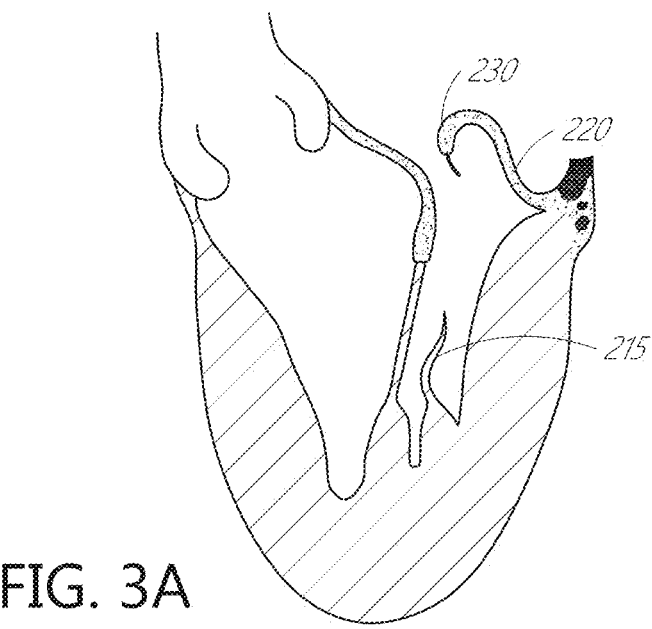
FIGS. 3A-3B illustrate a simplified cross-section of a heart, schematically showing mitral valve regurgitation during systole in the setting of mal-coaptation of the mitral valve leaflets.

Generally, mal-coaptation can result from either excessive tethering by the support structures of one or both leaflets, or from excessive stretching or tearing of the support structures. Other, less common causes include infection of the heart valve, congenital abnormalities, and trauma. Valve malfunction can result from the chordae tendineae becoming stretched, known as mitral valve prolapse, and in some cases tearing of the chordae 215 or papillary muscle, known as a flail leaflet 220, as shown in FIG. 3A. Or if the leaflet tissue itself is redundant, the valves may prolapse so that the level of coaptation occurs higher into the atrium, opening the valve higher in the atrium during ventricular systole 230. Either one of the leaflets can undergo prolapse or become flail. This condition is sometimes known as degenerative mitral valve regurgitation.

Figure 3B:
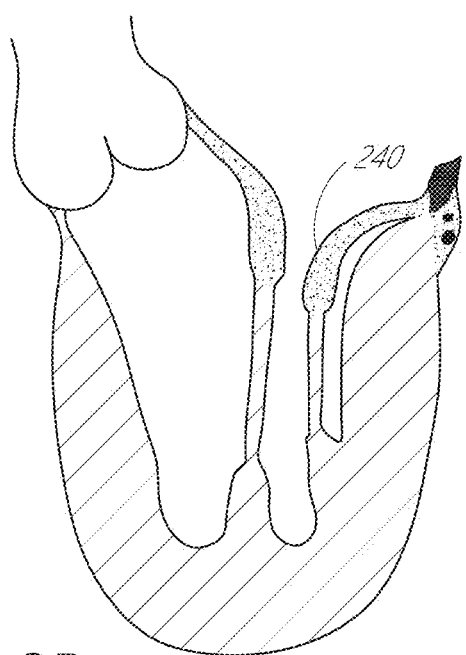

In excessive tethering, as shown in FIG. 3B, the leaflets of a normally structured valve may not function properly because of enlargement of or shape change in the valve annulus: so-called annular dilation 240. Such functional mitral regurgitation generally results from heart muscle failure and concomitant ventricular dilation. And the excessive volume load resulting from functional mitral regurgitation can itself exacerbate heart failure, ventricular and annular dilation, thus worsening mitral regurgitation.

FIG. 4A-4B illustrate the backflow BF of blood during systole in functional mitral valve regurgitation (FIG. 4A) and degenerative mitral valve regurgitation (FIG. 4B). The increased size of the annulus in FIG. 4A, coupled with increased tethering due to hypertrophy of the ventricle 320 and papillary muscle 330, prevents the anterior leaflet 312 and posterior leaflet 314 from apposing, thereby preventing coaptation. In FIG. 4B, the tearing of the chordae 215 causes prolapse of the posterior leaflet 344 upward into the left atrium, which prevents apposition against the anterior leaflet 342. In either situation, the result is backflow of blood into the atrium, which decreases the effectiveness of left ventricle compression.

Further description of coaptation assistance elements, tools, anchors, features, systems, and methods, which can be utilized in conjunction with the disclosure herein, can be found in the following applications, each of which is incorporated by reference in their entirety: U.S. patent application Ser. No. 13/099,532, filed May 3, 2011; U.S. patent application Ser. No. 13/531,407, filed Jun. 22, 2012; U.S. patent application Ser. No. 14/313,975, filed Jun. 24, 2014; U.S. patent application Ser. No. 14/742,199, filed Jun. 17, 2015; U.S. patent application Ser. No. 14/749,344, filed Jun. 24, 2015; and U.S. patent application Ser. No. 10/419,706, filed Apr. 18, 2003.

In some embodiments, the coaptation assistance elements described herein may be deployed to overlie the posterior leaflet, the chordae and papillary muscle. In some embodiments, the coaptation assistance element attaches superiorly to the posterior aspect of the annulus and inferiorly to the posterior aspect of the left ventricle via annular anchor and/or ventricular anchor. In other embodiments, more than one annular anchor and/or more than one ventricular anchor may be used to attach the coaptation assistance element. In some elements, the one or more annular anchors may be replaced by or supplemented with one or more atrial or commissural anchors, which can be annular in some embodiments. The coaptation assistance element may attach to the superior surface of the posterior annulus, the posterior atrial wall, or the annulus itself. A coaptation zone has been established between the coaptation assistance element and the native anterior leaflet. Similar coaptation assistance elements can be used in both functional and degenerative mitral valve regurgitation because the failure of leaflet coaptation occurs in both, regardless of the mechanism behind the dysfunction. In some embodiments, differently sized coaptation assistance elements can be placed such that the native anterior leaflet apposes the coaptation element at the appropriately established coaptation point, blocking flow of blood during contraction of the ventricle.

A variety of sizes of coaptation assistance elements may be provided, with differing dimensions configured to fit varying anatomies. For example, there may be a height, which measures from the superior annular attachment site to the inferior-most edge of the coaptation assistance element in a plane basically perpendicular to the plane defined by the annulus of the valve, a depth between the coaptation point and the superior attachment site, and a projection between the posterior wall at the level of the coaptation point and the coaptation point. There is also a medial-lateral diameter of the coaptation assistance element, typically larger in functional MR. During diastole, the coaptation assistance element may stay in substantially the same position, while movement of the native anterior leaflet opens the valve, permitting flow of blood from the left atrium to the left ventricle with minimal restriction. In some embodiments, the surface of the coaptation assistance element may balloon or stretch upwards during ventricular systole, while the anchors remain unmoved. This may be advantageous as enhancing the seal between the anterior or coaptation surface of the element and the native leaflet at the coaptation zone during systole. During diastole, the surface may return to an initial position in which it lies more anteriorly, toward the anterior leaflet. This may provide an improved blood flow path between the atrium and ventricle during diastole, improving outflow from the atrium past the coaptation assist element.

In some methods of use, the native posterior leaflet is left in position, and the coaptation assistance element is attached superiorly to the posterior annulus or adjacent atrial wall. Many possible alternate embodiments may have differing attachment mechanisms. In other methods of use, the posterior leaflet is not present, having been removed surgically or the result of disease. In some methods of use, the native leaflet attaches to the posterior surface of the coaptation assistance element. In some methods of use, the coaptation assistance element may attach to the anterior surface of the posterior leaflet, rather than the annulus or atrial wall. These are some examples of variations, but still others are contemplated. In some methods of use, an anchoring structure (not shown) could pass from the coaptation assistance element, through the atrial wall into the coronary sinus, wherein the anchoring structure attaches to a mating structure in the coronary sinus. In some methods of use, the anchoring structure, which could be a mechanical structure or a simple suture, can pass through the atrial wall and be anchored by a knot or mechanical element, such as a clip, on the epicardial surface of the heart. Similarly, attachment inferiorly may be to the ventricular muscle, through the apex into the epicardium or pericardium and secured from outside, or at other attachment sites using alternative attachment means.

The coaptation assistance element described herein may exhibit a number of desirable characteristics. Some embodiments need not rely on reshaping of the mitral annulus (such as by thermal shrinking of annular tissue, implantation of an annular ring prosthesis, and/or placement of a cinching mechanism either above or beneath the valve plane, or in the coronary sinus or related blood vessels). Advantageously, they also need not disrupt the leaflet structure or rely on locking together or fusing of the mitral leaflets. Many embodiments can avoid reliance on ventricular reshaping, and after implantation represent passive implanted devices with limited excursion which may result in very long fatigue life. Thus, the coaptation assistance element can be secured across a posterior leaflet while otherwise leaving native heart (e.g., ventricular, mitral annulus, etc.) anatomy intact.

Mitigation of mitral valve mal-coaptation may be effective irrespective of which leaflet segment(s) exhibit mal-coaptation. The treatments described herein will make use of coaptation assistance elements that are repositionable during the procedure, and even removable after complete deployment and/or tissue response begins or is completed, often without damaging the valve structure. Nonetheless, the coaptation assistance element described herein may be combined with one or more therapies that do rely on one or more of the attributes described above as being obviated. The coaptation assistance element can exhibit benign tissue healing and rapid endothelialization which inhibits migration, thromboembolism, infection, and/or erosion. In some cases, the coaptation assistance element will exhibit no endothelialization but its surface will remain inert, which can also inhibit migration, thromboembolism, infection and/or erosion.

Figure 5A:
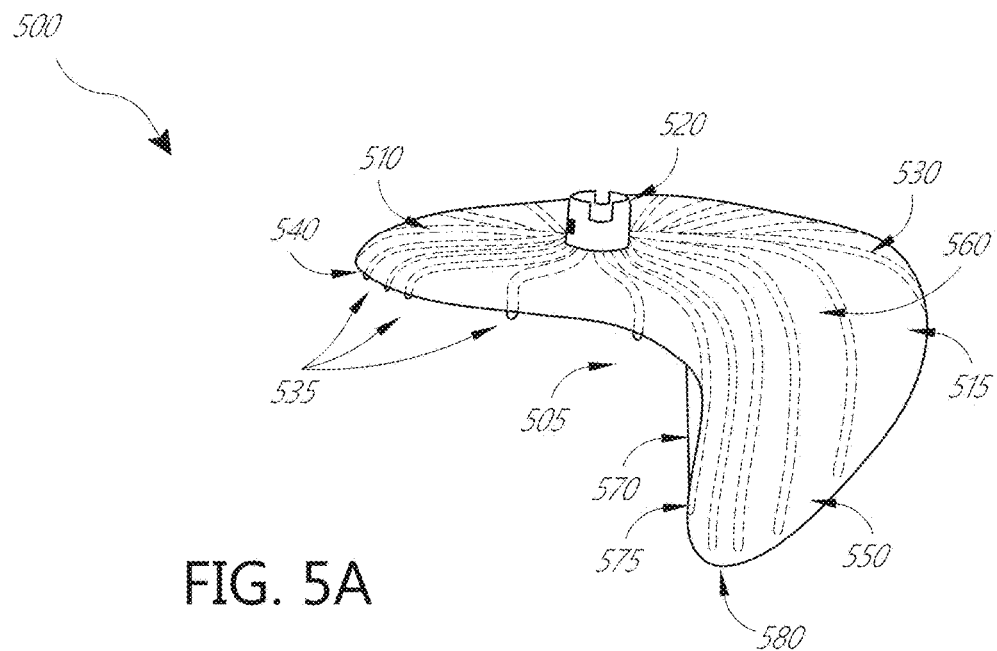
FIG. 5A illustrates a perspective view of an embodiment of a coaptation assistance element.
Figure 5B:
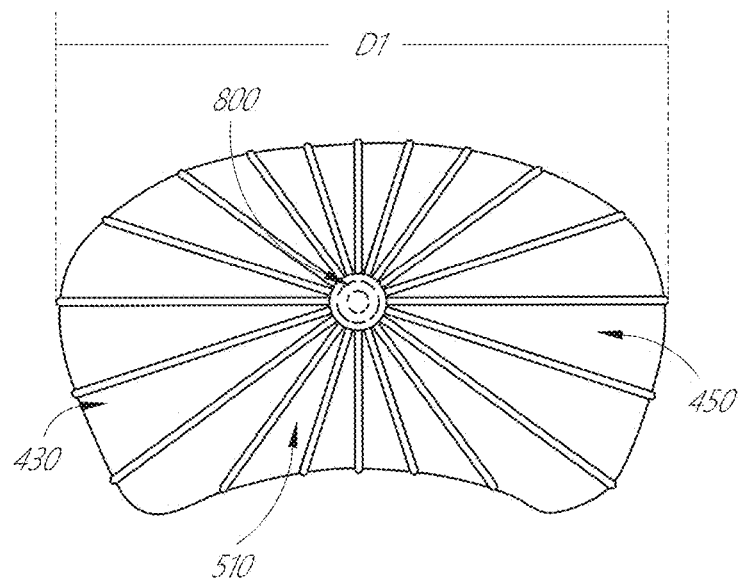
FIG. 5B illustrates the top view of the coaptation assistance element of FIG. 5A.
Figure 6:
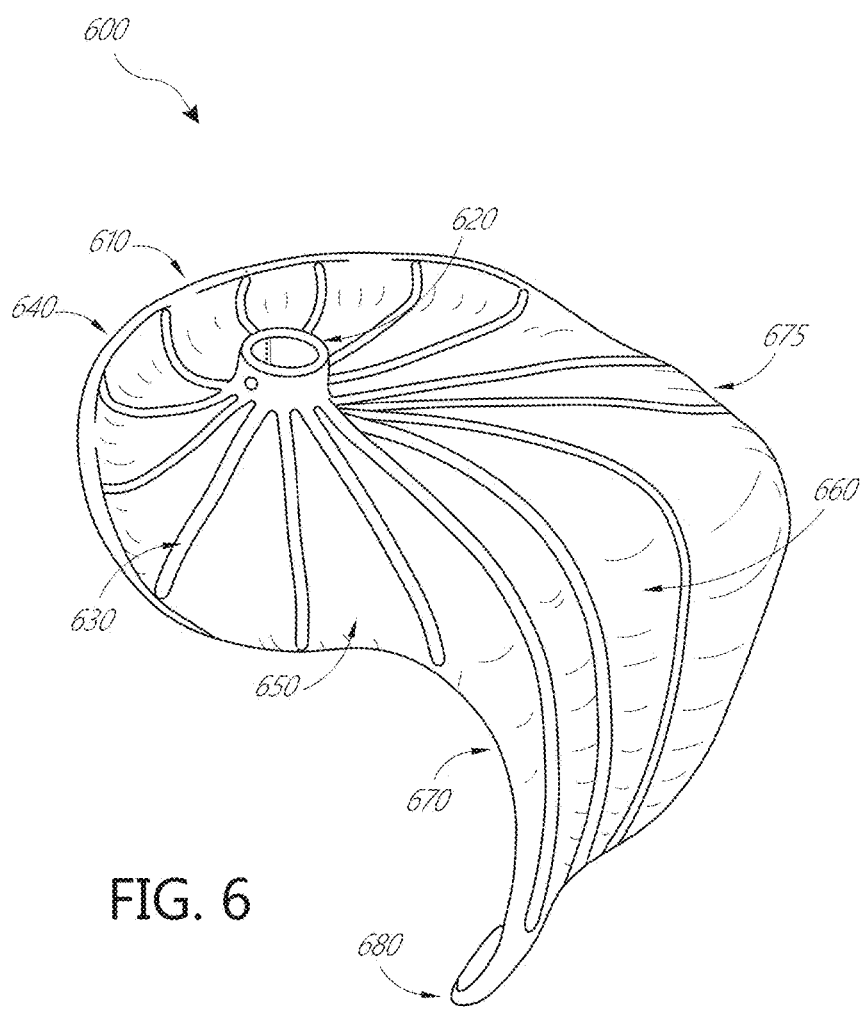
FIG. 6 illustrates a perspective view of an embodiment of a coaptation assistance element.

FIGS. 5A-5B show two views of an embodiment of a coaptation assistance element 500. The coaptation assistance element 500 can include a first surface 505 disposed toward a mal-coapting native leaflet, in the instance of a mitral valve, the posterior leaflet and a second surface 515 which may be disposed toward the anterior leaflet. The second surface 515 can include a coaptation surface 560. The superior edge 540 of the coaptation assistance element 500 may be curved to match the general shape of the annulus or adjoining atrial wall, as described herein. The superior edge 540 can be curved downward, toward the posterior leaflet, as shown in FIG. 5A, or curved upward, toward the atrial wall to match the general shape of the left atrial wall, as shown in FIG. 6 and described herein.

The coaptation assistance element 500 can have a geometry which permits it to traverse the valve between attachment sites in the atrium and ventricle. In some embodiments, the attachment sites are only in the atrium. In some embodiments, the attachment sites are only near the annulus and the commissures of the valve. The coaptation assistance element 500 can be unattached near the inferior edge 580. The coaptation assistance element 500 does not require ventricular attachment. In some embodiments, the geometry of the coaptation assistance element 500 helps to maintain the position of the coaptation assistance element 500 within the valve. In some embodiments, the coaptation assistance element 500 is curved to cup the posterior leaflet. In some embodiments, the coaptation assistance element 500 is curved backwards toward the superior edge 540. The coaptation assistance element 500 may provide the coaptation surface 560 for the anterior leaflet to coapt against. FIGS. 5A and 5B illustrate that geometry.

In some methods of use, the posterior leaflet can be left intact. The coaptation assistance element 500 may attach to the atrium or annulus such that it effectively seals off the posterior leaflet. In some methods of use, the posterior leaflet can be removed. The coaptation assistance element 500 may, in the instance that the leaflet is or has been removed, replace the posterior leaflet. In some embodiments, the coaptation assistance element 500 only requires annular attachment. In some embodiments, the coaptation assistance element 500 only requires attachment at a single point. The single point may be a central location of the coaptation assistance element 500, for instance, a centrally-located hub. In some embodiments, the coaptation assistance element 500 may attach to the atrium or annulus along an edge. In some embodiments, the coaptation assistance element 500 may attach to the atrium or annulus at a location separated from the edge of the coaptation assistance element 500, for instance, at a centrally-located hub.

The coaptation assistance element 500 can include an annular hub 520 engaging an annular anchor 800. The annular anchor 800 may be engaged at a proximal end by a driver, described herein. The annular anchor 800 can include a sharpened tip to engage tissue. In some methods of use, the tip of the annular anchor 800 is within the annular hub 520 during delivery of the coaptation assistance element 500. In some methods of use, the tip of the annular anchor 800 is above the annular section 510 during delivery. The tip of the annular anchor 800 can remain recessed within the annular hub 520 until the annular anchor 800 is rotated to engage tissue. In some embodiments, the coaptation assistance element 500 can be assembled extra-corporeally, engaging the annular anchor 800 to the coaptation assistance element 500 via the annular hub 520 and the drivers to the annular anchor 800. The drivers can then be withdrawn into a delivery catheter, with the coaptation assistance element 500 in a collapsed position. The drivers may be separately manipulated by the operator to place the annular anchor 800 in the appropriate position. Alternatively, the annular anchor 800 may be engaged to the coaptation assistance element 500 and/or the driver sequentially, either before or after deployment through the delivery catheter. The coaptation assistance element 500 after placement can entirely cover the posterior leaflet so that the coaptation assistance element 500 coapts with the anterior leaflet during systole and, with the native anterior leaflet, maintains the valve seal at the annular ring.

In some embodiments, the annular anchor 800 is an active anchor. The user can selectively engage or disengage the annular anchor 800 from tissue. Unlike barbs or other passive anchors, the annular anchor 800 has to be activated such as by rotation in order to engage tissue. The annular anchor 800 allows placement of the coaptation assistance element 500 prior to engagement of the annular anchor 800. The coaptation assistance element 500 can make contact with the tissue without any adhesion of the annular anchor 800. In some embodiments, the annular anchor 800 and corresponding hub 520 are centrally located on the coaptation assistance element 500. The annular anchor 800 and corresponding hub 520 are spaced apart from any edge of the coaptation assistance element 500. The location of the annular anchor 800 and corresponding hub 520 can be at a neutral center preventing swinging of the coaptation assistance element 500 when the coaptation assistance element 500 is held by the annular hub 520. The corresponding hub 520 provides an advantageous location to hold and move the coaptation assistance element 500.

The annular hub 520 may have a built-in or coupled annular anchor 800. In some embodiments, the annular anchor 800 can be retained by a cross-pin, described herein, within the annular hub 520. The cross-pin may pass through the helical structure of the annular anchor 800 to prevent dislodgement of the annular anchor 800 from the annular hub 520 by a blunt force. The annular anchor 800 may comprise a helix rotatable with respect to the annular hub 520. In some embodiments, other anchors may be used. The annular anchor 800 may be in the form of a tether or other attachment means extending from the coaptation assistance element 500 thru the ventricle septum to the right ventricle.

The annular anchor 800 may be in the form of a tether or other attachment means extending thru the apex into the epicardium or pericardium. The annular anchor 800 may be secured from outside the heart in and combined endo/epi procedure. When helical anchors are used, they may comprise bio-inert materials such as Platinum/Ir, a Nitinol alloy, and/or stainless steel.

In some embodiments, the coaptation assistance element 500 can include a single central annular anchor 800 inside the annular hub 520. The coaptation assistance element 500 can be delivered percutaneously as described herein by attachment of a delivery catheter to the annular hub 520. The coaptation assistance element 500 can be configured for adjustable positioning by removing and reattachment of the annular anchor 800. The coaptation assistance element 500 can be recapturable by removal of the annular anchor 800 and withdrawal of the coaptation assistance element 500. The coaptation assistance element 500, may also include secondary anchors including commissural anchors, ventricular anchor, annular anchors, barbs, tethers or any other known fixation device.

As may be seen in FIGS. 5A-5B, the coaptation assistance element 500 can include a plurality of struts 530. In some embodiments, one or more of the struts 530 have one end terminating at the hub 520 and the other end extending radially outwardly toward one of the superior edge 540, the lateral edges 570 and 575, and the inferior edge 580 of the coaptation assistance element 500. The struts 530 may extend outward in various directions from the hub 520, and can be spaced apart from adjacent struts 530 at regular or irregular intervals. In some embodiments, adjacent struts 530 extend outward from the hub at an angle of between about 5 degrees and about 45 degrees, between about 10 degrees and about 30 degrees, or about 5, 10, 15, 20, 25, or 30 degrees with respect to an adjacent strut 530. The struts 530 may be arranged generally parallel to the longitudinal axis of the coaptation assistance element 500 to assist in maintaining the shape of the coaptation assistance element 500 upon placement. The struts 530 may allow the coaptation assistance element 500 to assume a reduced configuration for deployment through a catheter. In some embodiments, the struts 530 that form a portion of the coaptation zone of the implant 500 have a maximum length that is greater than struts 530 that only form a portion of the annular zone of the implant. In some embodiments, the struts 530 that form a portion of the coaptation zone of the implant can be, for example, at least about 10%, 20%, 30%, 40%, 50%, 75%, 100%, 125%, or 150% longer than the struts 530 that form a portion of the annular zone of the implant.

FIG. 5A shows a view of the coaptation assistance element 500 with an annular anchor site 535. The annular anchor site 535 can be a portion of the struts 530. The annular anchor site 535 is shown extending downward from the coaptation assistance element 500 in FIG. 5A. In other embodiments, the annular anchor site 535 may extend in other directions from the coaptation assistance element 500 to engage tissue. In some embodiments, the annular anchor site 535 comprises one or more barbs having a sharpened tip. The annular anchor site 535 may be a passive anchor.

In some embodiments, the coaptation assistance element 500 can include one or more retractable barbs. For instance, the barbs can be retracted during delivery of the coaptation assistance element 500. For instance, the barbs can be advanced after the coaptation assistance element 500 is positioned relative to the anatomical structures. In some embodiments, the barbs are actively retracted and/or advanced. For instance, the delivery catheter described herein can include a mechanism coupled to the barbs designed to retract and/or advance the barbs. In other embodiments, the barbs are passively advanced and/or retracted. In some embodiments, the coaptation assistance element 500 is delivered with the barbs in a retracted state. In some embodiments, the barbs can be covered by the valve body covering as described herein. In some embodiments, the interface between the tissue and the valve body covering pushes back the valve body covering and exposes the barbs. In some embodiments, the tissue dissolves and/or absorbs a portion of the valve body covering and exposes the barbs. In some embodiments, the motion of the purse-string suture, described herein, advances the barbs. In some embodiments, the motion of the purse-string suture causes motion of the valve body covering to expose the barbs. Other configurations are contemplated.

The annular anchor site 535 may define a diameter D1 shown in FIG. 5B, which may in some embodiments correspond to the distance between the medial and lateral commissures of the native valve or the intracommissural distance (ICD). D1 may range between 20-60 mm with, in some embodiments, a preferred length between 35-45 mm, as corresponding most closely to the widest range of human mitral ICD. In some embodiments, D1 may be the distance from the right to left fibrous trigones.

The coaptation assistance element 500 can include a generally annular section 510. The annular section 510 can be positioned above the native leaflets when the coaptation assistance element 500 is deployed. In some embodiments, the annular section 510 may be curved toward the annulus or curved away from the annulus. The annular section 510 can be concave. In other embodiments, the annular section 510 may be substantially flat with respect to the annulus. One or more of the struts 530 may curve laterally from the hub 520 toward the superior edge 540 to assist in maintaining the shape of the annular section 510 of the coaptation assistance element 500 upon deployment. The coaptation assistance element 500 can curve downward from the hub 520 toward the annular anchor site 535. In some embodiments, the coaptation assistance element 500 does not rest against the posterior leaflet. In some embodiments, the annular anchor site 535 is the only point of contact between the posterior annulus of the mitral valve and the coaptation assistance element 500. The superior edge 540 can include an annular radius of curvature. The annular curve radius can curve toward the annulus. The annular curve radius can curve toward the coaptation surface 560. In some embodiments, the annular curve radius can be between 0 mm-5 mm, 5 mm-10 mm, 10 mm-15 mm, 15 mm-20 mm, 20 mm-25 mm, 25 mm-30 mm, etc.

The struts 530 may be composed of a radio-opaque material. In some embodiments, the struts 530 are composed of resiliently deformable materials such as a shape memory metal, e.g., Nitinol or a shape memory polymer. In some embodiments, the material is Elgiloy. In other embodiments, the struts 530 may be composed of other materials to include stainless steel, polypropylene, high density polyethylene (PE), Dacron, acellular collagen matrix such as SIS, or other plastics, etc. In other embodiments, the struts 530 may be a combination such as a high density PE sheath around a core of ePTFE, Dacron, and/or polypropylene. The struts 530 may have a circular cross section, an oval cross section, or be ribbon-like. In some embodiments, the struts 530 are coiled springs or zig-zag shaped. The struts 430 may have a constant stiffness. In some embodiments, one or more struts 530 can have differing stiffness along the length of the one or more struts 530. The struts 530 may be stiffer at the annular end than at the ventricular end of the coaptation assistance element 500. The struts 530 may be less stiff at the annular end than at the ventricular end of the coaptation assistance element 500. The struts 530 may be stiffer at a midpoint, for instance at an inflection point or curve. The struts 530, along with one or more other support structures, can form a frame. In some embodiments, one or more support structures may be provided which run parallel to the superior edge 540 of the coaptation assistance element 500 and assist in maintaining the shape of the superior edge 540. The struts 530 and/or other support structures of the frame can be laser-cut from a Nitinol tube in some embodiments.

The coaptation assistance element body covering 550 may be comprised of a material such as ePTFE. Other materials for the coaptation assistance element body covering 550 include polyester, polyurethane foam, polycarbonate foam, biologic tissue such as porcine pericardium, processed bovine pericardium, pleura, peritoneum, silicone, Dacron, acellular collagen matrix, etc. In some embodiments, the coaptation assistance element body covering 550 can include a foam material surrounded by ePTFE. Use of sponge or foam material in some embodiments enhances the capability of having the coaptation assistance element 500 to fold to a small enough diameter to pass through a catheter. In some embodiments, the coaptation assistance element body covering 550 has no pores. In other embodiments, the coaptation assistance element body covering 550 may have micropores to enhance endothelialization and cellular attachment. The coaptation assistance element body covering 550 may also incorporate a radiopaque material or an echo-enhancement material for better visualization. Any support structures of the coaptation assistance element 500 including the struts 530 or support interface including the hub 520 may be coated with radio-opaque materials such as gold or platinum or impregnated with barium. The coaptation surface 560 may be coated with an echo enhancement material. The coaptation assistance element body covering 550 may be coated with a material to inhibit thrombosis, such as heparin bonding or quinoline and quinoxaline compounds, or with a material to accelerate endothelialization, or with antibiotic to inhibit infection. In some embodiments, the purse-string suture 1010 described herein can incorporate a radiopaque material or an echo-enhancement material for better visualization.

In some embodiments, the struts 530 may be sandwiched between layers of coaptation assistance element body covering 550. The coaptation assistance element body covering 550 may be composed of the same material on the first surface 505 and the second surface 515. The coaptation assistance element body covering 550 may be composed of different materials on the first surface 505, or a portion thereof, and the second surface 515, or a portion thereof. In some embodiments, the struts 530 may be attached to or embedded in the first surface 505 or the second surface 515 of a single layer of coaptation assistance element body covering 550. In some embodiments, the struts 530 may be "stitched" through the coaptation assistance element body covering 550. The annular anchor site 535 can be exposed ends of the struts 530 from the coaptation assistance element body covering 550.

The coaptation assistance element 500 can include a purse-string suture 1010. The purse-string suture 1010 can extend along a portion of the coaptation assistance element 500. The purse-string suture 1010 can extend along the superior edge 540, or a portion thereof. The purse-string suture 1010 can extend along the lateral edge 570, or a portion thereof. The purse-string suture 1010 can extend along the lateral edge 575, or a portion thereof. The purse-string suture 1010 can extend along the inferior edge 580, or a portion thereof. The purse-string suture 1010 can extend along a perimeter, or a portion thereof, of the coaptation assistance element 500. The purse-string suture 1010 can extend along one or more struts 530. The purse-string suture 1010 can extend in a linear path, a non-linear path, a curve, a semi-circle or any open or closed shape.

In some embodiments, the purse-string suture 1010 may be sandwiched between layers of valve body covering 550. For instance, the purse-string suture 1010 can be disposed in a lumen between layers of coaptation assistance element body covering 550. In some embodiments, the purse-string suture 1010 may be attached to or embedded in the first surface 505 or the second surface 515 of a single layer of valve body covering 550. In some embodiments, the purse-string suture 1010 may be "stitched" through the coaptation assistance element body covering 550. The purse-string suture 1010 can pass from the first surface 505 to the second surface 515 and back to the first surface 505. The purse-string suture 1010 can include one or more exposed ends from the coaptation assistance element body covering 550. In embodiments where the purse-string suture 1010 is a loop, the purse-string suture can include one or more exposed sections of the loop from the valve body covering.

The coaptation assistance element 500 may be collapsed by tightening the purse-string suture 1010. The coaptation assistance element 500 may be expanded by loosening the purse-string suture 1010. The one or more exposed ends or loops can be manipulated by a delivery catheter or other tool to tighten or loosen the purse-string suture 1010. The ability to collapse or expand the coaptation assistance element 500 may be beneficial for recapture of the coaptation assistance element 500 and/or repositioning of the coaptation assistance element 500.

The coaptation assistance element 500 may be rotated by tightening one or more purse-string suture 1010 and/or loosening one or more purse-string suture 1010. For instance, tightening one or more purse-string suture 1010 on the lateral edge 570 and/or loosening one or more purse-string suture 1010 on the lateral edge 575 may cause the coaptation assistance element 500 to rotate. One or more purse-string sutures 1010 may be coupled to the coaptation assistance element 500 to enable multi-directional rotation.

The coaptation assistance element 500 may be expanded by loosening the purse-string suture 1010. The one or more exposed ends or loops can be manipulated by a delivery catheter or other tool to tighten or loosen the purse-string suture 1010. The ability to collapse or expand the coaptation assistance element 500 may be beneficial for recapture of the coaptation assistance element 500 and/or repositioning of the coaptation assistance element 500.

The coaptation surface 560 of the coaptation assistance element 500 may be adjusted by motion of the purse-string suture 1010. The one or more exposed ends or loops can be manipulated by a delivery catheter or other tool to tighten or loosen the purse-string suture 1010 to change the curvature of the coaptation surface 560 in situ. The ability to adjust the curvature of the coaptation assistance element 500 may be beneficial to conform to the geometry of heart including the geometry of the anterior leaflet.

The annular dimension of the coaptation assistance element 500 may be adjusted by motion of the purse-string suture 1010. The one or more exposed ends or loops can be manipulated by a delivery catheter or other tool to tighten or loosen the purse-string suture 1010 to change one or more dimensions of the coaptation assistance element 500 in situ. The ability to adjust dimensions of the coaptation assistance element 500 may be beneficial to conform to the geometry of the heart.

The coaptation assistance element 500 can include one or more purse-string sutures 1010. In some embodiments, the coaptation assistance element 500 includes one purse-string suture, two purse-string sutures, three purse-string sutures, four purse-string sutures, five purse-string sutures, six purse-string suture, seven purse-string sutures, eight purse-string sutures, nine purse-string sutures, ten purse-string sutures, etc. For instance, a purse-string suture 1010 can extend along each edge of the coaptation assistance element 500. When multiple purse-string sutures are provided, the purse-string sutures 1010 can act together to change the configuration of the coaptation assistance element 500. When multiple purse-string sutures are provided, the purse-string sutures 1010 can act independently to change the configuration of the coaptation assistance element 500.

FIG. 5A further illustrates a coaptation element height, corresponding to the distance between the inferior edge 580 and the annular hub 520 as measured perpendicular to the plane defined by the annulus of the valve. Coaptation element height of some embodiments may be 10-80 mm, with some embodiments ranging between 40-55 mm. The coaptation element height can be between 10-20 mm, 20-30 mm, 30-40 mm, 40-50 mm, 50-60 mm, 60-70 mm, 70-80 mm, etc.

FIG. 5A illustrates the generally triangular shape of coaptation assistance element 500, such that the coaptation assistance element 500 has a superior edge 540, lateral edges 570 and 575, and inferior edge 580. In some embodiments, the superior edge 540 has a length greater than that of inferior edge 580, such that the transverse distance between lateral edges 570 and 575 generally decreases from superior to inferior on the coaptation assistance element 500. For example, the length of the superior edge 540 may be in the range of 15-50 mm, or 25-35 mm, while the length of the inferior edge 580 may be in the range of 1-15 mm, or 2-6 mm.

The annular hub 520 may be a hub, an eyelet, or any other tether site known in the art. In some embodiments, the annular hub 520 is located at a midpoint of the distance D1. In some embodiments, the annular hub 520 is located at a neutral center to prevent swinging of the coaptation assistance element 500 when the coaptation assistance element 500 is held by the annular hub 520. In other embodiments, the annular hub 520 is located at one of the commissures. While only one annular anchor 800 is shown, in other embodiments, two or more annular hubs 520 may be provided.

In some embodiments, the struts 530 can comprise NiTi tubing. In some embodiments, the struts 530 can be laser cut from the tubing. In some embodiments, the frame including one or more struts 530 and/or one or more support structures can be laser cut from a single piece of material. In some embodiments, the frame including one or more struts 530, the annular hub 520, and/or one or more support structures can be integrally formed. In some embodiments, the coaptation assistance element body covering 550 comprises ePTFE lamination. The lamination can surround one or more of the struts 530 and/or one or more support structures (e.g., one side, two sides, first side 505, second side 515). The struts 530 and/or one or more support structures can be encased by two or more layers of lamination. The perimeter of the annular section 510 of the coaptation assistance element 500 can be cupped down. The perimeter of the annular section 510 of the coaptation assistance element 500 can be cupped up. The perimeter of the annular section 510 of the coaptation assistance element 500 can include secondary anchors such as the annular anchor site 535.

In some embodiments, the annular anchor 800 and the annular hub 520 form a single central anchor system. In some embodiments, the coaptation assistance element 500 is affixed to the tissue by only one annular anchor 800 which passes through the hub 520. In other embodiments, additional fixation is included. In some embodiments, the coaptation assistance element 500 is affixed to the tissue by the one anchor 800 which passes through the hub 520 and the annular anchor site 535 as described herein. The system can include features to allow rotational adjustment of the coaptation assistance element 500. For instance, the hub 520 and/or the annular anchor 800 can be coupled to the delivery catheter to allow the transmission of axial movement and/or torque. The coaptation assistance element 500 can be immovably grasped by a delivery catheter such that rotation of a feature of the delivery catheter, such as a handle, causes rotation of the coaptation assistance element 500. The coaptation assistance element 500 can be immovably grasped by a delivery catheter such that axial movement of a feature of the delivery catheter, such as a drive shaft, causes axial movement of the coaptation assistance element 500.

In some embodiments, the hub 520 is located at a neutral position on the coaptation assistance element 500. The neutral position can be a central location on the annular section 510. The neutral position can be between the lateral edges 505, 515. The neutral position can be between the superior edge 540 and the cooptation surface 560. The neutral position can enhance stability of the coaptation assistance element 500 when the coaptation assistance element 500 is grasped at a single location such as the hub 520 and/or the annular anchor 800. The neutral position can be aligned with a structure of the mitral valve. The neutral position can be aligned along the coaptation zone.

In some embodiments, the coaptation assistance element 500 is delivered percutaneously as described herein. In some embodiments, the coaptation assistance element 500 is adjustable via a delivery catheter. For instance, the coaptation assistance element 500 can be expanded and/or collapsed by the delivery catheter. For instance, the coaptation assistance element 500 can be rotated about a fixed position of the annular hub 520. For instance, the coaptation assistance element 500 can be recapturable. For instance, the coaptation assistance element 500 can be engaged and reengaged by the delivery catheter. For instance, the annular anchor 800 can be disengaged from the tissue and the delivery catheter can recapture the coaptation assistance element 500.

Figure 5C:
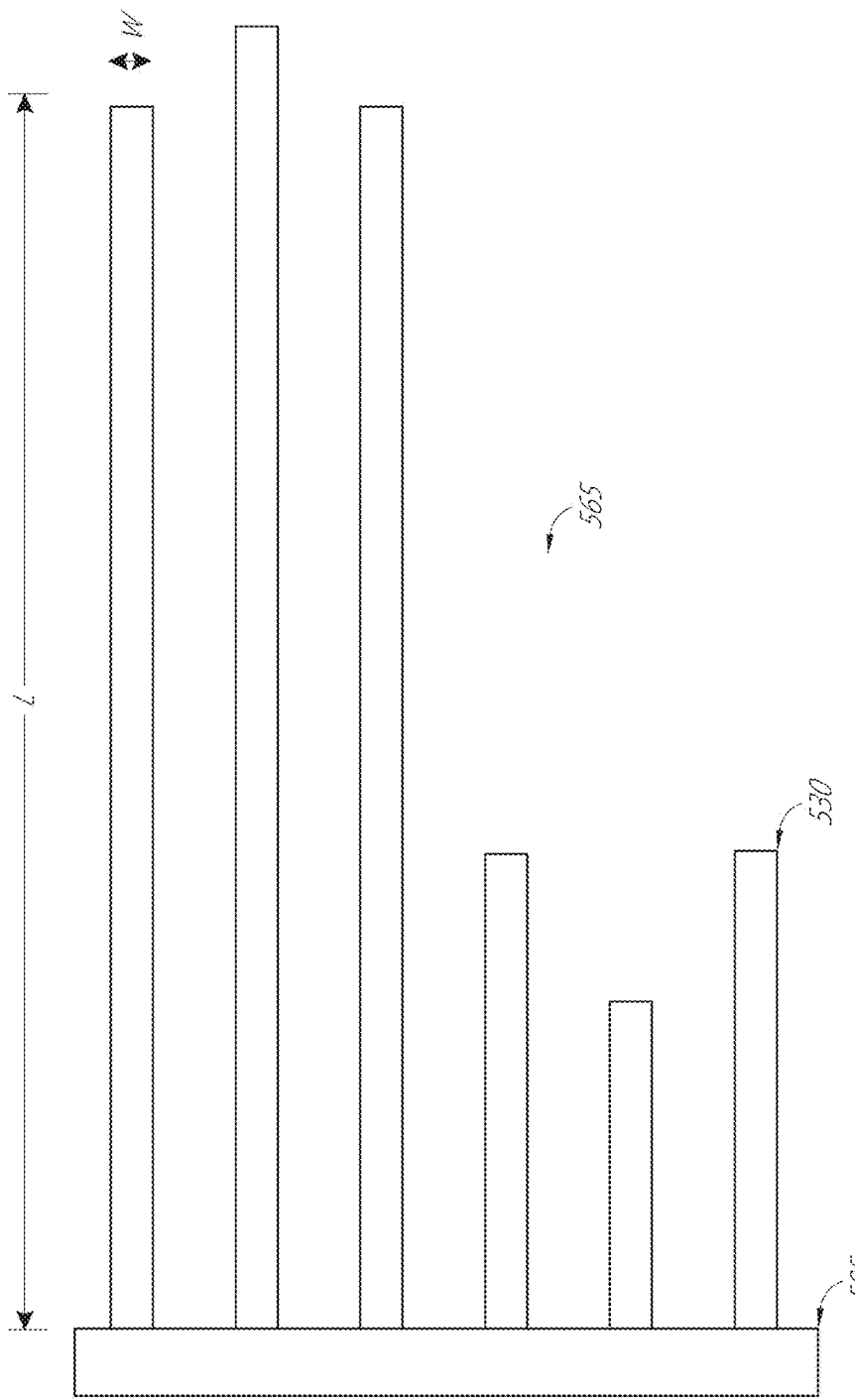
FIG. 5C-5D illustrates an embodiment of the struts of a coaptation assistance element.
Figure 5D:
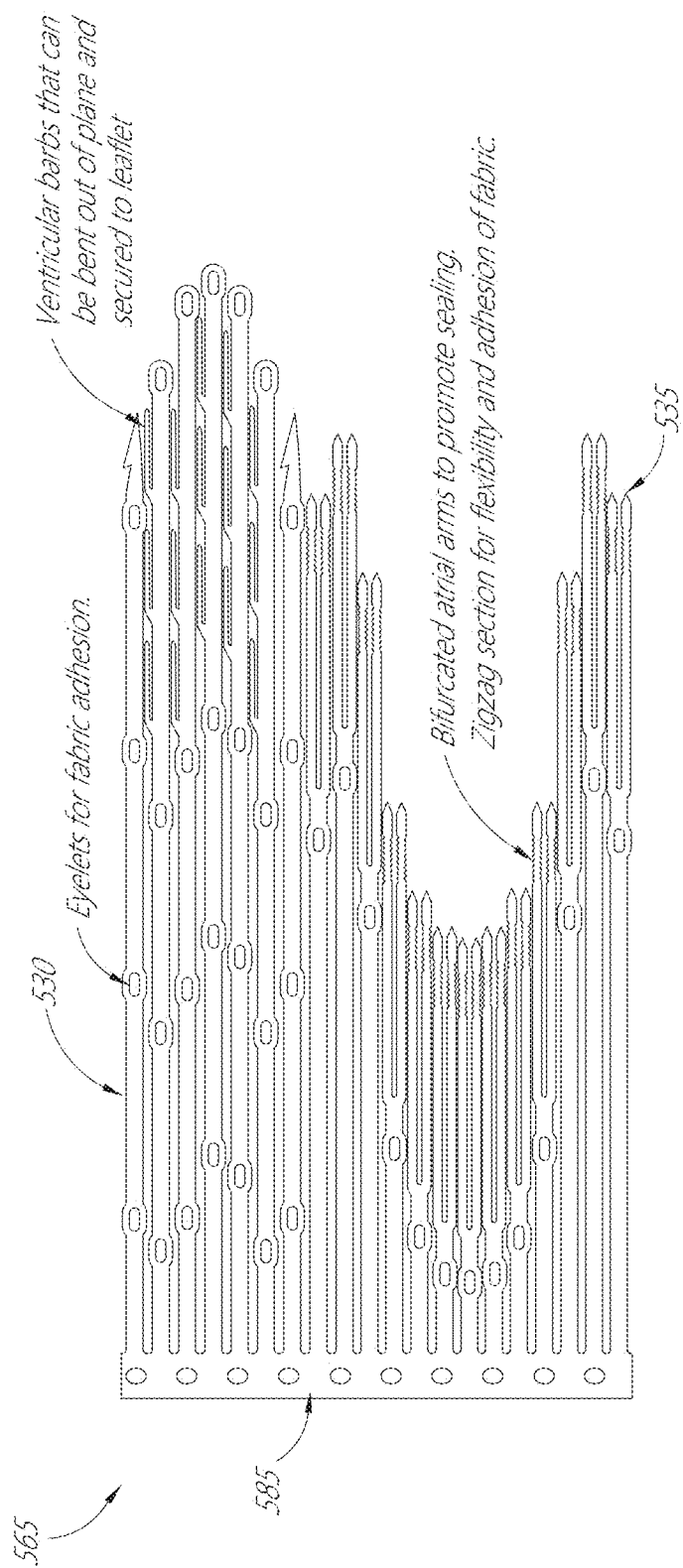

FIGS. 5C-5D illustrate embodiments of a frame 565 of the coaptation assistance element 500. These figures illustrated the flattened patterns of the frame 565 prior to bending and/or shape setting. In some embodiments, the frame 565 is cut from a tubular stock. In other embodiments, the frame 565 is cut from flat stock such as a flat sheet of material. The frame 565 including portions thereof can be laser cut. The frame 565 can include one or more struts 530. In the embodiment shown in FIG. 5D, the frame 565 includes twenty struts 530 but other configurations are contemplated (e.g., one strut, two struts, three struts, four struts, five struts, between five and ten struts, between ten and fifteen struts, between fifteen and twenty struts, between twenty and twenty-five struts, between twenty-five and thirty struts, etc.).

In some embodiments, one or more struts 530 are coupled to a backing 585. In some embodiments, the backing 585 is transverse to the direction of the struts 530. In the illustrated embodiment, the backing 585 is vertical or generally vertical and the struts 530 are horizontal or generally horizontal. In some embodiments, the backing 585 is the annular hub 520. For instance, the two ends of the backing 585 can be joined using methods known in the art to form the annular hub 520. The two ends are joined, for instance, if the frame 565 is cut from flat stock. In other embodiments, the frame 565 is formed from tubular stock. The backing 585 can be a portion of uncut tubular stock. The two ends of the backing 585 may not need to be joined if the frame 565 is formed from tubular stock. The uncut tubular stock can form the annular hub 520. The patters of the frame 565 as shown in FIG. 5D can be cut from tubular stock, thereby eliminating the need to join the two ends of the backing. Other modes of manufacturing are contemplated to form the frame 565. In other embodiments, the backing 585 forms at least a portion of the annular hub 520. In some embodiments, the backing 585 surrounds at least a portion of the annular hub 520. In some methods of manufacturing, the backing 585 can be formed into a shape of a circle. In some methods of manufacturing, the struts 530 extend radially outward from the backing 585 once the backing 585 is shaped into a circle. The backing 585 can include one or more openings designed to accept a cross-pin, as disclosed herein. In some methods of manufacturing, the backing 585 is removed.

Referring to FIGS. 5A and 5C, a plurality of struts 530 can extend from the annular hub 520 to the inferior end 580. In some embodiments, these struts 530 are longer than other struts 530 of the frame 565. In some embodiments, the struts 530 might include an anchor or barb that interacts with the subvalvular structure, including the ventricular wall. In some embodiments, these struts engage the posterior leaflet or another anatomical structure. In some embodiments, the ventricular anchoring is passive.

Referring to FIG. 5A-5D, a plurality of struts 530 can extend from the annular hub 520 to the superior end 540. In some embodiments, these struts 530 are shorter than other struts 530 of the frame 565. In some embodiments, these struts 530 form an atrial anchor and/or the annular anchor site 535 described herein. In some embodiments, these struts engage the annulus or another anatomical structure. In some embodiments, the annular anchoring is passive.

Referring to FIGS. 5A and 5D, a plurality of struts 530 can extend from the annular hub 520 to the lateral edges 570 and 575. In some embodiments, these struts 530 have a mid-length between the ventricular struts and the atrial struts. In some embodiments, these struts engage the commissures or another anatomical structure. In some embodiments, the commissural anchoring is passive.

The struts 530 can have a variety of lengths based on the desired shape of the coaptation assistance element 500. As shown in FIGS. 5C-5D, two or more struts 530 have a different length. As shown in FIGS. 5C-5D, two or more struts 530 have the same length. FIG. 5C shows a schematic model of the frame 565. One or more of the top three struts can form the coaptation surface 560 and extend to the inferior edge. One or more of the bottom three struts can form the annular portion and extend to the superior edge. The struts 530 can be laser-cut from a tube. The length can be measured from the annular hub 520 to an edge of the coaptation assistance element 500. The range of the strut length can be 1 mm to 50 mm. The range of the strut length can be 5 mm to 35 mm for the annular portion 510. The strut length can be about 15 mm for the annular portion 510. The range of the strut length can be 20 mm to 35 mm for the coaptation surface 560. The strut length can be about 30 mm for the coaptation surface 560. Other configurations of the range of strut length are contemplated e.g., 5 mm to 45 mm, 10 mm to 40 mm, 15 mm to 35 mm, about 5 mm, about 10 mm, about 15 mm, about 20 mm, about 25 mm, about 30 mm, about 35 mm, about 40 mm, about 45 mm, about 50 mm, about 55 mm, about 60 mm, 1 mm to 10 mm, 5 mm to 15 mm, 10 mm to 20 mm, 15 mm to 25 mm, 20 mm to 30 mm, 25 mm to 35 mm, 30 mm to 40 mm, etc.

The width can be measured perpendicular to the strut length. The range of the strut width can be 0.1 mm to 2 mm. One or more struts can have an outer diameter or width of about 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, less than 0.5 mm, less than 1 mm, less than 1.5 mm, less than 2 mm, etc. One or more struts 530 can have a varying width along the strut length. In some embodiment, one or more struts 530 taper near an edge of the coaptation assistance element 500. In some embodiments, one or more struts 530 taper near the annular hub 520. The one or more struts 530 can include a reduced diameter or taper at the connection between the one or more struts 530 the annular hub 520. The taper near the annular hub 520 can aid in collapsing the coaptation assistance element 500. The taper near the annular hub 520 can facilitate insertion of the coaptation assistance element 500 into the delivery catheter. The taper can reduce stress and/or strain in the strut 530 during collapse. In some embodiments, the taper can aid in longer fatigue life. In some embodiments, one or more struts 530 include a varying width taper. The width of the strut 530 can vary along the length of the strut 530. One or more struts 530 can include eyelets along the length of the strut 530. In some embodiments, the eyelets can reduce stress of the struts 530. In some embodiments, the eyelets can facilitate adhesion between the strut 530 and the valve body covering 550.

The thickness can be measured perpendicular to the strut length and strut width. The thickness can be determined by the thickness of the material of the frame, as described herein. The range of the strut thickness can be 0.2 mm to 0.5 mm. One or more struts can have a thickness of about 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, less than 0.5 mm, less than 1 mm, less than 1.5 mm, less than 2 mm, etc.

One or more the struts 530 can include barbs. In some embodiments, the barbs can be configured for placement near the ventricular end of the coaptation assistance element 500. In some embodiments, the barbs can be bent out of the plane of the strut 530. In some embodiments, the barb can have a bayonet configuration. In some embodiments, the barbs can have a sharped tip. In some embodiments, one or more struts 530 can be bifurcated. In some embodiments, one or more struts 530 can include one or more zigzag sections. In some embodiments, the zigzag section reduces stress and/or increases flexibility of the strut 530. In some embodiments, the zigzag section facilitates adhesion between the strut 530 and the coaptation assistance element body covering 550.

In some embodiments, one or more struts 530 can include supplemental barbs. In some embodiments, the supplemental barbs can be bent out of the plane of the strut 530. In some embodiments, one or more portions of the strut length are bent out of the plane of the strut. For instance, a portion of the strut can be twisted or bent during manufacturing. In some embodiments, the portion that is bent out of plane is shaped to engage tissue. In some embodiments, one or more struts 530 can include increased widths to compensate for electropolishing or other post manufacturing processes. In some embodiments, the backing 585 can include one or more features to engage the delivery catheter described herein. In some embodiments, the backing 585 can include one or more notches designed to interface with a locking tab or other feature of the delivery catheter as described herein. In some embodiments, one or more struts 530 can include a greater width than other struts 530. In some embodiments, the frame 565 includes two or more struts 530 that have a greater width than other struts 530. The two or more struts 530 can facilitate visualization of the coaptation assistance element 500. In some embodiments, the two or more struts 530 that have a greater width are designed to be placed near the commissures when the coaptation assistance element 500 is deployed. In some embodiments, one or more struts 530 can have smaller width compared with one or more other struts. In some embodiments, each strut 530 has the same width near the annular hub 520. The backing 585 can be modified to interface with the delivery catheter, as described herein. The backing 585 can be designed to allow independent rotation of the anchor 800 within the hub of the coaptation assistance element 500.

Figure 5F:
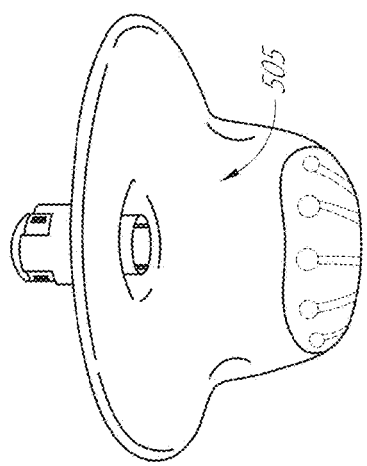
FIGS. 5E-5G illustrate the coaptation assistance element of FIG. 5A without annular anchor site.
Figure 5G:
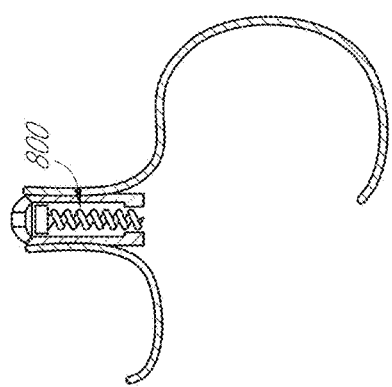
Figure 5E:
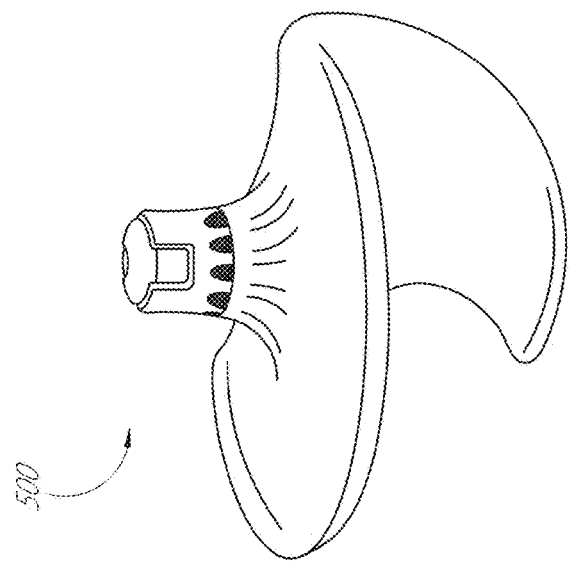

FIGS. 5E, 5F, and 5G show an embodiment of the coaptation assistance element 500 without barbs. FIG. 5E shows a schematic perspective view of the coaptation assistance element 500. FIG. 5F shows a schematic perspective view of the first surface 505 disposed toward a mal-coapting native leaflet. FIG. 5G shows a schematic cross-sectional view including the anchor 800.

Figure 5I:
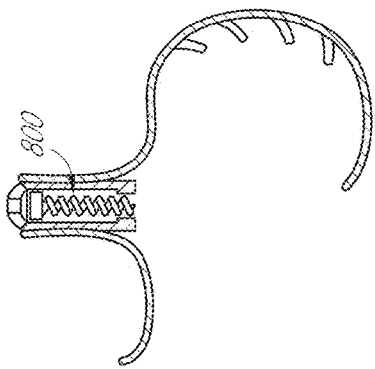
FIGS. 5H-5J illustrate the coaptation assistance element of FIG. 5A with leaflet anchor sites.
Figure 5J:
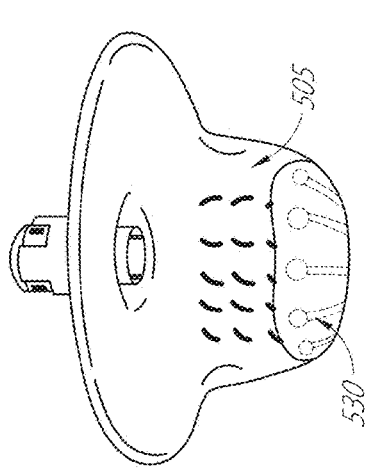
Figure 5H:
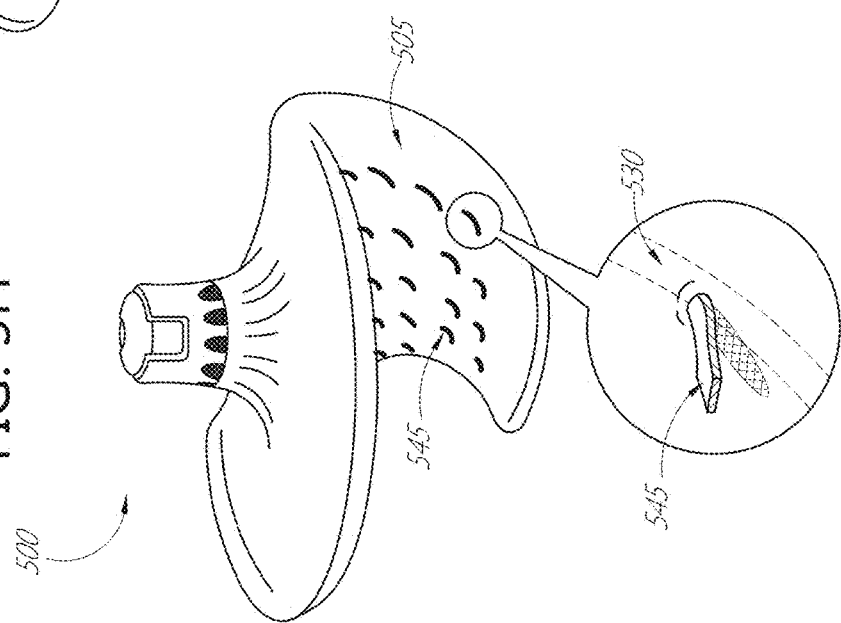

FIGS. 5H, 5I, and 5J show an embodiment of the coaptation assistance element 500 with leaflet anchor sites 545. As shown in FIG. 5A, the annular anchor sites 535 such as barbs can extend along an edge of the coaptation assistance element 500. FIGS. 5H, 5I, and 5J show an embodiment of the coaptation assistance element 500 with leaflet anchor sites 545 extending from the first surface 505 disposed toward a mal-coapting native leaflet.

FIG. 5H shows a schematic perspective view of the coaptation assistance element 500 including an enlarged section showing the leaflet anchor sites 545. FIG. 5I shows a schematic perspective view of the first surface 505 disposed toward a mal-coapting native leaflet. FIG. 5J shows a schematic cross-sectional view including the anchor 800.

In some embodiments, the leaflet anchor sites 545 comprise one or more barbs having a sharpened tip. The leaflet anchor sites 545 may be a passive anchor. In some embodiments, the coaptation assistance element 500 can include one or more retractable barbs. For instance, the leaflet anchor sites 545 can be retracted during delivery of the coaptation assistance element 500. For instance, the leaflet anchor sites 545 can be advanced after the coaptation assistance element 500 is positioned relative to the anatomical structures. In some embodiments, the leaflet anchor sites 545 are actively retracted and/or advanced. For instance, the delivery catheter described herein can include a mechanism coupled to the leaflet anchor sites 545 designed to retract and/or advance the barbs. In other embodiments, the leaflet anchor sites 545 are passively advanced and/or retracted. In some embodiments, the leaflet anchor sites 545 can be covered by the valve body covering as described herein. In some embodiments, the interface between the tissue and the valve body covering pushes back the valve body covering and exposes the leaflet anchor sites 545. In some embodiments, the tissue dissolves and/or absorbs a portion of the valve body covering and exposes the leaflet anchor sites 545.

In some embodiments, the motion of the purse-string suture, described herein, advances the leaflet anchor sites 545. In some embodiments, the motion of the purse-string suture causes motion of the valve body covering to expose the leaflet anchor sites 545. Other configurations are contemplated.

One or more struts 530 may have one or more barbs along the length of the strut 530. In the illustrated embodiment, five struts 530 each have four leaflet anchor sites 545 along the length of the struts. Other configurations are contemplated varying the number of struts 530 (e.g., one strut, two struts, three struts, four struts, five struts, six struts, seven struts, eight struts, nine struts, ten struts, etc.) and varying the number of leaflet anchor sites 545 per strut 530 (e.g., one barb, two barbs, three barbs, four barbs, five barbs, six barbs, seven barbs, eight barbs, nine barbs, ten barbs, etc.). One or more struts 530 can have the same number of leaflet anchor sites 545. Two or more struts 530 can have a different number of leaflet anchor sites 545. The leaflet anchor sites 545 can be disposed to engage the posterior leaflet.

In some embodiments, the struts 530 may be sandwiched between layers of valve body covering 550. In some embodiments, the struts 530 may be attached to or embedded in the first surface 505 or the second surface 515 of a single layer of valve body covering 550. In some embodiments, the struts 530 may be "stitched" through the valve body covering 550. The first surface 505 can include one or more openings for the leaflet anchor sites 545. In other embodiments, the leaflet anchor sites 545 can push through the valve body covering 550. The leaflet anchor sites 545 can have a pre-set curve which can exert a force on the first surface 505. The leaflet anchor sites 545 can be sharpened to cut through the valve body covering 550.

The frame 565 can have many advantages. The frame 565 can be formed from a flattened pattern. The frame 565 can include an edge which forms the annular hub 520. The edge can include a longitudinal strip or backing 585. One or more struts 530 can extend from the backing 585. In the illustrated embodiment of FIGS. 5C and 5D, the one or more struts 530 are perpendicular to the longitudinal strip. The struts 530 are generally parallel. In some embodiments, the struts 530 are generally perpendicular to the backing 585 that forms the annular hub 520. In some embodiments, the struts 530 form an angle with the backing 585. For instance, the longitudinal axis of the struts 530 can form an acute angle with the backing 585. The angle can aid in the collapse of the struts 530 into the delivery catheter.

The frame 565 can be constructed from a single, planar sheet of material. The frame 565 can be precisely cut using water jet, laser etching or similar technology. The details of the struts 530, including barbs, can be machined into the struts 530. The frame 565 can be bent and/or shape set to achieve the desired geometry. In some embodiments, the backing 585 is folded to form a loop. The frame 565 can be rolled into a tubular shape. The backing 585 can be welded or otherwise secured. The backing 565 when secured end to end to form a loop can be considered the annular hub 520.

The struts 530 are bent to the desired configuration. The struts 530 can form one or more curves. The struts 530 can have one or more inflection points. The struts 530 can have concave portions and/or convex portions. One or more struts 530 can include a radially outward flare beginning at an inflection point. In some embodiments, the superior edge 540 is curved upward away from the inferior edge 580. In some embodiments, the superior edge 540 is curved downward toward the inferior edge 580. In some embodiments, one or more struts 530 can be substantially flat. The struts 530 near the commissures can be substantially flat. In some embodiments, the inferior edge 580 is curved backward toward the superior edge 540. In some embodiments, the inferior edge 580 is curved forward away from the superior edge 540.

The struts 530 can be equally spaced about the circumference of the annular hub 520. The struts 530 can be unequally spaced about the circumference of the annular hub 520. The struts 530 extending along a portion of the circumference of the annular hub 520 are different than struts extending along another portion of the circumference of the annular hub 520. One or more designated portions of the struts 530 can be designed to be placed near the annular region of the heart. One or more designated portions of the struts 530 can be designed to be placed near the commissure region of the heart. One or more designated portions of the struts 530 can be designed to be placed near the ventricular region of the heart. The geometry of the radially extending struts 530 can be shaped to match the geometry of the patient. In some embodiments, the geometry is patient specific. The operator can shape one or more struts 530 based on the geometry of the heart. The operator can modify the shape of one or more struts 530 based on the geometry of the patient.

Figure 5K:
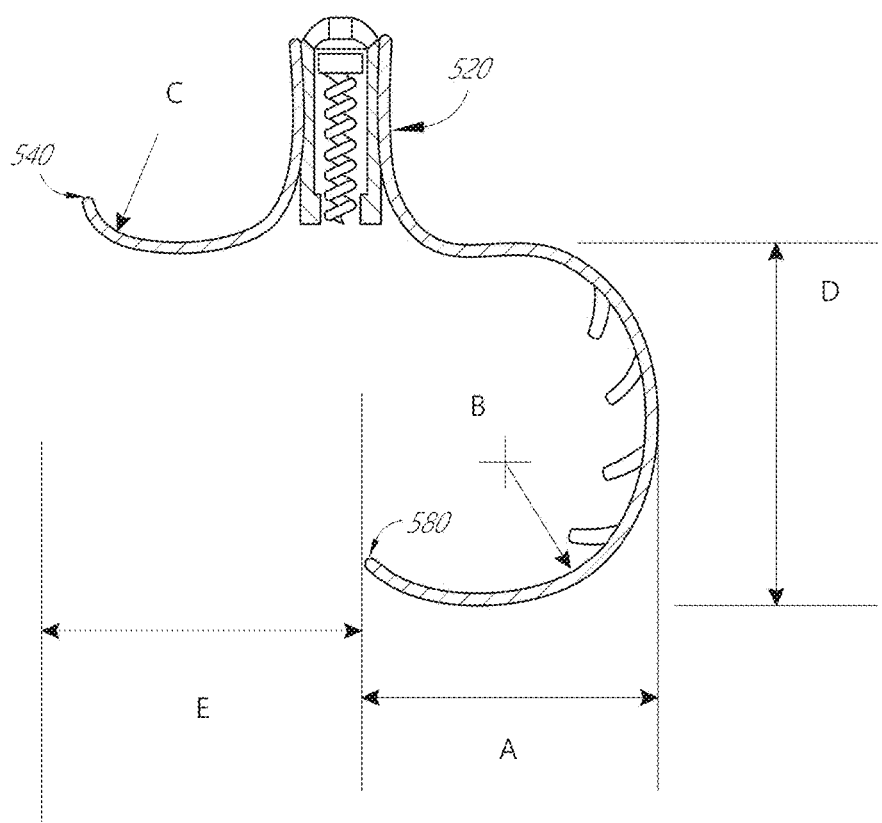
FIG. 5K illustrates dimensions of the coaptation assistance element of FIG. 5A.

FIG. 5K illustrates dimensions of the coaptation assistance element 500. The coaptation assistance element 500 can include a dimension A. The dimension A can be a linear projected dimension or posterior projection. In some embodiments, the range of dimension A can be 1 mm to 40 mm. In some embodiments, the range of dimension A can be 4 mm to 24 mm. Other configurations of the range of dimension A are contemplated e.g., 5 mm to 35 mm, 10 mm to 30 mm, 15 mm to 25 mm, about 1 mm, about 2 mm, about 3 mm, about 4 mm, about 5 mm, about 6 mm, about 7 mm, about 8 mm, about 9 mm, about 10 mm, 1 mm to 10 mm, 5 mm to 15 mm, 10 mm to 20 mm, 15 mm to 25 mm, 20 mm to 30 mm, 25 mm to 35 mm, 30 mm to 40 mm, etc. The dimension A can be 0 mm if no posterior projection, for instance if the coaptation assistance element 500 is straight.

The coaptation assistance element 500 can include a dimension B. In some embodiments, the dimension B can be a radius of curvature. The radius of curvature can be concave or convex, as described herein. In some embodiments, the range of dimension B can be $1/16$ inch to $1/2$ inch. In some embodiments, the range of dimension B can be 1.5 mm to 13 mm. In some embodiments, the range of dimension B can be $1/4$ inch to $3/8$ inch. In some embodiments, the range of dimension B can be 6 mm to 9.5 mm. In some embodiments, the range of dimension B can be 1 mm to 15 mm. Other configurations of the range of dimension B are contemplated e.g., 2 mm to 14 mm, 3 mm to 13 mm, 4 mm to 12 mm, 5 mm to 11 mm, 6 mm to 10 mm, 7 mm to 9 mm, about 1 mm, about 2 mm, about 3 mm, about 4 mm, about 5 mm, about 6 mm, about 7 mm, about 8 mm, about 9 mm, about 10 mm, 1 mm to 10 mm, 5 mm to 15 mm, 10 mm to 20 mm, etc. The dimension B can be 0 mm if no curvature, for instance if the coaptation assistance element 500 is straight.

The coaptation assistance element 500 can include a dimension C. In some embodiments, the dimension C can be a radius of curvature near the superior edge 540. In some embodiments, the range of dimension C can be 1 mm to 10 mm. In some embodiments, the range of dimension C can be 1 mm to 5 mm. Other configurations of the range of dimension C are contemplated e.g., 2 mm to 9 mm, 3 mm to 8 mm, 4 mm to 7 mm, 5 mm to 6 mm, about 1 mm, about 2 mm, about 3 mm, about 4 mm, about 5 mm, about 6 mm, about 7 mm, about 8 mm, about 9 mm, about 10 mm, 1 mm to 15 mm, 5 mm to 10 mm, 3 mm to 9 mm, etc. The dimension C can be 0 mm if no curvature, for instance if the coaptation assistance element 500 is straight.

The coaptation assistance element 500 can include a dimension D. The dimension D can be a coaptation element height. The dimension D can correspond to the distance between the inferior edge 580 and the atrial anchor site or annular hub 520 as measured perpendicular to the plane defined by the annulus of the valve. In some embodiments, the range of dimension D can be 10 mm to 80 mm. In some embodiments, the range of dimension D can be 40 mm to 55 mm. Other configurations of the range of dimension D are contemplated e.g., 5 mm to 105 mm, 10 mm to 100 mm, 15 mm to 95 mm, 20 mm to 90 mm, 25 mm to 85 mm, 30 mm to 80 mm, 35 mm to 75 mm, 40 mm to 70 mm, 45 mm to 65 mm, 50 mm to 60 mm, about 10 mm, about 20 mm, about 30 mm, about 40 mm, about 50 mm, about 60 mm, about 70 mm, about 80 mm, about 90 mm, about 100 mm, 10 mm to 50 mm, 20 mm to 60 mm, 30 mm to 70 mm, 40 mm to 80 mm, 50 mm to 90 mm, 60 mm to 100 mm, 70 mm to 110 mm, etc.

The coaptation assistance element 500 can include a dimension E. The dimension E can be a linear projected dimension or anterior projection. In some embodiments, the range of dimension E can be 2 mm to 20 mm. In some embodiments, the range of dimension E can be 5 mm to 10 mm. Other configurations of the range of dimension E are contemplated e.g., 0 mm to 25 mm, 5 mm to 20 mm, 10 mm to 15 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, 1 mm to 10 mm, 5 mm to 15 mm, 10 mm to 20 mm, 15 mm to 25 mm, 20 mm to 30 mm, 25 mm to 35 mm, 30 mm to 40 mm, etc. The dimension E can be 0 mm if no anterior projection.

The struts 530 of the coaptation assistance element 500 can form a posterior curve of the coaptation surface 560. The posterior bend can have a bend length of the distal 30-100% of the strut. In some embodiments, the posterior bend can have a bend length of at least the distal 40% of the strut. The angle of the posterior bend can be in the range of 0 degrees to 90 degrees with respect to the longitudinal axis of the coaptation assistance element 500. In some embodiments, the angle of the posterior bend can be in the range 45 degrees to 90 degrees.

FIG. 6 illustrates an embodiment of a coaptation assistance element 600. The coaptation assistance element 600 can be similar to the coaptation assistance element 500, and include any features of the coaptation assistance element 500 described herein, with certain additional features described below.

The coaptation assistance element 600 can include an annular hub 620 engaging an annular anchor (not shown). The annular hub 620 may have a built-in or coupled annular anchor, such as annular anchor 800 described herein. The annular anchor may include a helix rotatable with respect to the annular hub 620. In some embodiments, the coaptation assistance element 600 can include a single annular anchor inside the annular hub 620. The coaptation assistance element 600 can be delivered percutaneously as described herein by attachment of a delivery catheter to the annular hub 620.

As may be seen in FIG. 6, the coaptation assistance element 600 can include struts 630. In some embodiments, one, two, or more struts 630 have one end terminating at the annular hub 620 and the other end extending radially outwardly toward the superior edge 640, the lateral edges 670 and 675, and the inferior edge 680 of the coaptation assistance element 600. The struts 630 may extend outward from the hub 620. The struts 630 may be arranged generally parallel to the longitudinal axis of the coaptation assistance element 600 to assist in maintaining the shape of the coaptation assistance element 600 upon placement. The struts 630 may allow the coaptation assistance element 600 to assume a reduced configuration for deployment through a catheter.

The coaptation assistance element 600 can include an annular section 610. The annular section 610 can be positioned above the annulus of the native leaflet when the coaptation assistance element 600 is deployed and form a lip as shown. In some embodiments, the annular section 610 may be may be curved upwardly, e.g., away from the annulus and in a direction substantially opposite from, and substantially parallel to the coaptation surface 660, and form the superior-most portion of the coaptation assist element 600 when implanted. The annular section 610 can be convex. In other embodiments, the annular section 610 may be may be substantially flat with respect to the annulus. One or more of the struts 630 may curve laterally from the annular hub 620 toward the superior edge 640 to assist in maintaining the shape of the annular section 610 of the coaptation assistance element 600 upon deployment. The coaptation assistance element 600 can curve upward from the annular hub 620. In some embodiments, the superior edge 640 does not rest against the posterior leaflet. The superior edge 640 can include an annular radius of curvature. The annular curve radius can curve away from the annulus. The annular curve radius can curve toward the coaptation surface 660. In some embodiments, the annular curve radius can be between 0 mm-5 mm, 5 mm-10 mm, 10 mm-15 mm, 15 mm-20 mm, 20 mm-25 mm, 25 mm-30 mm, etc., or ranges incorporating any two of the previous values. The coaptation assistance element body covering 650 may be similar to the coaptation assistance element body covering 550 described herein.

In some embodiments, the perimeter of the annular section 610 is cupped upward and in a direction substantially opposite to the longitudinal axis of the coaptation surface 660. In some embodiments, the coaptation assistance element 600 includes annular anchor site similar to annular anchor site 535. In other embodiments, the coaptation assistance element 600 does not include annular anchor site as shown in FIG. 6.

FIGS. 7A-7E illustrate an embodiment of a coaptation assistance element 700. The coaptation assistance element 700 can be similar to the coaptation assistance elements 500 or 600, and can include any feature described herein, with certain elements described below.

Figure 7A:
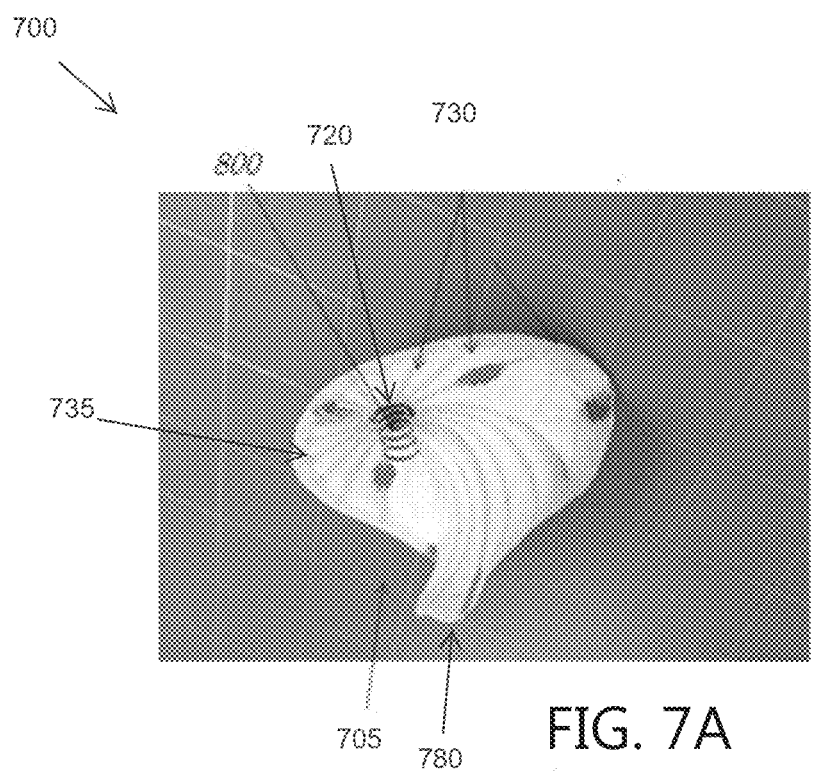
FIG. 7A illustrates a perspective view of an embodiment of a coaptation assistance element showing a first surface disposed toward a mal-coapting native leaflet.
Figure 7B:
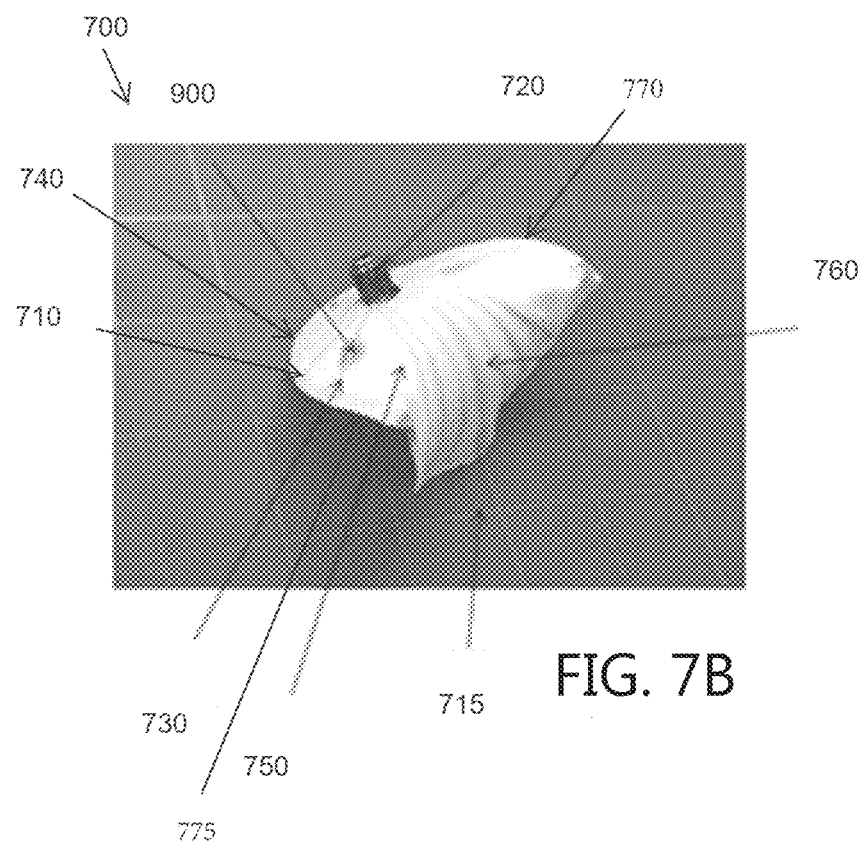
FIG. 7B illustrates another perspective view of the coaptation assistance element of FIG. 7A showing a second surface which can include a coaptation surface.
Figure 7C:
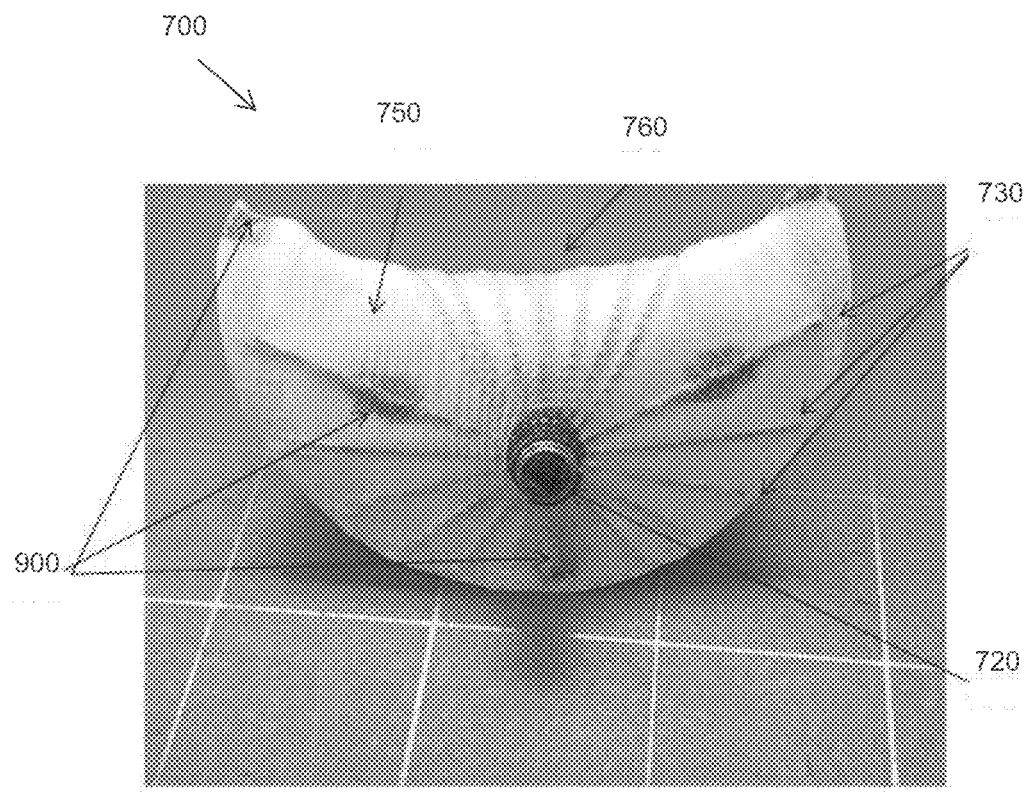
FIG. 7C illustrates a top view of the coaptation assistance element of FIG. 7A.

The coaptation assistance element 700 can include a first surface 705 and a second surface 715. FIG. 7A illustrates a perspective view of the first surface 705 or inferior surface disposed toward a mal-coapting native leaflet, in the instance of a mitral valve, the posterior leaflet. FIG. 7B illustrates a perspective view of the second surface 715 or superior surface which may be disposed toward the anterior leaflet. The second surface 715 can include a coaptation surface 760. The superior edge 740 of the coaptation assistance element 700 may be curved to match the general shape of the annulus or adjoining atrial wall. The superior edge 740 can be curved downward, toward the posterior leaflet, as shown in FIG. 7B. FIG. 7C illustrates a top view of the coaptation assistance element 700.

FIGS. 7A-7C show a view of the coaptation assistance element 700 with an annular hub 720. The coaptation assistance element 700 can include the annular hub 720 designed to engage the annular anchor 800. The annular anchor 800 may be engaged at a proximal end by a driver, described herein. The annular hub 720 may have a built-in or coupled annular anchor 800. The annular anchor 800 may comprise a helix rotatable with respect to the annular hub 720. The coaptation assistance element 700 can be delivered percutaneously as described herein by attachment of a delivery catheter to the annular hub 720.

As may be seen in FIGS. 7A-7C, the coaptation assistance element 700 can include struts 730. In some embodiments, one or more struts 730 have one end terminating at the annular hub 720 and the other end extending radially outwardly toward the superior edge 740, the lateral edges 770 and 775, and the inferior edge 780 of the coaptation assistance element 700 shown in FIG. 7B. The annular anchor site 735 is shown extending downward from the body of the coaptation assistance element 700 in FIG. 7B. The annular anchor 800 can be an active anchor. The annular anchor sites 735 can be a passive anchor, such as barbs. The annular anchor sites 735 can be at the distal ends of one or more struts 730.

The annular section 710 can be positioned above the native leaflets when the coaptation assistance element 700 is deployed. In some embodiments, the annular section 710 may be may be curved toward the annulus or atrial wall. One or more of the struts 730 may curve laterally from the hub 720 toward the superior edge 740 to assist in maintaining the shape of the annular section 710 of the coaptation assistance element 700 upon deployment. The coaptation assistance element 700 can curve downward from the annular hub 720 toward the annular anchor site 735. The annular section 710 can be concave. In some embodiments, one or more support structures may be provided which run parallel to the superior edge 740 of the coaptation assistance element 700 and assist in maintaining the shape of the superior edge 740. The struts 730 and/or other support structures of the frame can be laser-cut from a Nitinol tube in some embodiments. The valve body covering 750 may be comprised of a material as described herein.

In some embodiments, the coaptation assistance element 700 includes an active anchor such as annular anchor 800. In some embodiments, the coaptation assistance element 700 includes a passive anchor such as annular anchor site 735. The annular anchor site 735 can include barbs at the tip of one or more struts 730.

The coaptation assistance element 700, as well as any coaptation assistance element 500, 600 described herein, can include one or more markers 900. The marker 900 can be positioned on any portion of the coaptation assistance element 500, 600, 700 or any element thereof, such as the struts 530, 630, 730, the annular hub 520, 620, 720, the purse-string suture 1010, and/or the annular anchor sites 535, 735. In some embodiments, the marker 900 is positioned on the annular anchor 800. In other embodiments, the marker 900 is integrally formed with the coaptation assistance element 500, 600, 700 or the annular anchor 800. A plurality of markers 900 can be arranged in specific patterns, on the coaptation assistance element, to provide a fluoroscopic visual aid for the operator to accurately orient and position the coaptation assistance element 500, 600, 700 and/or the annular anchor 800 within the heart of a patient.

In some embodiments, the markers 900 may be radio-opaque or they may be covered by a radio graphic marker. During the process of delivery of the coaptation assistance element 500, 600, 700 and/or the annular anchor 800, the markers 900 may be visualized if a fluoroscope is used. The marker 900 can help position the coaptation assistance element 500, 600, 700 and/or the annular anchor 800 within the heart of a patient. In some embodiments, torque can be applied to the annular anchor 800 such that the annular anchor 800 is driven into the tissue. To provide feedback whether the annular anchor 800 is secured appropriately, fluoroscopic markers 900 may be present on the annular anchor 800. The markers may be located at the proximal end. These markers 900 may inform the medical team about how far the annular anchor 800 may have traveled towards the annular hub 520, 620, 720 and may be informative about when the annular anchor 800 is securely in place. In some embodiments, to ensure that appropriate torque is applied, the torque level at a handle may spike as the annular anchor 800 bottoms out on the annular hub 520, 620, 720. The systems described herein can include one or more markers 900 (e.g., one, two, three, four, five, six, seven, eight, nine, ten, more than one, more than two, more than three, more than four, etc.). The systems described herein can include two or more different markers 900. The different markers can indicate different components of the system, different portions of the coaptation assistance element 500, 600, 700 or positioning points such as the most proximal point, most distal point, midline, etc.

Figure 7D:
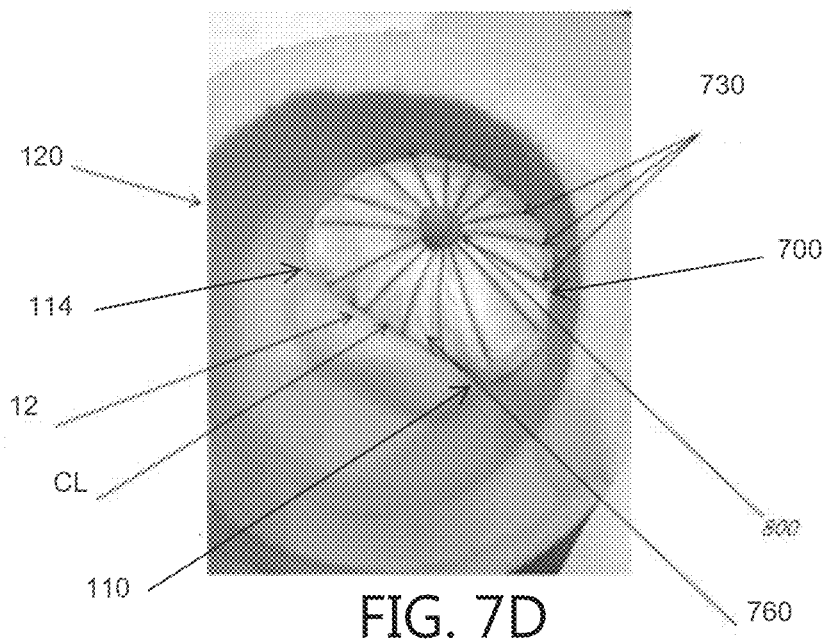
FIG. 7D illustrates the coaptation assistance element of FIG. 7A implanted within a model of a mitral valve.
Figure 7E:
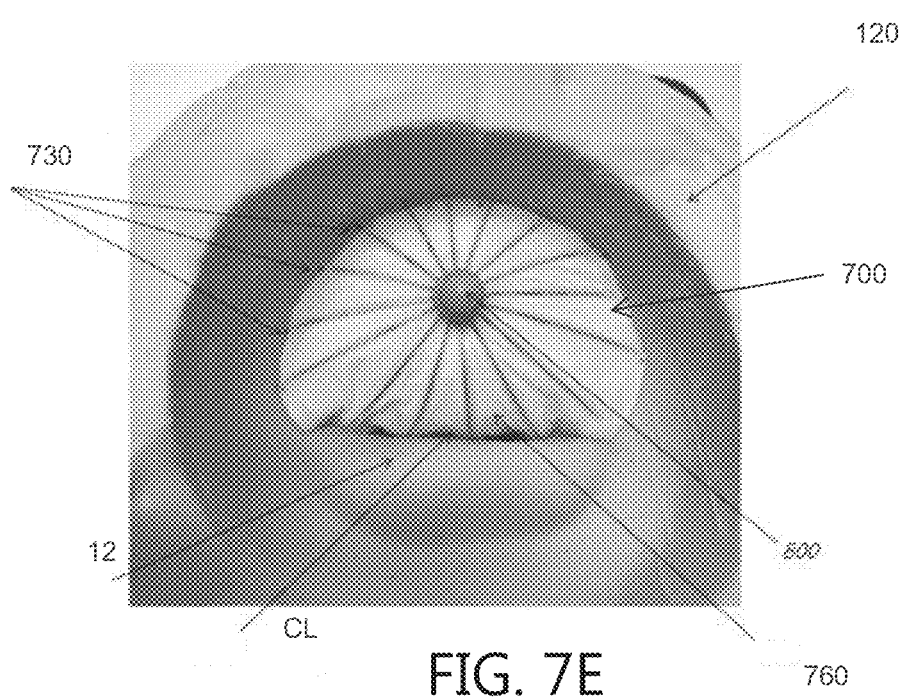
FIG. 7E illustrates a top view of the coaptation assistance element of FIG. 7A implanted within a model of a mitral valve.

FIGS. 7D-7E illustrate an embodiment of the coaptation assistance element 700 deployed within the heart mitral valve model. Referring back to FIG. 1F, the coaptation zone CL between the leaflets is not a simple line, but rather a curved funnel-shaped surface interface as shown in FIG. 7C. The first 110 (Anterio-lateral or left) and second 114 (Posterio-medical or right) commissures are where the anterior leaflet 12 meets the posterior leaflet at the coaptation zone, which form the coaptation line (CL). As seen most clearly in the axial views from the atrium of FIG. 7D, an axial cross-section of the coaptation zone generally shows the curved line CL that is separated from a centroid of the annulus as well as from the opening through the valve during diastole. In addition, the leaflet edges are scalloped, more so for the posterior versus the anterior leaflet. Mal-coaptation can occur between one or more of these A-P (anterior-posterior) segment pairs A1/P1, A2/P2, and A3/P3, so that mal-coaptation characteristics may vary along the curve of the coaptation zone CL, as shown in FIG. 1F.

In some embodiments, the coaptation assistance element 700 is placed over the posterior leaflet to create a new surface onto which the native leaflet, here the anterior leaflet, can coapt. The mitral valve is shown with the anterior leaflet 12. The zone of coaptation occurs between the anterior leaflet 12 and the coaptation surface 760 of the coaptation assistance element 700.

Figure 8A:
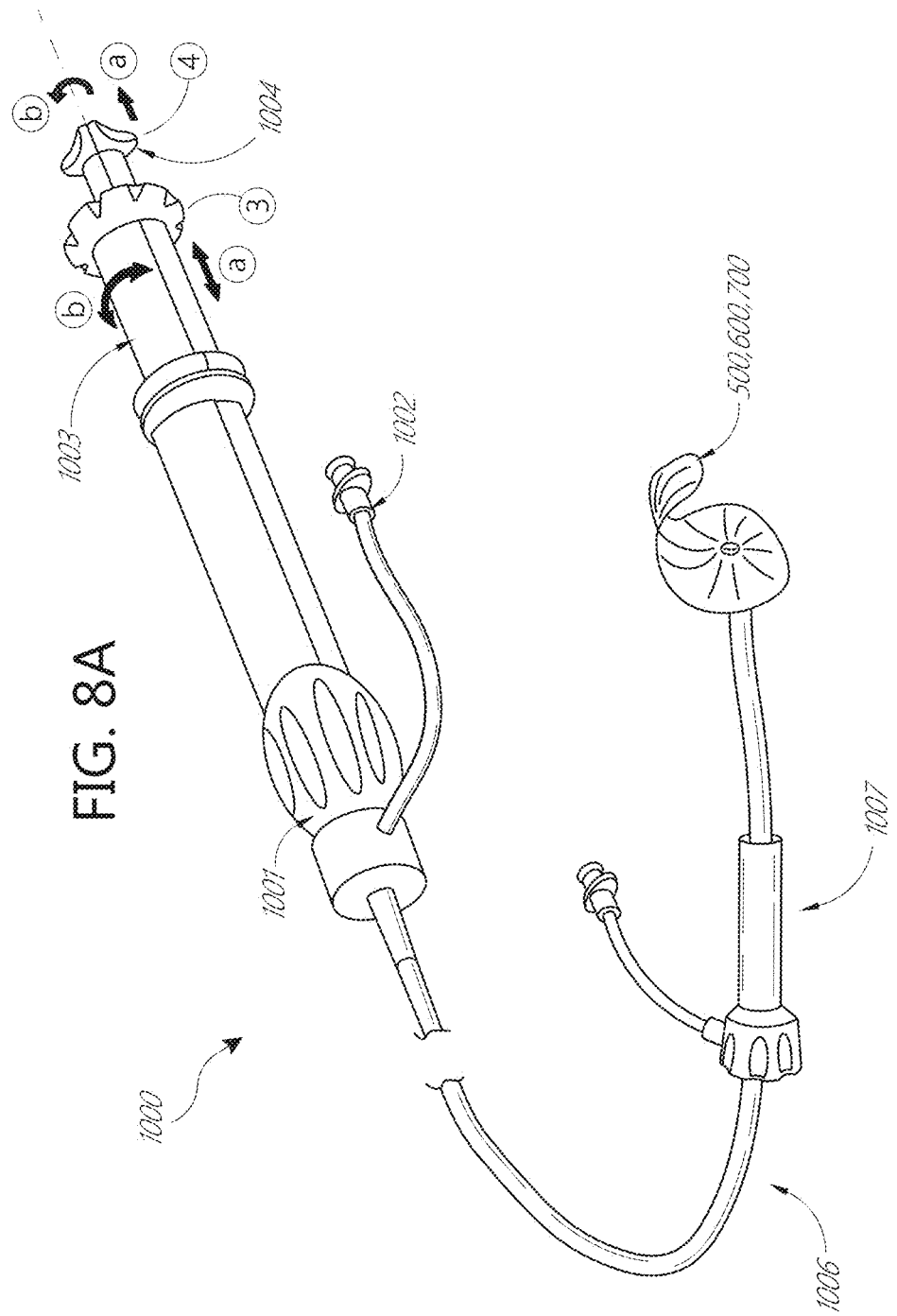
FIG. 8A schematically illustrates an embodiment of control handle of a delivery system for a transcatheter technique.

Referring now to FIG. 8A, aspects of the delivery catheter 1000 are illustrated. The delivery catheter 1000 can include a control handle. The delivery catheter 1000 can include a tip deflection control 1001. The tip deflection control 1001 can allow a distal portion of the delivery catheter 1000 to deflect. This may be advantageous to place the coaptation assistance element 500, 600, 700 within the mitral valve. The delivery catheter 1000 can be inserted into a transseptal sheath (not shown). The transseptal sheath allows the introduction of the delivery catheter into the left atrium. The delivery catheter 1000 may further include one or more ports 1002, such as a flush, irrigation and/or aspiration port to remove the air from the system and allow injection of fluids such as saline or contrast media to the site of implantation. The catheter 1000 can include a catheter shaft 1006. The catheter 1000 can include an implant inserter 1007.

The delivery catheter 1000 may include an implant control knob 1003. The implant control knob 1003 can control the movements of the coaptation assistance element 500, 600, 700. The implant control knob 1003 may enable the collapse of the coaptation assistance element 500, 600, 700. The implant control knob 1003 may enable the expansion of the coaptation assistance element 500, 600, 700. The arrow 1003a indicates the direction of movement of the implant control knob 1003 for the coaptation assistance element 500, 600, 700 to be collapsed by the delivery catheter 1000 and/or expanded by the delivery catheter 1000. The implant control knob 1003 may enable the rotation of the coaptation assistance element 500, 600, 700. The arrow 1003b indicates the direction of movement of the implant control knob 1003 for the coaptation assistance element 500, 600, 700 to be rotated.

The implant control knob 1003 can be internally connected to the coaptation assistance element 500, 600, 700 to allow the transmission of axial movement and/or torque. For instance, the implant control knob 1003 of the delivery catheter 1000 can be coupled to the annular hub 520, 620, 720 For instance, the implant control knob 1003 can be connected to one or more purse-string suture 1010 which may control the deployment of the coaptation assistance element 500, 600, 700. The purse-string suture 1010 may facilitate the collapse and/or expansion of the coaptation assistance element 500, 600, 700 as described herein. The purse-string suture 1010 may facilitate the rotation of the coaptation assistance element 500, 600, 700 as described herein. In some embodiments, the delivery catheter 1000 releasably engages coaptation assistance element 500, 600, 700 such that axial movement and torque can be transmitted from the delivery catheter 1000 to the coaptation assistance element 500, 600, 700

In some embodiments, a tip 1300 of the delivery catheter 1000 is releasably coupled to the annular hub 520, 620, 720 For instance, the tip 1300 of the delivery catheter 1000 can lock onto the annular hub 520, 620, 720 such that movement of the delivery catheter 1000 causes movement of the coaptation assistance element 500, 600, 700. In some embodiments, the system includes a release mechanism between the delivery catheter 1000 and the annular hub 520, 620, 720.

Figure 8C:
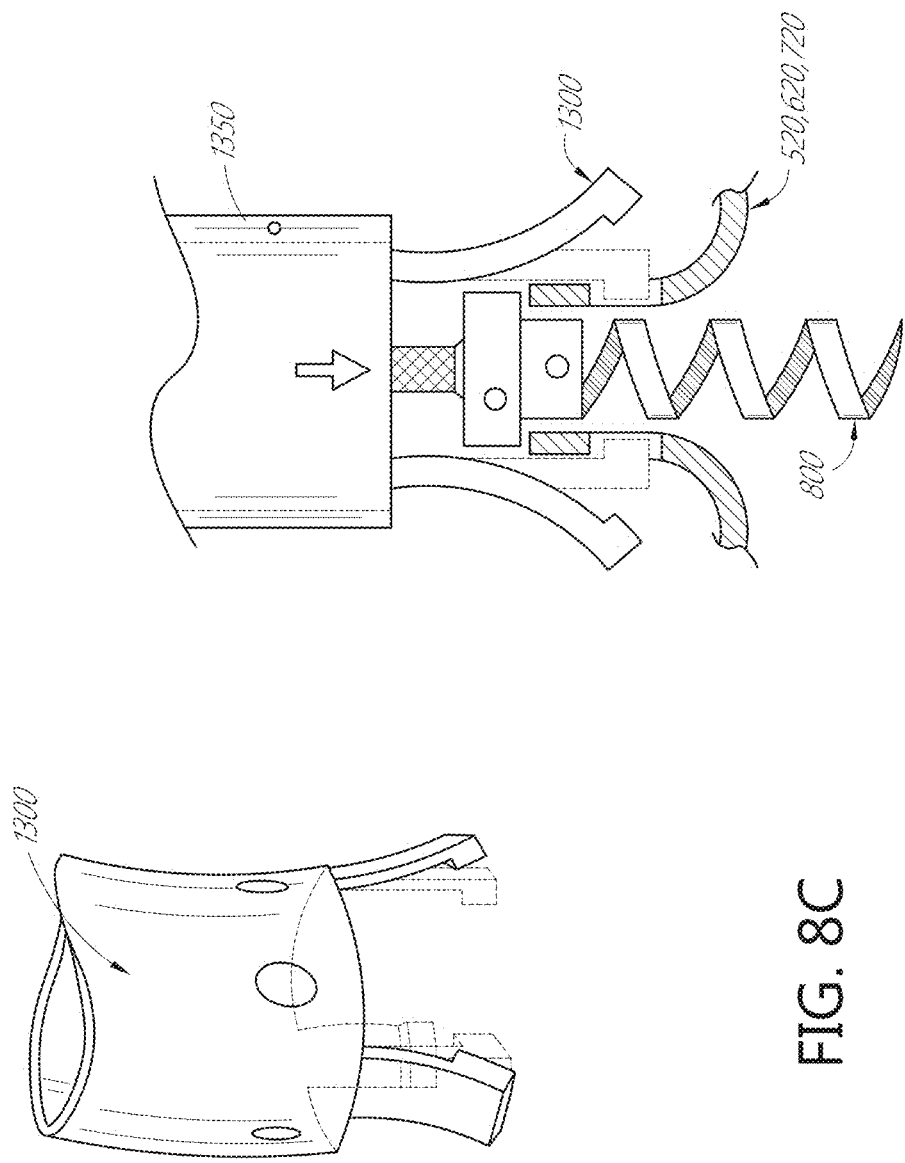
FIG. 8C schematically illustrates the connection between an annular hub of the coaptation assistance element and a tip of the delivery catheter.
Figure 9A:
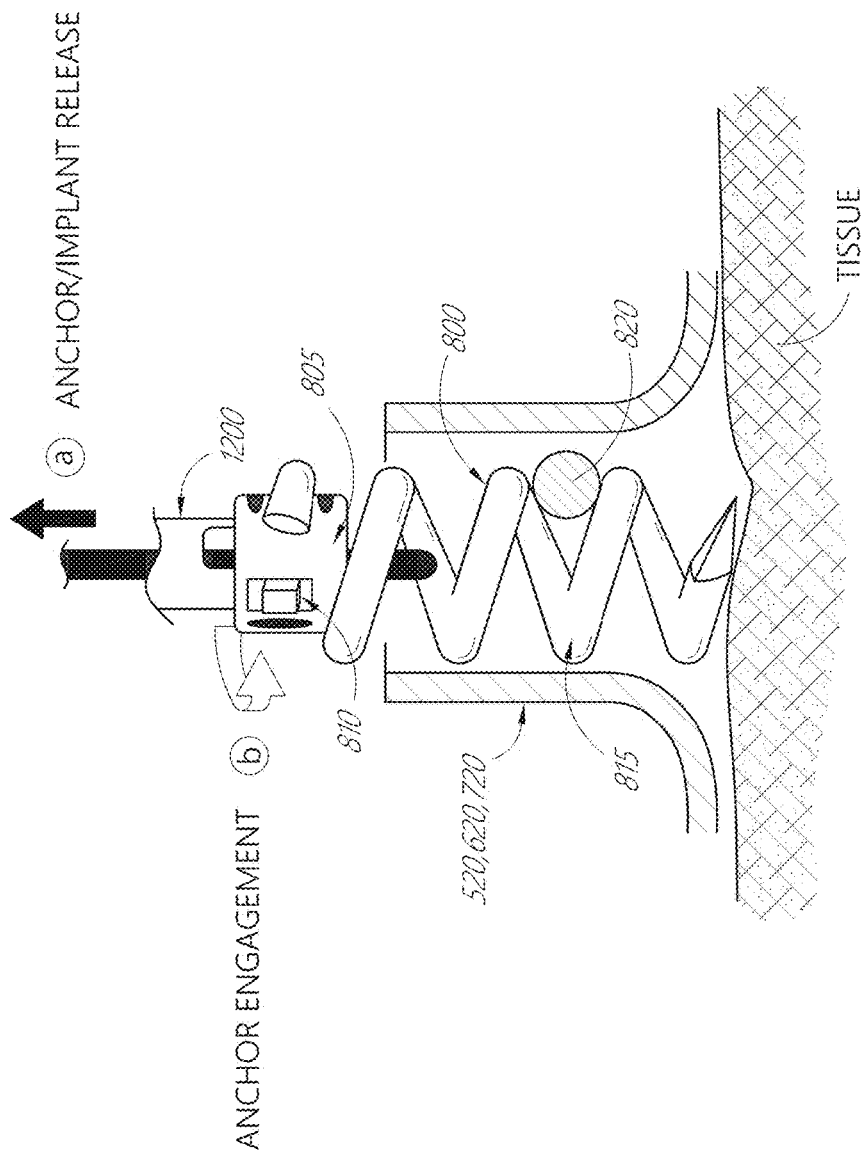
FIG. 9A schematically illustrates the anchor manipulation of the delivery system of FIG. 8A.

The annular hub 520, 620, 720 may have features, which can lock with the tip 1300 of the delivery catheter 1000. Referring back to FIGS. 5A-7E, the annular hub 520, 620, 720 can include one or more features to engage a portion of the delivery catheter 1000. The feature can include one or more notches in the hub 520 of the Implant as shown in FIG. 5A. The feature can include an internal lip as shown in FIG. 9A. The feature can include windows accessible from the outside of the hub 520, 620, 720, as shown in FIG. 8C. The feature can include any structure or mechanism capable of coupling the annular hub 520, 620, 720 and a portion of the delivery catheter 1000. In some embodiments, the annular hub 520, 620, 720 and the delivery catheter 1000 are coupled via a screw mechanism. For instance, the annular hub 520, 620, 720 can include a female thread and the distal end of the delivery catheter 1000 can include a male thread. In some embodiments, the annular hub 520, 620, 720 and the delivery catheter 1000 are coupled via a noose and pin configuration. For instance, the annular hub 520, 620, 720 can include a pin such as an outwardly extending pin and the distal end of the delivery catheter 1000 can include a loop or noose designed to be tightened around the pin. Other configurations are contemplated.

Figure 8B:
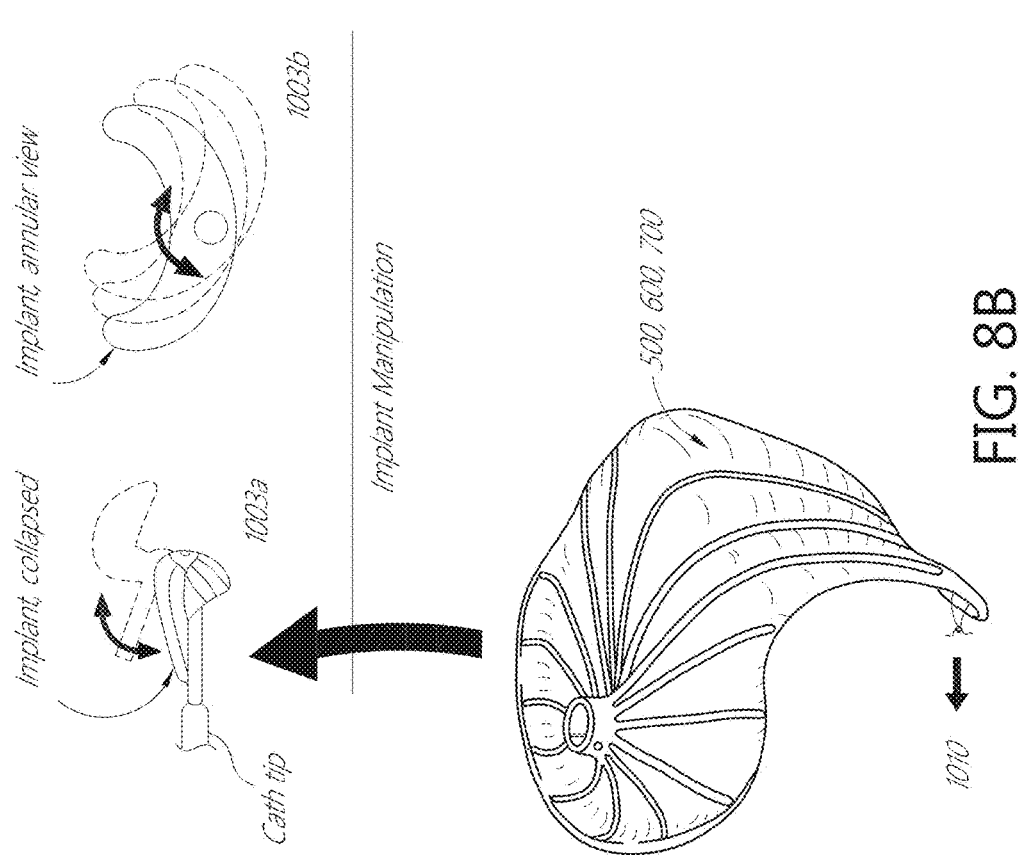
FIG. 8B schematically illustrates a top view and a side view a coaptation assistance element coupled to the delivery system of FIG. 8A.

FIG. 8B shows the coaptation assistance element 500, 600, 700 coupled to the delivery catheter 1000. The coaptation assistance element 500, 600, 700 can be collapsed as shown or expanded as shown by the dashed lines by movement along arrow 1003a. The coaptation assistance element 500, 600, 700 can be rotated as shown by the dashed lines by movement along arrow 1003b.

Referring to FIG. 8C, the delivery catheter 1000 can include the tip 1300. The distal end of the tip 1300 can include distal locking tabs. In some embodiments, the tip 1300 includes a plurality of pre-bent or shape-set locking tabs. In some embodiments, the tip includes two locking tabs, three locking tabs, four locking tabs, five locking tabs, a plurality of locking tabs, a multitude of locking tabs, etc. This "AT-lock" (axial-torsional lock) can include nitinol locking tabs on the tip 1300. In some embodiments, the locking tabs of the tip 1300 can be actuated by a sheath 1350. In some embodiments, the sheath 1350 is hollow to allow movement of other components such as the driver described herein. The movement sheath 1350 can force the locking tabs inward into engagement with the annular hub 520, 620, 720. In some embodiments, the locking tabs of the tip 1300 engage a feature such as a window or lip of the annular hub 520, 620, 720. In some embodiments, movement of the sheath 1350 in the opposite direction can cause the release of the annular hub 520, 620, 720 from the tip. In other embodiments, the locking tabs of the tip 1300 can be actuated by a central pin inserted within tip 1300 (not shown). In some embodiments, the central pin is hollow to allow movement of other components such as the driver described herein. The movement of the central pin can force the locking tabs outward into engagement with the annular hub 520, 620, 720.

In some embodiments, the distal end of the tip 1300 can be actuated to lock the delivery catheter 1000 to the annular hub 520, 620, 720. In some embodiments, the distal end of the tip 1300 can be actuated to unlock the delivery catheter 1000 from the annular hub 520, 620, 720. As described herein, secondary structures such as the purse-string sutures may remain coupled to the coaptation assistance element 500, 600, 700 after the annular hub 520, 620, 720 is released from the tip 1300. In some embodiments, when the delivery catheter 1000 is unlocked, one or more secondary structures such as the purse-string sutures described herein can retain a relative position between the delivery catheter 1000 and the annular hub 520, 620, 720. During a procedure, the tip 1300 may be repeatedly locked and unlocked.

Referring back to FIG. 8A, the delivery catheter 1000 can include the anchor control knob 1004. In some embodiments, the anchor control knob 1004 can enable the release of the annular anchor 800 and/or the coaptation assistance element 500, 600, 700. In some embodiments, the anchor control knob 1004 can enable the engagement of the annular anchor 800 for instance to rotate the annular anchor 800 and/or to axially move the annular anchor 800. In some embodiments, the anchor control knob 1004 can enable the disengagement of the annular anchor 800. In some embodiments, the anchor control knob 1004 can control a driver 1200 configured to apply torque. In some embodiments, the anchor control knob 1004 can control a driver 1200 configured to apply tension and/or release the coaptation assistance element 500, 600, 700. In some embodiments, the anchor control knob 1004 can control a driver 1200 configured to apply tension and torque.

The anchor control knob 1004 of the delivery catheter 1000 may be coupled to the annular anchor 800 to allow transmission of torque to the annular anchor 800. The anchor control knob 1004 may enable simple manipulation of the torque or position of the annular anchor 800. The arrow 1004*a* indicates the direction of movement of the anchor control knob 1004 for the annular anchor 800 to be engaged or disengaged. For instance, moving the anchor control knob 1004 toward the annular anchor 800 may engage a driver 1200 with the annular anchor 800. The arrow 1004*b* indicates the direction of movement of the anchor control knob 1004 for the transmission of torque to the annular anchor 800. In some embodiments, the arrow 1004*b* indicates the direction to release the annular anchor 800. For instance, the further application of torque may twist the driver 1200 out of engagement with the annular anchor 800.

An embodiment of an annular anchor 800 is illustrated in detail in FIG. 9A. Other components of the delivery catheter 1000 are not shown in FIG. 9A, such as the component which engages the annular hub 520, 620, 720. The annular anchor 800 may be coupled to the driver 1200 in various ways, as described herein. The annular anchor 800 may be coupled to the coaptation assistance element 500, 600, 700 in various ways. In some embodiments, the annular hub 520, 620, 720 may have a cross-pin 820. The cross-pin 820 can provide a site about which a helical structure 815 of the annular anchor 800 may wrap around as shown. The annular anchor 800 can have a shoulder 805. The shoulder 805 may fit around the outside of a driver 1200 of the delivery catheter 1000.

In some embodiments, the driver 1200 is releasably coupled to the annular anchor 800. The driver 1200 can be coupled and/or controlled by the anchor control knob 1004 described herein. One or more drivers 1200 can deliver torque to drive the annular anchor 800 into tissue. One or more drivers 1200 can deliver tension to hold and/or release the annular anchor 800. In some embodiments, a single driver 1200 delivers torque and tension. In other embodiments, two or more drivers 1200 deliver torque and tension. For instance, the driver 1200 can lock onto the annular anchor 800 such that movement of the driver 1200 causes movement of the annular anchor 800. In some embodiments, the system includes a release mechanism between the driver 1200 and the annular anchor 800. In some embodiments, the distal end of the driver 1200 can be actuated to lock the driver 1200 to the annular anchor 800. In some embodiments, the distal end of the driver 1200 can be actuated to unlock the driver 1200 from the annular anchor 800. In some embodiments, when the driver 1200 is unlocked, one or more secondary structures such as the purse-string sutures can retain a relative position between the delivery catheter 1000 and the annular anchor 800. During a procedure, the driver 1200 may be repeatedly locked and unlocked.

Figure 9B:
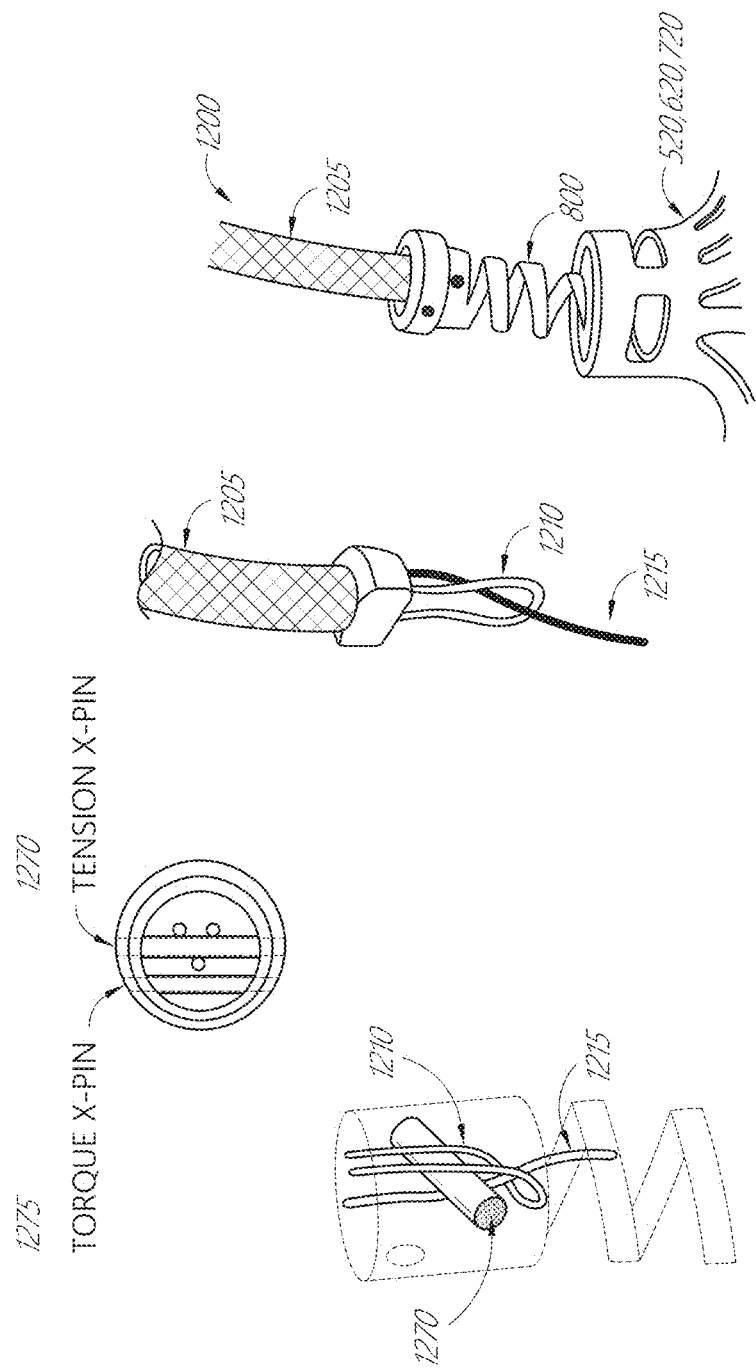
FIGS. 9B-9E schematically illustrates embodiments of the connection between an annular anchor and a driver.

FIG. 9B illustrates an embodiment of a driver 1200. The driver 1200 can include a torque shaft 1205. The torque shaft 1205 can include a loop 1210. The loop 1210 can engage a pin 1215 extending and looping around the tension cross-pin 1270 and through the anchor 800. The rotation of the torque shaft 1205 can cause a torque to be applied to a torque cross-pin 1275, thereby causing rotation of the annular anchor 800. In some embodiments, the annular anchor 800 can include a torque cross-pin and a tension cross-pin. Another driver (not shown) can apply a torque to the tension cross-pin to apply tension to the annular anchor 800. One or more drivers 1200 can engage the annular anchor 800 to deliver torque. One or more drivers 1200 can engage the annular anchor 800 to deliver tension. In some embodiments, delivery of the annular anchor 800 is independent of rotation of the coaptation assistance element 500, 600, 700.

Figure 9C:
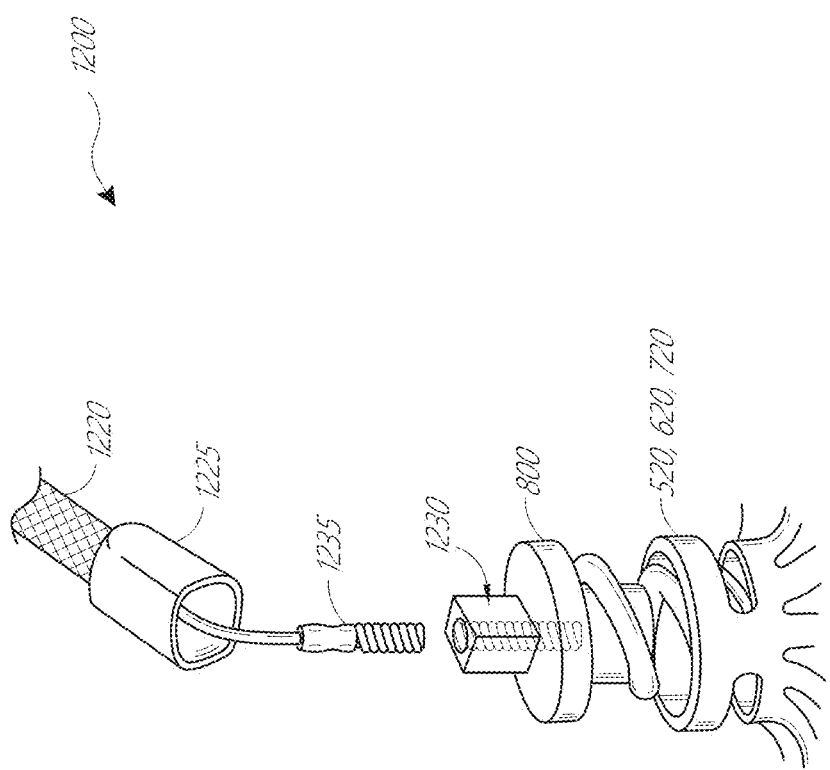

FIG. 9C illustrates an embodiment of a driver 1200. The driver 1200 can include a torque shaft 1220. The torque shaft 1220 can include an anchor docking cap 1225. The anchor docking cap 1225 can engage the annular anchor 800 in a single orientation or one of a plurality of orientations. In some embodiments, the annular anchor 800 includes a protrusion 1230 and the anchor docking cap 1225 is designed to accept the protrusion 1230. In other embodiments, the annular anchor 800 includes a recess (not shown) to accept a mating protrusion on the anchor docking cap 1225 (not shown). The rotation of the torque shaft 1220 can cause a torque to be applied to the annular anchor 800. Another driver 1235 can apply tension to the annular anchor 800. In some embodiments, the driver 1235 can include a release screw. In other embodiments, the loop and pin release mechanism described in FIG. 9B may be used. The release screw can be rotated to release the annular anchor 800. One or more drivers 1200 can engage the annular anchor 800 to deliver torque. One or more drivers 1200 can engage the annular anchor 800 to deliver tension.

Figure 9D:
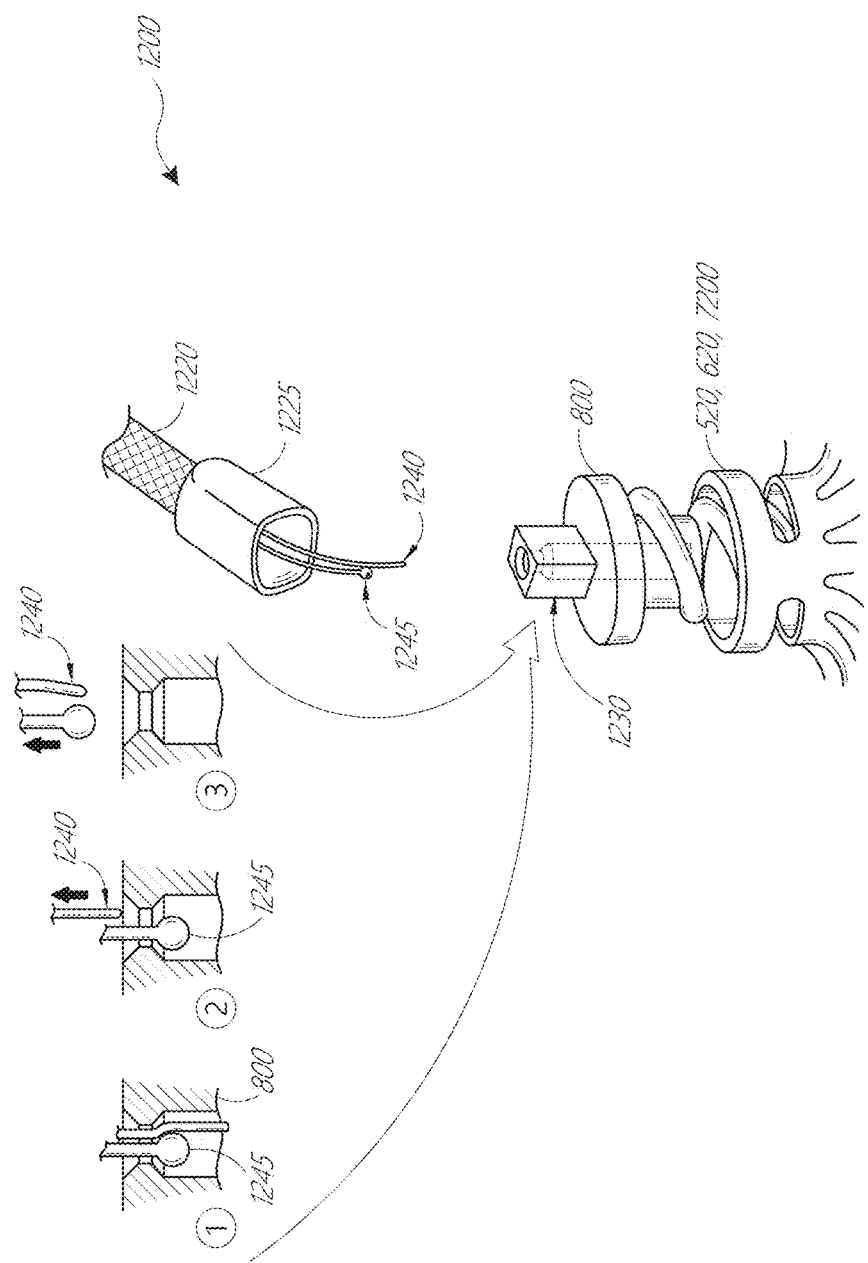
Figure 9E:
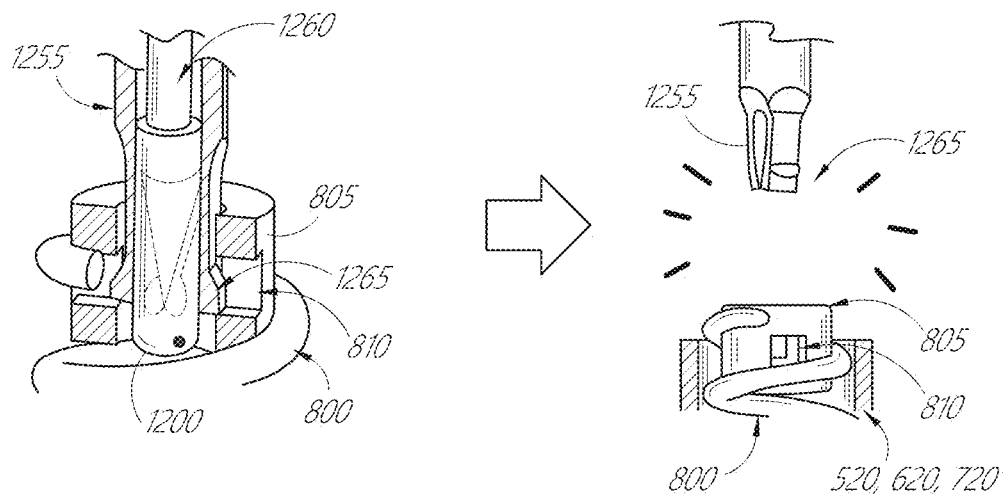

FIG. 9D illustrates an embodiment of a driver 1200 and the annular anchor 800. The driver 1200 can include a torque shaft 1220. The torque shaft 1220 can include an anchor docking cap 1225. In some embodiments, the annular anchor 800 includes a protrusion 1230 and the anchor docking cap 1225 is designed to accept the protrusion 1230. In other embodiments, the annular anchor 800 includes a recess (not shown) to accept a mating protrusion on the anchor docking cap 1225 (not shown). Two or more wires 1240, 1245 can apply tension to the annular anchor 800. In some embodiments, the wire 1240 acts as a pin, and the wire 1245 terminates in a ball. In a retained state, the wires 1240, 1245 are both positioned within an opening in the annular anchor 800. The opening is too small to allow the pin and ball end of wires 1240, 1245 to pass side by side. In some methods of use, the wire 1240 is retracted first. The retraction of the wire 1240 yields sufficient room to allow retraction of the wire 1245. The wires 1240, 1245 can be actuated to release the annular anchor 800. One or more drivers 1200 can engage the annular anchor 800 to deliver torque. One or more drivers 1200 can engage the annular anchor 800 to deliver tension FIG. 9E illustrates an embodiment of the driver 1200. The driver 1200 can include a torque shaft 1255. The shoulder 805 may have features such as windows 810 which can lock with one or more distal locking tabs 1265 of the torque shaft 1255. The distal locking tabs 1265 may include nitinol material such as a Shape-set NiTi clip. The distal locking tabs 1265 may be pushed outward into the windows 810 by a driver 1260. The driver 1260 acts as a release mechanism. The longitudinal movement of the driver 1260 toward the annular anchor 800 may push the distal locking tabs 1265 outward toward the windows 810. The longitudinal movement of the driver 1260 away from the annular anchor 800 may allow the distal locking tabs 1265 to regain a neutral configuration and disengage from the windows 810. The distal locking tabs 1265 engaged with the windows 810 of the annular anchor 800 can allow the transmission of axial movement between the torque shaft 1255 and the annular anchor 800. The distal locking tabs 1265 engaged with the windows 810 of the annular anchor 800 can allow the transmission of torque between the torque shaft 1255 and the annular anchor 800. In embodiments where the annular anchor 800 is built-in or captured by the annular hub 520, 620, 720, the distal locking tabs 1265 engaged with the windows 810 can allow the transmission of axial movement between the delivery catheter and the coaptation assistance element 500, 600, 700.

In some embodiments, an advantage is the annular anchor 800 can be rotated independently of the coaptation assistance element 500, 600, 700. As described herein, the coaptation assistance element 500, 600, 700 is coupled to the delivery catheter 1000. As described herein, the annular anchor 800 is independently coupled to the driver 1200. The annular anchor 800 can be rotated independently of the annular hub 520, 620, 720. The annular hub 520, 620, 720 can remain stationary as the annular anchor 800 is rotated to engage tissue.

In some methods, the annular anchor 800 can be preloaded onto the coaptation assistance element 500, 600, 700 and coupled to the driver 1200 during the process of mounting the coaptation assistance element 500, 600, 700 onto the delivery catheter 1000. This can occur before the coaptation assistance element 500, 600, 700 is pulled into an implant sheath and/or another portion of the delivery catheter 1000 and is being readied for insertion into the femoral vein. As disclosed herein, torque can be applied such that the annular anchor 800 is driven into the tissue. In some embodiments, to ensure that appropriate torque is applied, the torque level at the handle may spike as the annular anchor 800 bottoms out on the annular hub 520, 620, 720. This increased torque level may be felt at the handle providing feedback that appropriate torque has been applied. In other embodiments, radiopaque markings may aid in visually determining the level of anchor engagement within tissue. In some embodiments, the markings can be located on the annular anchor 800 and/or the coaptation assistance element 500, 600, 700.

FIGS. 10-15 show various method steps, which may be performed during a method of use of the coaptation assistance element 500, 600, 700. The method may include the step of collapsing the coaptation assistance element 500, 600, 700. The method may include the step of coupling the coaptation assistance element 500, 600, 700 to the delivery catheter 1000. The method may include the step of coupling the locking tabs 1265 with the annular anchor 800 and/or the coaptation assistance element 500, 600, 700. The method step can include any step disclosed herein for manufacturing the coaptation assistance element 500, 600, 700.

In some embodiments, an advantage is the coaptation assistance element 500, 600, 700 can be delivered with a hub-leading orientation. In this method of use, the annular hub 520, 620, 720 can be moved into position relative to the anatomical structures prior to another portion of the coaptation assistance element 500, 600, 700. In some methods of use, the ventricular end of the coaptation assistance element 500, 600, 700 can be retained within the delivery catheter 1000 until the annular hub 520, 620, 720 is positioned. In some methods of use, once the annular hub 520, 620, 720 and/or the annular anchor 800 are engaged with the tissue, the coaptation assistance element 500, 600, 700 can be expanded. In some methods of use, once the annular hub 520, 620, 720 and/or the annular anchor 800 are engaged with the tissue, the ventricular end of the coaptation assistance element 500, 600, 700 can be positioned.

In some embodiments, an advantage is the coaptation assistance element 500, 600, 700 can be delivered with a strut-leading orientation. In this method of use, one or more of the struts 530, 630, 730 of the coaptation assistance element 500, 600, 700 can be moved into position relative to the anatomical structures prior to another portion of the coaptation assistance element 500, 600, 700. In some methods of use, the coaptation assistance element 500, 600, 700 can be expanded or partially expanded prior to the positioning of the annular hub 520, 620, 720. In some methods of use, the annular hub 520, 620, 720 can be retained within the delivery catheter until one or more of the struts 530, 630, 730 are positioned. In some methods of use, once the struts 530, 630, 730 are positioned, the annular anchor 800 is engaged with the tissue.

Figure 10:
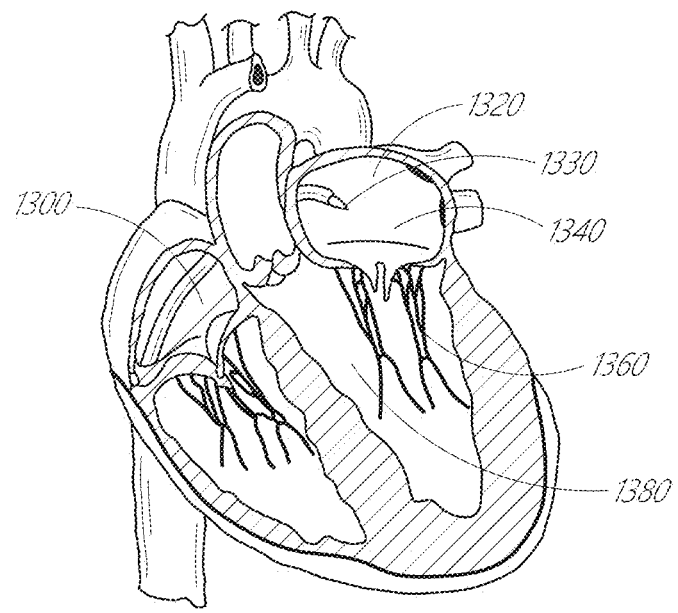
FIG. 10 schematically illustrates a method step for a transcatheter technique showing transseptal crossing.

FIG. 10 illustrates an embodiment of transeptal crossing. The method step may include femoral vein access. Access may be gained through a vessel such as the femoral vein in order to reach a chamber of the heart such as the right atrium 1300. The left ventricle 1380 and its papillary muscles are also shown 1360. The method may include the step of transseptal puncture and crossing with standard transseptal kit 1330 to the left atrium 1320. The method may include the step of exchanging for custom transseptal sheath and delivery catheter 1000, as described herein. A transseptal puncture kit may be exchanged for a transseptal sheath and dilator, and the dilator may be exchanged for an implant delivery catheter which may be as disclosed herein and in U.S. Pat. No. 8,888,843 to Khairkhahan et al., incorporated by reference in its entirety. The method may include the step of removing a dilator. The method may include the step of advancing the delivery catheter 1000. However, other approaches such as transapical, transatrial, femoral artery, brachial artery, and the like are also within the scope of the invention.

Figure 11:
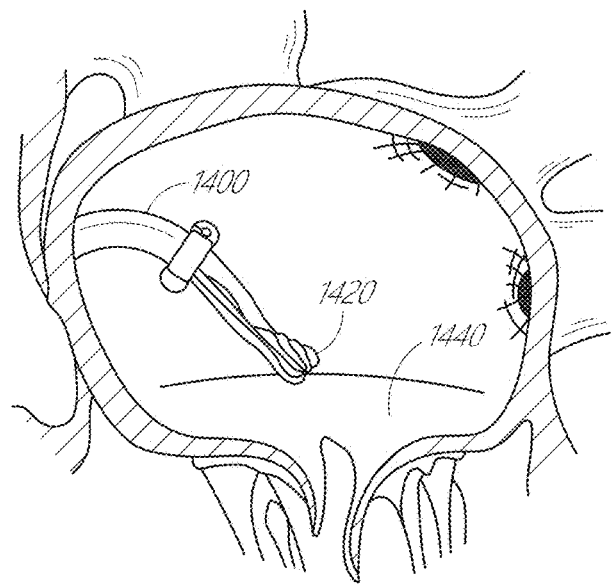
FIG. 11 schematically illustrates a method step for a transcatheter technique showing initial coaptation assistance element advancement.

FIG. 11 illustrates initial advancement of the coaptation assistance element 500, 600, 700. The method may include the step of advancing the coaptation assistance element 500, 600, 700 inside the retrieval sheath. The retrieval sheath can include a tip having a plurality of petals radiating from a central hub 1420. The retrieval sheath may be positioned within a transseptal sheath 1400. The mitral valve is show at the base of the left atrium 1440. The method may include the step of advancing the annular section 510, 610, 710 toward the annulus before advancing the coaptation surface 560, 660, 760 toward the annulus. The method may include the step of deploying the ventricular end or inferior surface 580 after deploying the annular portion 510.

Figure 12:
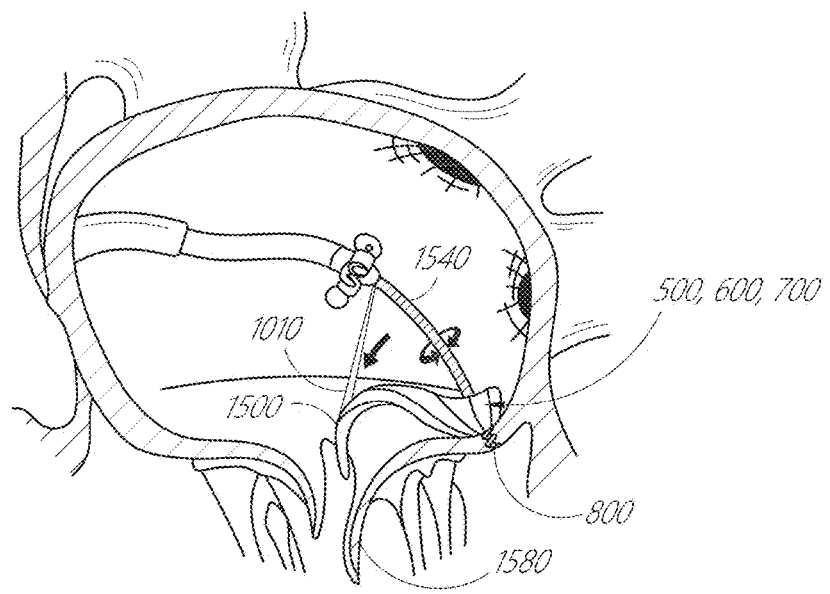
FIG. 12 schematically illustrates a method step for a transcatheter technique showing partial coaptation assistance element opening.

FIG. 12 illustrates partial deployment of the coaptation assistance element 500, 600, 700. The coaptation assistance element 500, 600, 700 may be advanced in proximity to the target location under imaging guidance such as ultrasound or fluoroscopy. The annular anchor 800 coupled with the coaptation assistance element 500, 600, 700 is engaged in tissue. An anchor torque shaft 1540 may be rotated internally and independent of the rotation of an implant torque shaft (not shown). Controlled release of a purse-string suture 1010 around the perimeter of the coaptation assistance element 500, 600, 700 may cause the coaptation assistance element 500, 600, 700 to expand. Prior to full expansion of the coaptation assistance element 500, 600, 700, rotational adjustment of the coaptation assistance element 500, 600, 700 may be performed to align the interior (ventricular) section of the coaptation assistance element 500, 600, 700 with a valve opening 1580.

The method may include the step of advancing the coaptation assistance element 500, 600, 700 toward a target location. The method may include the step of advancing the annular hub 520, 620, 720 toward a target location. The method may include the step of advancing the annular anchor 800, which is coupled to the annular hub 520, 620, 720, toward a target location. The method may include echo or fluoroscopic guidance of the annular anchor 800, the hub 520, 620, 720, and/or the coaptation assistance element 500, 600, 700. The method may include engaging the annular anchor 800 in tissue. The method may include rotating the anchor control knob 1004 to rotate the annular anchor 800. The method may include the independent rotation of the annular anchor 800 from the hub 520, 620, 720. The method may include holding the hub 520, 620, 720 stationary during rotation of the annular anchor 800. The method may include controlled release of the purse-string suture 1010. The release may cause the coaptation assistance element 500, 600, 700 to expand. The purse-string suture 1010 may be disposed within the coaptation assistance element 500, 600, 700 and/or along a perimeter of the coaptation assistance element 500, 600, 700. The purse-string suture 1010 can facilitate the collapse and/or expansion of the coaptation assistance element 500, 600, 700. The method may include rotational adjustment of the coaptation assistance element 500, 600, 700 to align an inferior edge 580, 680, 780 or ventricular section of the coaptation assistance element 500, 600, 700 with the valve opening. The method may include rotational adjustment of the coaptation assistance element 500, 600, 700 to align an inferior edge 580, 680, 780 or ventricular section around the posterior leaflet.

Figure 13:
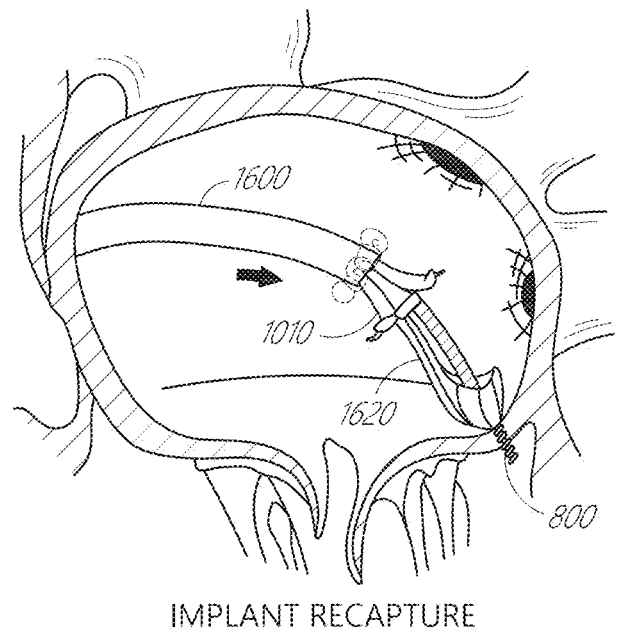
FIG. 13 schematically illustrates a method step for a transcatheter technique showing coaptation assistance element collapsing.

FIG. 13 illustrates recapture of the coaptation assistance element 500, 600, 700. The coaptation assistance element 500, 600, 700 may be recaptured by tightening a purse-string suture 1010 around a portion of the perimeter 1620 of the coaptation assistance element 500, 600, 700 to collapse the coaptation assistance element 500, 600, 700. The perimeter can include any edge, any combination of edges, or all of the edges described herein. A recapture sheath and transseptal sheath 1600 may be advanced over the collapsed coaptation assistance element 500, 600, 700. Recapture sheath petals that radiate from a central hub may roll over the coaptation assistance element 500, 600, 700 allowing the coaptation assistance element 500, 600, 700 to be retracted into the transseptal sheath. The annular anchor 800 may be unscrewed or otherwise released, and the system may be removed. The prolapsed or partially encapsulated coaptation assistance element 500, 600, 700 by the recapture sheath petals can be another mode of delivery. The encapsulated-first delivery mode can be in contrast to the hub-first and the strut-delivery modes described herein.

In some methods, recapture is an optional method step. The method may include the step of tightening of the purse-string suture 1010. This tightening may collapse the coaptation assistance element 500, 600, 700. The method may include the step of advancing the recapture sheath and/or the transseptal sheath over the collapsed coaptation assistance element 500, 600, 700. The recapture sheath can fold outward to roll over the coaptation assistance element 500, 600, 700. The method may include the step of retracting the coaptation assistance element 500, 600, 700 into the transseptal sheath. The method may include the step of rotating the annular anchor 800 to disengage tissue. The method may include the step of removing the coaptation assistance element 500, 600, 700 and the annular anchor 800.

Figure 14:
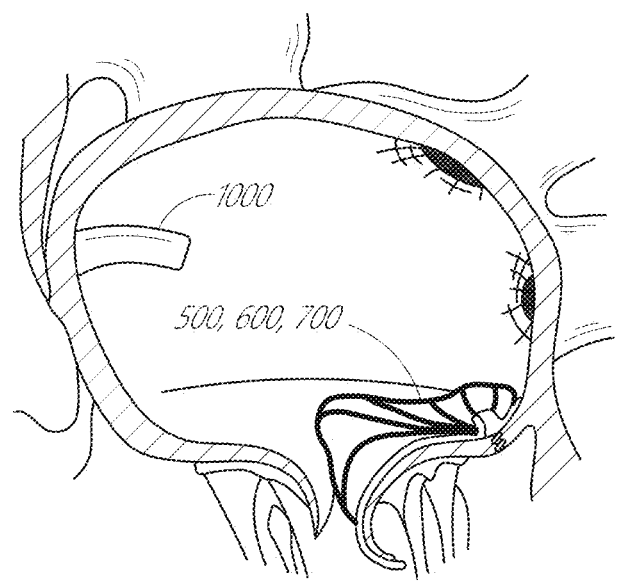
FIG. 14 schematically illustrates a method step for a transcatheter technique showing a cross-sectional view of the coaptation assistance element.

FIG. 14 illustrates a cross-section view of the deployed coaptation assistance element 500, 600, 700. The method may include the step of releasing of the coaptation assistance element 500, 600, 700. The method may include the step of retraction of the delivery catheter 1000.

Figure 15:
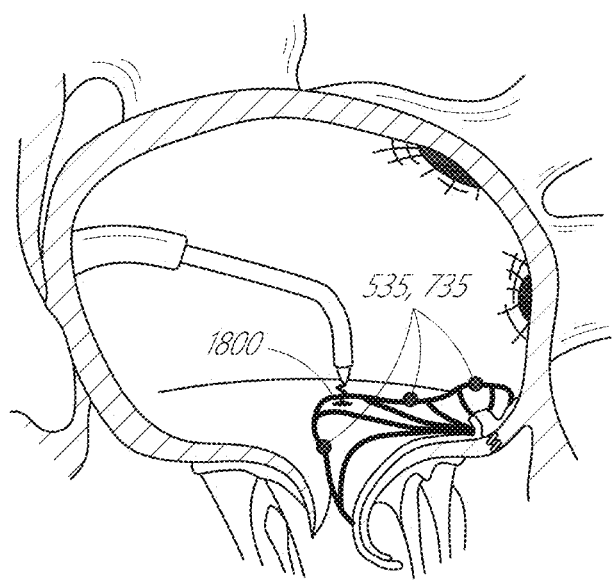
FIG. 15 schematically illustrates a method step for a transcatheter technique showing secondary anchor placement.

FIG. 15 illustrates deployment of secondary anchors. In some methods, deployment of secondary anchors is an optional method step. The method may include the step of engaging annular attachment sites 535, 735 to the annulus.

The method may include the step of engaging ventricular anchors. The method may include the step of engaging commissural anchors 1800. The method may include the step of deploying markers on strategic locations on the coaptation assistance element 500, 600, 700 and/or the annular anchor 800. The method may include the step of detecting markers, such as detecting radiopaque markers. The method may include the step of facilitating the placement of anchor 800 under fluoroscopy. The method may include the step of locating radiopaque markers along the perimeter of the coaptation assistance element 500, 600, 700 to indicate the shape of coaptation assistance element 500, 600, 700.

In some embodiments, the manufacturer provides instructions for use of the system including one or more of the steps disclose herein, or any step previously described or inherent in the drawings.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "inserting a coaptation assist body proximate the mitral valve" includes "instructing the inserting of a coaptation assist body proximate the mitral valve." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A coaptation assistance element for treating mal-coaptation of a heart valve of a heat, the heart valve having a valve annulus, the coaptation assistance element comprising:

a first coaptation surface and an opposed second surface, each of the first coaptation surface and the opposed second surface bounded by a first lateral edge, a second lateral edge, an inferior edge, and a superior edge, the superior edge forming a lip cupped downward toward the inferior edge or upward from the inferior edge;

a hub spaced radially inward from each of the first lateral edge, the second lateral edge, the inferior edge, and the superior edge; and an active anchor coupled to the hub and configured to be rotated relative to the hub to selectively deploy the active anchor at a first target location; and a plurality of struts spaced circumferentially around the hub and extending radially outward from the hub, the plurality of struts comprising at least a first strut configured to be implanted within the heart superior to the valve annulus and a second strut configured to be implanted within the heart and traversing a plane of the valve annulus, wherein the second strut has a total length that is longer than a total length of the first strut.

2. The coaptation assistance element of claim 1, wherein at least one strut of the plurality of struts has a sharpened tip configured to engage tissue.

3. The coaptation assistance element of claim 1, wherein the plurality of struts comprise Nitinol.

4. The coaptation assistance element of claim 1, wherein the active anchor is helical-shaped.

5. The coaptation assistance element of claim 1, further comprising one or more additional anchors.

6. The coaptation assistance element of claim 5, wherein the one or more additional anchors are active anchors.

7. The coaptation assistance element of claim 1, wherein the hub comprises a cross-pin configured to extend through a helix of the active anchor.

8. The coaptation assistance element of claim 1, wherein the hub is configured to mate with a delivery catheter, wherein the delivery catheter is configured to position the hub near the first target location.

9. The coaptation assistance element of claim 8, wherein the delivery catheter is configured to rotate the active anchor independently of the hub.

10. The coaptation assistance element of claim 1, further comprising a radiopaque marker.

11. The coaptation assistance element of claim 1, further comprising a plurality of radiopaque markers near the superior edge.

12. The coaptation assistance element of claim 1, wherein the lip is cupped downward toward the inferior edge.

13. The coaptation assistance element of claim 1, wherein the lip is cupped upward from the inferior edge.

14. The coaptation assistance element of claim 1, wherein the hub extends upward from the first coaptation surface.

15. The coaptation assistance element of claim 1, wherein the inferior edge curves backwards toward the hub.

16. The coaptation assistance element of claim 1, wherein the hub is tubular.

17. The coaptation assistance element of claim 1, wherein the plurality of struts and the hub are integrally formed.

18. The coaptation assistance element of claim 1, wherein the coaptation assistance element is configured to be collapsed relative to the hub.

19. The coaptation assistance element of claim 1, wherein the active anchor is configured to be selectively coupled and decoupled from tissue.

20. A coaptation assistance element for treating malcoaptation of a heart valve of a heart, the heart valve having a valve annulus, the coaptation assistance element comprising:

a first coaptation surface and an opposed second surface, each of the first coaptation surface and the opposed second surface bounded by a first lateral edge, a second lateral edge, an inferior edge, and a superior edge, a hub; and an active anchor coupled to the hub, the active anchor configured to be rotated in a first direction relative to the hub to selectively deploy the active anchor at a first target location to engage a tissue, the active anchor configured to be rotated in a second direction, opposite the first direction, relative to the hub to selectively disengage the tissue at the first target location; and a plurality of struts spaced circumferentially around the hub, the plurality of struts and the first coaptation surface extending radially outward from the hub, the plurality of struts comprising at least a first strut configured to be implanted within the heart superior to the valve annulus and a second strut configured to be implanted within the heart and traversing a plane of the valve annulus, wherein the second strut has a total length that is longer than a total length of the first strut.

21. A coaptation assistance element for treating malcoaptation of a heart valve of a heart, the heart valve having a valve annulus, an anterior leaflet, and a posterior leaflet, the coaptation assistance element comprising:

a first coaptation surface and an opposed second surface, each of the first coaptation surface and the opposed second surface bounded by a first lateral edge, a second lateral edge, an inferior edge, and a superior edge;

a hub;

an active anchor coupled to the hub and configured to be rotated relative to the hub to selectively deploy the active anchor at a first target location, wherein the active anchor is configured to be selectively deployed in the annulus, wherein the hub is configured to remain stationary as the active anchor is rotated to engage tissue; and a plurality of struts spaced circumferentially around the hub and extending radially outward from the hub, the plurality of struts comprising at least a first strut configured to be implanted within the heart superior to the valve annulus and a second strut configured to be implanted within the heart and traversing a plane of the valve annulus, wherein the second strut has a total length that is longer than a total length of the first strut.

* * * * *

UNITED STATES PATENT AND TRADEMARK OFFICE
CERTIFICATE OF CORRECTION

PATENT NO. : 9,592,121 B1
APPLICATION NO. : 15/153480
DATED : March 14, 2017
INVENTOR(S) : Alexander K. Khairkhahan Page 1 of 1

It is certified that error appears in the above-identified patent and that said Letters Patent is hereby corrected as shown below:

In the Claims

In Column 38 at Line 63, In Claim 1, change "heat," to --heart,--.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*